(12) United States Patent
Rayner et al.

(10) Patent No.: US 12,161,728 B2
(45) Date of Patent: Dec. 10, 2024

(54) REDUCING ABNORMAL ACCUMULATION OF TDP-43 IN MOTOR NEURONS IN AMYOTROPHIC LATERAL SCLEROSIS AND/OR FRONTOTEMPORAL DEMENTIA USING A CONSTRUCT ENCODING CYCLIN F

(71) Applicant: MACQUARIE UNIVERSITY, North Ryde (AU)

(72) Inventors: Stephanie Rayner, Beecroft (AU); Albert Lee, Silverwater (AU); Roger Chung, Rhodes (AU); Ian Blair, Collaroy Plateau (AU)

(73) Assignee: MACQUARIE UNIVERSITY, North Ryde (AU)

( * ) Notice: Subject to any disclaimer, the term of this patent is extended or adjusted under 35 U.S.C. 154(b) by 670 days.

(21) Appl. No.: 16/348,089

(22) PCT Filed: Nov. 7, 2017

(86) PCT No.: PCT/AU2017/051225
§ 371 (c)(1),
(2) Date: May 7, 2019

(87) PCT Pub. No.: WO2018/081878
PCT Pub. Date: May 11, 2018

(65) Prior Publication Data
US 2019/0298860 A1 Oct. 3, 2019

(30) Foreign Application Priority Data

Nov. 7, 2016 (AU) .............................. 2016904541
Mar. 23, 2017 (AU) .............................. 2017901026

(51) Int. Cl.
| | | |
|---|---|---|
| C12N 15/85 | (2006.01) | |
| A61K 48/00 | (2006.01) | |
| A61P 25/28 | (2006.01) | |
| C07K 14/47 | (2006.01) | |
| C12N 5/00 | (2006.01) | |
| C12N 15/63 | (2006.01) | |
| C12N 15/86 | (2006.01) | |
| C12N 15/861 | (2006.01) | |
| C12Q 1/6883 | (2018.01) | |
| G01N 33/50 | (2006.01) | |

(52) U.S. Cl.
CPC .......... *A61K 48/0058* (2013.01); *A61K 48/00* (2013.01); *A61P 25/28* (2018.01); *C07K 14/4738* (2013.01); *C12N 15/86* (2013.01); *C12N 15/861* (2013.01); *C12Q 1/6883* (2013.01); *G01N 33/5023* (2013.01); *G01N 33/5058* (2013.01); *C12N 2750/14141* (2013.01); *C12N 2750/14143* (2013.01); *C12Q 2600/158* (2013.01); *G01N 2500/10* (2013.01); *G01N 2800/2814* (2013.01); *G01N 2800/52* (2013.01); *G01N 2800/56* (2013.01)

(58) Field of Classification Search
CPC ...... C12N 15/63; C12N 15/861; C12N 15/86; C12N 5/0619; C07K 14/47; C07K 14/4738; A61K 48/00; A61P 25/00; A61P 25/28; A61P 25/02; A61P 25/14; A61P 25/16; G01N 33/5058; G01N 33/6896; G01N 2800/28
See application file for complete search history.

(56) References Cited

U.S. PATENT DOCUMENTS

| | | | |
|---|---|---|---|
| 10,577,604 B2* | 3/2020 | Bennett | ............... C12N 15/113 |
| 11,078,247 B2* | 8/2021 | Fotin-Mleczek | ..... C12N 15/113 |
| 2011/0203007 A1* | 8/2011 | Klein | ................. A61K 49/0008 |
| | | | 514/17.7 |
| 2016/0024496 A1* | 1/2016 | Bennett | ............... C12N 15/113 |
| | | | 435/375 |
| 2022/0362404 A1* | 11/2022 | Rayner | .................. A61P 25/28 |

FOREIGN PATENT DOCUMENTS

| | | |
|---|---|---|
| WO | WO 00/55320 A1 | 9/2000 |
| WO | WO 2014/062736 A1 | 4/2014 |

OTHER PUBLICATIONS

Bruijn et al., Annu. Rev. Neurosci. 2004, 27: 723-49.*
Lagier-Tourenne et al., Human Mol. Genet. 2010; 19: R46-R64; doi:10.1093/hmg/ddq137.*
Ju et al., PLoS Biology 2011; 9: 1-17; e1001052.*
Jackson et al. Gene Ther.2015; 22:20-28. doi: 10.1038/gt.2014.101.*
Ranganathan et al., Front. in Neurosci. 2020; doi:10.3389/fnins.2020.00684.*
Moore et al., Annu. Rev. Neurosci. 2005; 28:57-87.*
Rayner, Master Thesis, Department of Chemistry and Biomolecular Sciences, Macquarie University, published Oct. 10, 2014.*
Mitic, Amyotrophic Lateral Sclerosis: Novel strategy to clear pathologic TDP-43 aggregates, Macquarie University, published 2016.*

(Continued)

*Primary Examiner* — Chang-Yu Wang
(74) *Attorney, Agent, or Firm* — Knobbe, Martens, Olson & Bear, LLP

(57) ABSTRACT

Disclosed are compositions and methods for inhibiting abnormal protein accumulation, promoting motor neuron survival, inhibiting motor neuron degeneration and treating neurodegenerative conditions through expression of a nucleic acid sequence encoding cyclin F in motor neurons with an abnormally low level or activity of cyclin F. Also disclosed are methods for identifying agents that promote survival of motor neurons, inhibit degeneration of motor neurons and/or inhibit abnormal protein accumulation in motor neurons, identifying agents that are useful for treating neurodegenerative conditions, diagnosing neurodegenerative conditions, predicting the progression of neurodegenerative conditions, and monitoring the effectiveness of a therapy in reducing the progression of a neurodegenerative condition.

6 Claims, 8 Drawing Sheets

Specification includes a Sequence Listing.

(56) References Cited

OTHER PUBLICATIONS

The fact sheet of "Frontotemporal Dementia" from the NIH-NIA website: www.nia.nih.gov/health/what-are-frontotemporal-disorders retrieved on Sep. 28, 2022.*
The factsheet of ALS treatment from Johns Hopkins website: www.hopkinsmedicine.org/neurology_neurosurgery/centers_clinics/als/conditions/als_treatment.html retrieved on Sep. 28, 2022.*
Jackson et al., Mol. Thera. Methods & Clin. Develop. 2015; 2:15036; doi:10.1038/mtm.2015.36.*
Zhang et al., Mol. Thera. 2011; 19:1440-1448.*
International Preliminary Report on Patentability, issued May 7, 2019, in International Application No. PCT/AU2017/051225.
Anonymous, EM_STD:AY890472, Retrieved from the Internet: bis.internal.epo.org/exam/dbfetch.jsp?id=EM_STD:AY890472 [retrieved on Jul. 2, 2020], 2005.
Anonymous, UPI0000127595, Retrieved from the Internet: www.uniprot.org/uniparc/UPI0000127595 [retrieved on Jul. 2, 2020], 2002.
Extended European Search Report, dated Jul. 10, 2020, in EP Application No. 17867451.1.
Hester et al., AAV as a Gene Transfer Vector for the Treatment of Neurological Disorders: Novel Treatment Thoughts for ALS, Current Gene Therapy, vol. 9, pp. 428-433, 2009.
Chia, R., et al., Novel genes associated with amyotrophic lateral sclerosis: diagnostic and clinical implications, the Lancet Neurology, vol. 17, No. 1, pp. 94-102, 2018.
Hogan, A., Generation of novel animal models of amyotrophic lateral sclerosis, Macquarie University, Thesis Submission, pp. 1-116, 2014.
Hogan, A.L., et al., Expression of ALS/FTD-linked mutant CCNF in zebrafish leads to increased cell death in the spinal cord and an aberrant motor phenotype, Human Molecular Genetics, vol. 26, No. 14, pp. 2616-2626, 2017.
International Search Report & Written Opinion, mailed Feb. 2, 2018, in International Application No. PCT/AU2017/051225.
Lee, A., et al., Casein kinase II phosphorylation of cyclin F at serine 621 regulates the Lys48-ubiquitylation E3 ligase activity of the SCF$^{(cyclin\ F)}$ complex, Open Biology, 7:170058, 2017.
McCann, E.P., et al., The genotype-phenotype landscape of familial amyotrophic lateral sclerosis in Australia, Clinical Genetics, vol. 92, pp. 259-266, 2017.
Search Information Sheet, dated Feb. 2, 2018, in International Application No. PCT/AU2017/051225.
Williams, K.L., et al., CCNF mutations in amyotrophic lateral sclerosis and frontotemporal dementia, Nature Communications, 7:11253, 2016.
Deng et al., The role of FUS gene variants in neurodegenerative diseases. Nature Reviews. Neurology. Jun. 2014, vol. 10. pp. 337-348.
Galper et al., Cyclin F: A component of an E3 ubiquitin ligase complex with roles in neurodegeneration and cancer. International Journal of Biochemistry and Cell Biology. Elsevier. 2017. pp. 216-220.
Ke et al., Short-term suppression of A315T mutant human TDP-43 expression improves functional deficits in a novel inducible transgenic mouse model of FTLD-TDP and ALS. Acta Neuropathol. 2015, vol. 130. pp. 661-678.
Limia et al., "Emerging Perspectives on Gene Therapy Delivery for Neurodegenerative and Neuromuscular Disorders". Journal of Personalized Medicine. 2022, 12, 1979. doi.org/10.3390/jpm12121979. pp. 1-35.
Ling et al., Converging Mechanisms in ALS and FTD: Disrupted RNA and Protein Homeostasis. Neuron 79. Aug. 2013. pp. 416-438.
Liu et al., Disease Animal Models of TDP-43 Proteinopathy and Their Pre-Clinical Applications. International Journal od Molecular Sciences. 2013, vol. 14. ISSN 1422-0067. doi:10.3390/ijms141020079. pp. 20079-20111.
Maguire et al., "Gene Therapy for the Nervous System: Challenges and New Strategies". Neurotherapeutics. Aug. 2014, vol. 11. pp. 817-839.
Maruyama, et al. Mutations of optineurin in amyotrophic lateral sclerosis. Nature. May 2010, vol. 465. doi: 10.1038/nature08971. pp. 223-228.
McCann et al., The genotype-phenotype landscape of familial amyotrophic lateral sclerosis in Australia. Clinical Genetics. Wiley Online Library. Jan. 2017. pp. 259-266. doi: 10.1111/cge.12973.
Neumann et al., Ubiquitinated TDP-43 in Frontotemporal Lobar Degeneration and Amyotrophic Lateral Sclerosis. Science. Oct. 2006, vol. 314. doi: 10.1126/science.1134108. pp. 130-135.
Oakes et al., TBK1: a new player in ALS linking autophagy and neuroinflammation. Molecular Brain. 2017. doi: 10.1186/x13041-017-0287-x. pp. 1-10.
Rayner et al. TDP-43 is a ubiquitylation substrate of the SCFcyclin F complex. Neurobiology of Disease 167 (2022) 105673. Elsevier. pp. 1-11.
Renaud et al. Key role of UBQLN2 in pathogenesis of amyotrophic lateral sclerosis and frontotemporal dementia. Acta Neuropathologica Communications. (2019) 7:103. pp. 1-11.
Sanchez-Dengra et al., "Access to the CNS: Strategies to overcome the BBB". International Journal of Pharmaceutics (2023). doi: doi.org/10.1016/l.llpharm.2023.122759. pp. 1-60.
Smeyers et al. C9ORF72: What It Is, What It Does, and Why It Matters Frontiers in Cellular Neuroscience. May 2021, vol. 15, Article 661447. pp. 1-16.
Sreedharan et al., TDP-43 Mutations in Familial and Sporadic Amyotrophic Lateral Sclerosis, Science. American Association for the Advancement of Science. Mar. 2008, New Series, vol. 319, No. 5870. pp. 1668-1672.
Swarup et al., Pathological hallmarks of amyotrophic lateral sclerosis/frontotemporal lobar degeneration in transgenic mice produced with TDP-43 genomic fragments. Brain. A Journal of Neurology. 2011, vol. 134. pp. 2610-2626.
Watanabe et al., Accelerated Disease Onset with Stabilized Familial Amyotrophic Lateral Sclerosis (ALS)-linked Mutant TDP-43 Proteins. The Journal of Biological Chemistry. Feb. 2013, vol. 2888, No. 5. pp. 3641-3654.
Weil et al., Role of Optineurin in the Mitochondrial Dysfunction: Potential implications in Neurodegenerative Diseases and Cancer. Frontiers in Immunology. Jun. 2018, vol. 9, Article 1243. pp. 1-23.
Xu et al., Wild-Type Human TDP-43 Expression Causes TDP-43 Phosphorylation, Mitochondrial Aggregation, Motor Deficits, and Early Mortality in Transgenic Mice. Neurobiology of Disease. The Journal of Neuroscience. Aug. 2010, vol. 30. pp. 10841-10859.
Williams et al., CCNF mutations in amyotrophic lateral sclerosis and frontotemporal dementia. Nature Communications. Apr. 2016, 7:11253. pp. 1-8. doi: 10.1038/ncomms11253.
Donnelly et al., RNA toxicity from the ALS/FTD C9ORF72 expansion is mitigated by antisense intervention, Neuron, vol. 80, pp. 415-428, 2013.
Mackenzie et al., The role of TDP-43 in amyotrophic lateral sclerosis and frontotemporal dementia, Curr Opin Neurol, vol. 21, No. 6, pp. 693-700, 2008.

* cited by examiner

A

REDUCING ABNORMAL ACCUMULATION OF TDP-43 IN MOTOR NEURONS IN AMYOTROPHIC LATERAL SCLEROSIS AND/OR FRONTOTEMPORAL DEMENTIA USING A CONSTRUCT ENCODING CYCLIN F

FIELD OF THE INVENTION

This application is the U.S. National Stage Application under 35 U.S.C. § 371 of International Application No. PCT/AU2017/051225, filed Nov. 7, 2017, designating the U.S. and published in English as WO 2018/081878 A1 on May 11, 2018, which claims priority to Australian Provisional Application No. 2016904541 entitled "Modulation of protein accumulation and uses therefor" filed 7 Nov. 2016 and Australian Provisional Patent Application No. 2017901026 entitled "Modulation of protein accumulation and uses therefor" filed 23 Mar. 2017, the contents of which are incorporated herein by reference in their entirety.

REFERENCE TO SEQUENCE LISTING

A Sequence Listing submitted as an ASCII text file via EFS-Web is hereby incorporated by reference in accordance with 37 U.S.C. § 1.52 (e). The name of the ASCII text file for the Sequence Listing is 56239677_1.txt, the date of creation of the ASCII text file is Sep. 2, 2022, and the size of the ASCII text file is 27 KB.

This invention relates generally to neurodegenerative conditions. More particularly, the present invention relates to compositions and methods for inhibiting abnormal protein accumulation, promoting motor neuron survival, inhibiting motor neuron degeneration and treating neurodegenerative conditions through expression of a nucleic acid sequence encoding cyclin F in motor neurons with an abnormally low level or activity of cyclin F. The present invention also relates to methods for identifying agents that promote survival of motor neurons, inhibit degeneration of motor neurons and/or inhibit abnormal protein accumulation in motor neurons, identifying agents that are useful for treating neurodegenerative conditions, diagnosing neurodegenerative conditions, predicting the progression of neurodegenerative conditions, and monitoring the effectiveness of a therapy in reducing the progression of a neurodegenerative condition.

BACKGROUND OF THE INVENTION

Amyotrophic lateral sclerosis (ALS) is the most common form of a group of neurodegenerative diseases collectively referred to primarily based upon their clinical presentation as motor neuron disease (MND). ALS is a late-onset fatal disorder characterized by paralysis and degeneration of muscles due to the progressive death of motor neurons in the brain and spinal cord. Around 20% of ALS patients are also diagnosed with frontotemporal dementia (FTD) and segregation of both ALS and FTD may be seen within individual families, particularly those with mutations in C9ORF72 (Neumann et al., 2007. Archives of Neurology 64:1388-1394; Bigio et al., 2013. Acta Neuropathologica 125:463-465). While the biological basis of ALS remains poorly understood, several recent discoveries are providing insights into the pathogenic mechanisms. Understanding the biology of familial cases offers a unique opportunity to better understand sporadic ALS.

Approximately 10% of ALS cases have a positive family history (familial ALS) and appear clinically indistinguishable from sporadic ALS cases. Mutations in numerous genes responsible for RNA metabolism (such as TDP43 (Neumann et al., 2006, Science 314:130-133) and FUS (Mackenzie et al., 2010, Lancet Neurology 9:995-1007)) and protein degradation (such as UBQLN2 (Williams et al., 2012, Neurobiology of Aging 33:2527 e2523-2510) and TBK1 (Cirulli et al., 2015, Science 347:1436-1441, Freischmidt et al., 2015, Nature Neuroscience 18:631-636)) have been implicated in the etiology of familial ALS. In a recent study, mutations to a new ALS gene, CCNF, were identified in familial and sporadic ALS/FTD patients (Williams et al., 2016, Nat Commun 7:11253). CCNF encodes Cyclin F, a component of the Skp1-Cul1-F-box (SCF) E3 ubiquitin-protein ligase complex that is an integral part of a cell's recycling system that ubiquitinates unneeded and damaged proteins for degradation by the proteasome (Bai et al., 1996, Cell 86:263-274). The CCNF mutations identified by William et al. (2016, supra) were shown to lead to defective protein degradation and signature features of ALS pathogenesis in vitro and in vivo.

Protein degradation is an essential cellular process that is carried out by two major intracellular protein degradation pathways: the ubiquitin-proteasome system (UPS) and autophagy. Normal autophagy is a dynamic multi-step process that prevents protein accumulation via sequestration into autophagic vacuoles (autophagosomes). Subsequent fusion of the autophagosomes with lysosomes results in protein degradation. Interruption of this process results in accumulation of protein aggregates and neurodegeneration.

In neurodegenerative conditions, normal autophagic flux is altered, resulting in the accumulation of autophagic vacuoles or autophagosomes. A hallmark pathological feature of most ALS and FTD cases is the presence of abnormally ubiquitinated proteins, particularly TDP-43, in neuronal cytoplasmic inclusions (Neumann et al., 2013. Nat. Rev. Neurosci. 14, 248-264). Ubiquitin is a small (8.5 kDa) regulatory protein that is attached to lysine residues of a substrate protein post-translationally to signal for i) their degradation via the proteasome, ii) alter their cellular location and activity, and/or iii) promote or prevent protein interactions (Komander and Rape, 2012). Ubiquitination is carried out in three main steps: activation by E1s, ubiquitin conjugation by E2s, and substrate ligation by E3s, respectively. The result of this sequential cascade binds ubiquitin to lysine residues on proteins via different linkages directing the proteins to different functions. The findings of William et al. (2016, supra) indicate that mutated versions of CCNF contribute to abnormal ubiquitination and accumulation of ubiquitinated proteins, including TDP-43, which may fundamentally underlie the abnormal protein degradation that triggers motor neuron death.

SUMMARY OF THE INVENTION

The present invention arises in part from the determination (1) that TDP-43 is an interaction partner and substrate of the SCF$^{Cyclin\ F}$ complex, (2) that a deficiency in cyclin F leads to an accumulation of TDP-43 in motor neurons and (3) that a subset of patients with a neurodegenerative condition have an abnormally low level or activity of cyclin F in motor neurons. Based on these findings, the present inventors propose that increasing cyclin F levels in motor neurons in this subset of patients with a neurodegenerative condition will reduce abnormal accumulation of proteins and thereby enhance motor neuron survival, as described hereafter.

Accordingly, in one aspect, the present invention provides methods for promoting survival of a motor neuron with a reduced level or activity of cyclin F relative to a control. These methods generally comprise, consist or consist essentially of increasing or stimulating expression of a nucleic acid sequence encoding cyclin F in the motor neuron, thereby promoting survival of the motor neuron.

Another aspect of the present invention provides methods for inhibiting degeneration of a motor neuron with a reduced level or activity of cyclin F relative to a control. These methods generally comprise, consist or consist essentially of increasing or stimulating expression of a nucleic acid sequence encoding cyclin F in the motor neuron, thereby inhibiting degeneration of the motor neuron.

In yet another aspect, the present invention provides methods for inhibiting abnormal protein accumulation in a motor neuron with a reduced level or activity of cyclin F relative to a control. These methods generally comprise, consist or consist essentially of increasing or stimulating expression of a nucleic acid sequence encoding cyclin F in the motor neuron, thereby inhibiting abnormal protein accumulation in the motor neuron. Suitably, the abnormal protein accumulation comprises abnormal accumulation proteins (e.g., proteins that are susceptible to protein accumulation or aggregation such TDP-43).

Still another aspect of the present invention provides methods for treating a neurodegenerative condition in a subject having a motor neuron with a reduced level or activity of cyclin F relative to a control. These methods generally comprise, consist or consist essentially of increasing or stimulating expression of a nucleic acid sequence encoding cyclin F in the motor neuron, thereby treating the neurodegenerative condition. Suitably, the methods further comprise determining that the subject has a motor neuron with a reduced level or activity of cyclin F relative to a control, prior to increasing expression or stimulating expression of the nucleic acid sequence encoding cyclin F in the motor neuron. In specific embodiments, the methods comprise introducing into the motor neuron a construct comprising a nucleic acid sequence encoding cyclin F operably connected to a promoter that is operable in the motor neuron. In illustrative examples of this type, the construct is in the form of a viral vector (e.g., an adeno-associated virus (AAV) vector).

A further aspect of the present invention provides methods for treating a neurodegenerative condition in a subject having a motor neuron with a reduced level or activity of cyclin F relative to a control. These methods generally comprise, consist or consist essentially of administering a construct comprising a nucleic acid sequence encoding cyclin F operably connected to a promoter that is operable in the motor neuron. Suitably, the construct is in the form of a viral vector (e.g., an AAV vector). In specific embodiments, the methods further comprise determining that the subject has a motor neuron with a reduced level or activity of cyclin F relative to a control, prior to administration of the construct.

Yet another aspect of the present invention provides a recombinant viral vector comprising a nucleic acid sequence encoding cyclin F operably connected to a promoter that is operable in a motor neuron. Suitably, the recombinant viral vector is an AAV vector.

The present invention also provides in another aspect methods of identifying a candidate agent for treating or preventing a neurodegenerative condition. These methods generally comprise, consist or consist essentially of: (a) contacting a population of cells with a test agent, wherein the cells have a reduced level or activity of cyclin F relative and/or abnormal protein accumulation relative to a control; and (b) measuring (i) the level or activity of cyclin F and/or (ii) abnormal protein accumulation in the cells, in the presence of the test agent, and (c) identifying the candidate agent for treating or preventing a neurodegenerative condition, wherein the test agent is a candidate agent for treating or preventing a neurodegenerative condition if the test agent (i) increases the level or activity of cyclin F or (ii) reduces abnormal protein accumulation, in the presence of the test agent. Suitably, the cells are selected from motor neurons or cells that are surrogates for motor neuron cells (e.g., skin cells such as skin fibroblasts, or blood cells such as a peripheral blood mononuclear cells, etc., which exhibit similar disease-associated molecular characteristics to motor neurons).

In another aspect, the present invention provides methods for diagnosing the presence of a neurodegenerative condition in a subject. These methods generally comprise, consist or consist essentially of detecting in the subject a motor neuron or a cell that is a surrogate for a motor neuron having a reduced level of cyclin F relative to a control.

Still another aspect of the present invention provides methods for diagnosing the presence of a neurodegenerative condition in a subject. These methods generally comprise, consist or consist essentially of: (a) obtaining a sample comprising cells from the subject; (b) conducting at least one assay on the cells in the sample to detect the level or activity of cyclin F in the cells; and (c) diagnosing the subject as having a neurodegenerative condition if the level or activity of the cyclin F in the cells is reduced relative to a level or activity of cyclin F in a control sample. In specific embodiments, the cells are selected from motor neurons or cells that are surrogates for motor neurons.

Yet another aspect of the present invention provides kits for diagnosing the presence of a neurodegenerative condition in a subject, comprising one or more reagents for determining the level or activity of cyclin F in a motor neuron and optionally instructions for carrying out that determination.

Another aspect of the present invention provides methods for predicting the progression of a neurodegenerative condition in a subject. These methods generally comprise, consist or consist essentially of: (a) obtaining a first sample from the subject, wherein the first sample comprises motor neurons and/or cells that are surrogates for motor neurons (e.g., skin cells such as skin fibroblasts, blood cells such as peripheral blood mononuclear cells, etc.); (b) obtaining a second sample from the subject at a time which is later than when the first sample was obtained, wherein the second sample comprises motor neurons and/or cells that are surrogates for motor neurons (e.g., skin cells such as skin fibroblasts, blood cells such as peripheral blood mononuclear cells, etc.); (c) conducting at least one assay on the cell samples to detect a level or activity of cyclin F; and (d) predicting the progression of the neurodegenerative condition in the subject, wherein: (i) the neurodegenerative condition is predicted to progress if the level or activity of cyclin F in the second sample is decreased relative to the level or activity of cyclin F in the first sample; or (ii) the neurodegenerative condition is not predicted to progress if the level or activity of cyclin F in the second sample is increased or unchanged relative to the level or activity of cyclin F in the first sample.

A further aspect of the present invention provides methods of monitoring the effectiveness of a therapy in reducing the progression of a neurodegenerative condition in a subject. These methods generally comprise, consist or consist essentially of: (a) conducting at least one assay to determine the level or activity of cyclin F in a sample comprising motor neurons and/or cells that are surrogates for motor neurons (e.g., skin cells such as skin fibroblasts, blood cells such as peripheral blood mononuclear cells, etc.) from a subject having a neurodegenerative condition prior to and following administration of the therapy to the subject; and (b) comparing the level or activity of cyclin F in the sample from the subject prior to the administration of the therapy to the level or activity of cyclin F in the sample from the subject following administration of the therapy; and (c) monitoring the effectiveness of the therapy in reducing the progression of the neurodegenerative condition in the subject, wherein an increase in the level or activity of cyclin F in the sample following administration of the therapy as compared to the level or activity of cyclin F in the sample prior to the administration of the therapy is an indication that the therapy is effective in reducing the progression of the neurodegenerative condition in the subject.

In any of the aspect and embodiments described above and elsewhere herein, the neurodegenerative condition is typically characterized by motor neuron degeneration and in specific embodiments, the neurodegenerative condition is selected from ALS and FTD.

TABLE A

DESCRIPTION OF THE SEQUENCES

Figure 1:
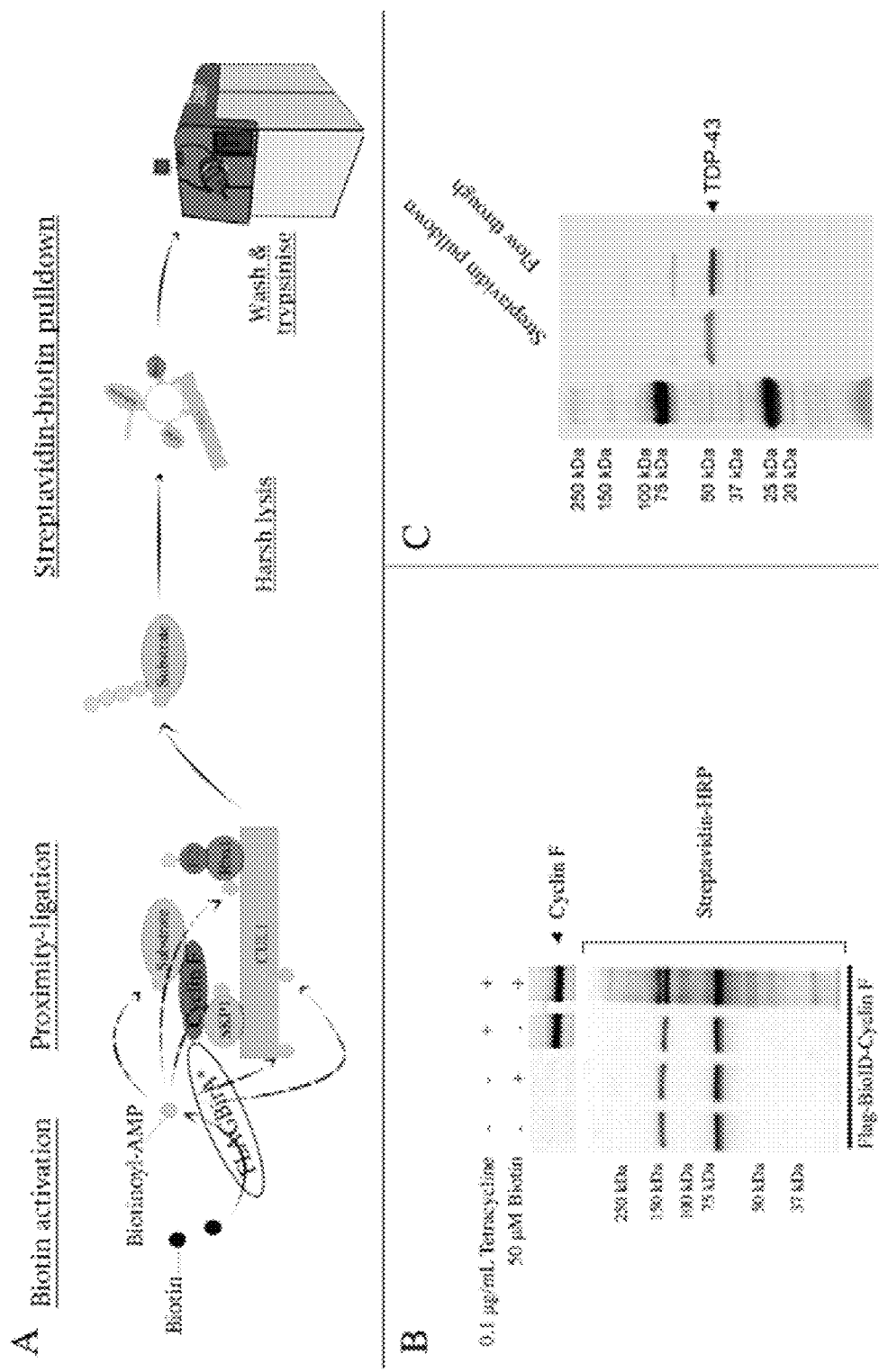
FIG. 1 is a schematic and photographic representation depicting labeling of the proteome in live cells. A. Schematic for biotinylation using BioID-Cyclin F. B. Cyclin F-BirA* biotinylates proteins upon the addition of 50 μM biotin to culture media and further incubation for 24 hours. C. Immunoblotting indicates endogenous TDP-43 is biotinylated by Cyclin F-BirA* in live Flp-In T-Rex 293 cells.

| GenBank Accession No. | SEQUENCE | SEQ ID NO: |
|---|---|---|
| NM_001323538 | ctgcgcctgcgcgagggctacgcgcgctccggccggggcgcgggcgcgctctcaggcg<br>ggctccggcggcagcgacgcgagcgcggcgatggggagcggcggcgtggtccactgt<br>aggtgtgccaagtgtttctgttatcctacaaagcgaagaataaggaggaggccccgaaa<br>cctgaccatcttgagtctccccgaagatgtgctctttcacatcctgaaatggctttctgtaga<br>ggacatcctggccgtccgagctgtacactcccagctgaaggacctggtggacaaccacg<br>ccagtgtgtgggcatgtgccagcttccaggagctgtggccgtctccagggaacctgaag<br>ctctttgaaagggctgctgaaaaggggaatttcgaagctgctgtgaagctgggcatagc<br>ctacctctacaatgaaggcctgtctgtgtctgatgaggcccgcgcagaagtgaatggcct<br>gaaggcctctcgcttcttcagtctcgctgagcggctgaatgtgggtgccgcacctttcatct<br>ggctcttcatccgccctccgtggtcggtgagcggaagctgctgcaaggccgtggttcacg<br>agagcctcagggcagagtgccagctgcagaggactcacaaagcatccatattgcactgc<br>ttgggcagagtgctgagtctgttcgaggatgaggagaagcagcagcaggcccatgacc<br>tgtttgaggaggctgctcatcagggatgtctgaccagctcctacctcctctgggaaagcg<br>acaggaggacagatgtgtcagatcctgggcgatgcctccacagcttccgaaaactcagg<br>gactacgctgccaaaggctgctgggaagcgcagctgtctttagccaaagcctgtgcaaat<br>gcaaaccagcttggactggaggtgagagcttccagtgagatcgtctgccagctatttcag<br>gcttcccaggctgtcagtaaacaacaagtcttctccgtgcagaagggactcaatgacaca<br>atgaggtacattctgatcgactggctggtggaagttgccaccatgaaggacttcacaagc<br>ctgtcctgcacctgaccgtggagtgtgtggaccggtacctgcggaggaggctggtgcc<br>gcggtacaggctccagctgctgggcatcgcctgcatggtcatctgcacccggtttatcagt<br>aaagagatcctgaccatccggaggccgtatggctcacggacaacacttacaagtacga<br>ggacctggtgagaatgatgggcgagatcgtctccgccttggaagggaagattcgagtcc<br>ccactgtggtggattacaaggaggtcctgctgacgctagtccctgtggagctgagaaccc<br>agcacctgtgcagcttcctctgcgagctctccctgctgcacaccagcctgtccgcctacgcc<br>ccagcccgcctggctgccgcagccctgctcctggccagactgacgcacgggcagacaca<br>gccctggaccactcagctgtgggacctcaccggattctcctatgaagacctcattccctgc<br>gtcttgagcctccataagaagtgcttccatgatgacgcccccaaggactacaggcaagtc<br>tctctgaccgccgtgaagcagcggtttgaggacaagcgctatggagaaatcagccagg | 1 |

TABLE A-continued

DESCRIPTION OF THE SEQUENCES

| GenBank Accession No. | SEQUENCE | SEQ ID NO: |
|---|---|---|
| | aagaggtgctgagctacagccagttgtgtgctgcattaggagtgacacaagacagcccc<br>gaccccccgactttcctcagcacaggggagatccacgccttcctcagctctccctcggggc<br>ggagaaccaaacggaagcgggagaacagcctccaggaagacagaggcagcttcgtta<br>ccaccccactgcggagctgtccagccaggaggagacgctgctgggcagcttcctcgac<br>tggagcctggactgctgctctggctatgaaggcgaccaggagagtgagggcgagaagg<br>agggcgacgtgacagctcccagcggcatcctcgatgtcaccgtggtctacctgaaccca<br>gaacagcattgctgccaggaatccagtgatgaggaggcttgtccagaggacaagggac<br>cccaggacccacaggcactggcgctggacacccagatccctgcaaccctggacccaaa<br>cccctggtccgcaccagccgggagcagggaaggacgtcacgacctcagggtactcctc<br>cgtcagcaccgcaagtcccacaagctccgtggacggtggcttggggggccctgccccaac<br>ctacctcagtgctgtccctggacagtgactcgcacacacagccctgccaccatcaggcca<br>ggaagtcatgtttacagtgtcgtccccaagtccccggagagcagtgttccccagcaac<br>aggtgaagcggataaacctatgcatacacagtgaggaggaggacatgaacctgggcct<br>tgtgaggctgtaagtgtgtcagcacatttgccgcagtggatgtgtactgaggggctgga<br>ggcgaagggtgggagcatagcataggaacgctgcatagaccatggaggcctttgcgca<br>gagagcagagaggatgacttgccgccaccaagtttctgtctccgcgggagtcccgtgca<br>agccatcagaatgttgaaatgagggtgaagagctcagatccctctctttggaaagtttag<br>cctggaagcagttggccacactgtgtggagggcacctctctgtcccttccgtgtctcactgt<br>ctctggaagcttcagcccatgtgtgtcctggtgttcccagccccaccagagcccccgtgccg<br>ggagctgacagctttcacgcttaaggcacgtgtgacctgggtagtcagacaccacttgag<br>cccctgcccacatctgctggtttggggcttcagtggggagctgacagctgtgagcacacc<br>actgtcccctcatccacctcggcctgcatggggcacccacttccttctgggtggggcttcca<br>tggtaagggggcctgcgtccctgcacactgcgaggactgccttggccacaggccactcc<br>ctacgacacgtgactcgttttagagctctgtcccagaggcgttcgtatgtgacccacagat<br>ggcgtcaatgtgaacacctctctttgtgctgaatttctgggccattcttttcctgtcttatttct<br>aaatttccttcttccaagatgaaaacaaagaaaaacttaaaacagaaggtattaaaaa<br>aacaagagattcccaccattatttaggttcacctgcaaaacaaaaatcttactccagcccc<br>tcaatgccatcctgacacactttatgcaaaaagaattttcccagataggctagccagaaa<br>aaacttcaagtcctctgtaacatctgaggtgaccaagaggcagaagagcagagcagtc<br>gggggccgtgtcctggctgatcccaactgcagctctgctgtgggggcccgtgggaggga<br>ggcagacccctgggctttcctgctggccacggagactctgctcctgcatggaaagggag<br>cctgggagccagcagcccacgcctggggagcctgcctgggcatgtgaccatggcctc<br>tccctgggaacgggctgaccacaacacaccctgctgccatccacttctgtttactctgcaa<br>atgtaagaaagaaccacttggccagaagtgtccccagatgcttttttttttttttttgga<br>gacagttttgctcttgtctccccggctggagtgcagtggcatgatctcaactctcaactcac<br>tgtaacctccgcctcccggatactcctgcctcagcctcctgggtagctgggattacaaga<br>cccaaccacgcccagctaattttttgtattttcggtagagacgggatttcaccatgttggcca<br>ggctagtctcgaactcatgacctcaagtgatccgcccacttcggtctcccaaagtgctggg<br>attacaggcatgagccacggcgcctggccccaaatgctcttgaaccggaaacccaggg<br>atgggagatgctcactgagctgetgcttttatgtgtgctggtgetatgtgtgttcatgtccgc<br>ggcagctgtctttttgctactataagggaattctggccaccctgggtggggtgtggtcggg<br>gtgagaacccaagcgttggaactgtagaccccgtcctgtcgactgtgtgccctgggcatg<br>tgtgagcctcagtttcctcatctgtaagggggcaatgataccatacctcacaggggtgttg<br>tgaggattaaatgtgaggaggatagtggcagatg | |
| NM_001323538 CDS | atggggagcggcggcgtggtccactgtaggtgtgccaagtgtttctgttatcctacaaag<br>cgaagaataaggaggaggccccgaaacctgaccatcttgagtctccccgaagatgtgct<br>ctttcacatcctgaaatggctttctgtagaggacatcctggccgtccgagctgtacactccc<br>agctgaaggacctggtggacaaccacgccagtgtgtgggcatgtgccagcttccaggag<br>ctgtggccgtctccagggaacctgaagctctttgaaagggctgctgaaaaggggaatttc<br>gaagctgctgtgaagctgggcatagcctacctctacaatgaaggcctgtctgtgtctgatg<br>aggcccgcgcagaagtgaatggcctgaaggcctctcgcttcttcagtctcgctgagcggc<br>tgaatgtgggtgccgcacctttcatctggctcttcatccgccctccgtggtcggtgagcgga<br>agctgctgcaaggccgtggttcacgagagcctcagggcagagtgccagctgcagagga<br>ctcacaaagcatccatattgcactgcttgggcagagtgctgagtctgttcgaggatgagg<br>agaagcagcagcaggcccatgacctgtttgaggaggctgctcatcagggatgtctgacc<br>agctcctacctcctctgggaaagcgacaggaggacagatgtgtcagatcctgggcgatg<br>cctccacagcttccgaaaactcagggactacgctgccaaaggctgctgggaagcgcagc<br>tgtctttagccaaagcctgtgcaaatgcaaaccagcttggactggaggtgagagcttcca<br>gtgagatcgtctgccagctatttcaggcttcccaggctgtcagtaaacaacaagtcttctcc<br>gtgcagaagggactcaatgacacaatgaggtacattctgatcgactggctggtggaagt<br>tgccaccatgaaggacttcacaagcctgtgcctgcacctgaccgtggagtgtgtggaccg<br>gtacctgcggaggaggctggtgccgcggtacaggctccagctgctgggcatcgcctgca<br>tggtcatctgcacccggtttatcagtaaagagatcctgaccatccgggaggccgtatggct<br>cacggacaacacttacaagtacgaggacctggtgagaatgatgggcgagatcgtctccg<br>ccttggaagggaagattcgagtccccactgtggtggattacaaggaggtcctgctgacg<br>ctagtccctgtggagctgagaacccagcacctgtgcagcttcctctgcgagctctccctgct<br>gcacaccagcctgtccgcctacgcccagcccgcctggctgccgcagccctgctcctggc<br>cagactgacgcacgggcagacacagccctggaccactcagctgtgggacctccaccgga<br>ttctcctatgaagacctcattccctgcgtcttgagcctccataagaagtgcttccatgatgac<br>gcccccaaggactacaggcaagtctctctgaccgccgtgaagcagcggtttgaggacaa<br>gcgctatgagaaatcagccaggaagaggtgctgagctacagccagttgtgtgctgcat<br>taggagtgacacaagacagccccgaccccccgactttcctcagcacaggggagatccac<br>gccttcctcagctctccctcggggcggagaaccaaacggaagcgggagaacagcctcc | 2 |

TABLE A-continued

DESCRIPTION OF THE SEQUENCES

| GenBank Accession No. | SEQUENCE | SEQ ID NO: |
|---|---|---|
| | aggaagacagaggcagcttcgttaccaccccactgcggagctgtccagccaggagga gacgctgctgggcagcttcctcgactggagcctggactgctgctctggctatgaaggcga ccaggagagtgagggcgagaaggagggcgacgtgacagctcccagcggcatcctcga tgtcaccgtggtctacctgaacccagaacagcattgctgccaggaatccagtgatgagga ggcttgtccagaggacaagggaccccaggacccacaggcactggcgctggacacccag atccctgcaacccctggacccaaaccctggtccgcaccagccgggagccagggaagg acgtcacgacctcagggtactcctccgtcagcaccgcaagtcccacaagctccgtggacg gtggcttgggggccctgccccaacctacctcagtgctgtccctggacagtgactcgcaca cacagccctgccaccatcaggccaggaagtcatgtttacagtgtcgtcccccaagtccccc ggagagcagtgttcccagcaacaggtgaagcggataaacctatgcatacacagtgag gaggaggacatgaacctgggccttgtgaggctgtaa | |
| NP_001752 | MGSGGVVHCRCAKCFCYPTKRRIRRRPRNLTILSLPEDVLFHILKWLSV EDILAVRAVHSQLKDLVDNHASVWACASFQELWPSPGNLKLFERAAE KGNFEAAVKLGIAYLYNEGLSVSDEARAEVNGLKASRFFSLAERLNVGA APFIWLFIRPPWSVSGSCCKAVVHESLRAECQLQRTHKASILHCLGRVL SLFEDEEKQQQAHDLFEEAAHQGCLTSSYLLWESDRRTDVSDPGRCL HSFRKLRDYAAKGCWEAQLSLAKACANANQLGLEVRASSEIVCQLFQA SQAVSKQQVFSVQKGLNDTMRYILIDWLVEVATMKDFTSLCLHLTVEC VDRYLRRRLVPRYRLQLLGIACMVICTRFISKEILTIREAVWLTDNTYKY EDLVRMMGEIVSALEGKIRVPTVVDYKEVLLTLVPVELRTQHLCSFLCEL SLLHTSLSAYAPARLAAAALLLARLTHGQTQPWTTQLWDLTGFSYEDLI PCVLSLHKKCFHDDAPKDYRQVSLTAVKQRFEDKRYGEISQEEVLSYS QLCAALGVTQDSPDPPTFLSTGEIHAFLSSPSGRRTKRKRENSLQEDR GSFVTTPTAELSSQEETLLGSFLDWSLIDCCSGYEGDOESEGEKEGDVT APSGILDVTVVYLNPEQHCCQESSDEEACPEDKGPQDPQALALDTQIP ATPGPKPLVRTSREPGKDVTTSGYSSVSTASPTSSVDGGLGALPOPTS VLSLDSDSHTQPCHHOARKSCLQCRPPSPPESSVPQQQVKRINLCIHS EEEDMNLGLVRL | 3 |
| NM_001323538 | ggtctgcgcctgcgcgagggctacgcgcgctccggccggggcgcgggcgcgctctcag gcgggctccggcggcagcgacgcgagcgcggcgatggggagcggcggcggtggtccac tgtaggtgtgccaagtgtttctgttatcctacaaagcgaagaataaggaggaggccccg aaacctgaccatcttgagtctccccgaagatgtgctctttcacatcctgaaatggctttctgt agaggacatcctggccgtccgagctggctgctgaaaaggggaatttcgaagctgctgtg aagctgggcatagcctacctctacaatgaaggcctgtctgtgtctgatgaggcccgcga gaagtgaatggcctgaaggcctctcgcttcttcagtctcgctgagcggctgaatgtgggt gccgcaccttcatctggctcttcatccgccctccgtggtcggtgagcggaagctgctgca aggccgtggttcacgagagcctcagggcagagtgccagctgcagaggactcacaaagc atccatattgcactgcttgggcagagtgctgagtctgttcgagtgaggagaagcga agcaggccatgacctgtttgaggaggctgctcatcagggatgtctgaccagctcctacc tcctctgggaaagcgacaggaggacagatgtgtcagatcctgggcgatgcctccacagc ttccgaaaactcagggactacgctgccaaagctgctgggaagcgcagctgtctttagcc aaagcctgtgcaaatgcaaaccagcttggactggaggtgaggcttccagtgagatcgt ctgccagctattttcaggcttcccaggctgtcagtaaacaacaagtcttctccgtgcagaag ggactcaatgacacaatgaggtacattctgatcgactggctggtggaagttgccaccatg aaggacttcacaagcctgtgcctgcacctgaccgtggagtgtgtggaccggtacctgcgg aggaggctggtgccgcggtacaggctccagctgctgggcatcgcctgcatggtcatctgc acccggtttatcagtaaagagatcctgaccatccgggaggccgtatggctcacggacaa cacttacaagtacgaggacctggtgagaatgatgggcgagatcgtctccgccttggaag ggaagattcgagtccccactgtggtggattacaaggaggtcctgctgacgctagtccctg tggagctgagaacccagcacctgtgcagcttcctctgcgagctctccctgctgcacaccag cctgtccgcctacgccccagcccgcctggctgccgcagccctgctcctggccagactgac gcacgggcagacacagccctggaccactcagctgtgggacctcaccggattctcctatga agacctcattccctgcgtcttgagcctccataagaagtgcttccatgatgacgccccaag gactacaggcaagtctctctgaccgccgtgaagcagcggtttgaggacaagcgctatgg agaaatcagccaggaagaggtgctgagctacagccagttgtgtgctgcattaggagtga cacaagacagccccgaccccgactttcctcagcacagggagatccacgccttcctca gctctcctcggggcgagaaccaaacgaagcgggagaacagcctccaggaagaca gaggcagcttcgttaccaccccactgcggagctgtccagccaggaggagacgctgctg ggcagcttcctcgactggagcctggactgctgctctggctatgaaggcgaccaggagag tgagggcgagaaggagggcgacgtgacagctcccagcggcatcctcgatgtcaccgtg gtctacctgaacccagaacagcattgctgccaggaatccagtgatgaggaggcttgtcca gaggacaagggaccccaggacccacaggcactggcgctggacacccagatccctgca acccctggacccaaaccctggtccgcaccagccgggagccagggaaggacgtcacga cctcagggtactcctccgtcagcaccgcaagtcccacaagctccgtggacggtggcttgg gggccctgccccaacctacctcagtgctgtccctggacagtgactcgcacacacagccct gccaccatcaggccaggaagtcatgtttacagtgtcgtcccccaagtccccggagagca gtgttcccagcaacaggtgaagcggataaacctatgcatacacagtgaggaggagga catgaacctgggccttgtgaggctgtaagtgtgtcagcacatttgccgcagtggatgtgta ctgaggggctggaggcgaagggtgggagcatagcataggaacgctgcatagaccat ggaggcctttgcgcagagagcagagaggatgacttgcggccaccaagtttctgtctccg cgggagtcccgtgcaagccatcagaatgttgaaatgagggtgaagagctcagatccctc tcttttggaaagtttagcctggaagcagttggccacactgtgtgagggcacctctctgtcc | 4 |

TABLE A-continued

DESCRIPTION OF THE SEQUENCES

| GenBank Accession No. | SEQUENCE | SEQ ID NO: |
|---|---|---|
| | cttccgtgtctcactgtctctggaagcttcagcccatgtgtgtcctggtgttcccagcccac<br>cagagccccgtgccgggagctgacagcttttcacgcttaaggcacgtgtgacctgggtagt<br>cagacaccacttgagcccctgcccacatctgctggtttggggcttcagtggggagctgac<br>agctgtgagcacaccactgtcccctcatccacctcggcctgcatggggcacccacttcctt<br>ctgggtggggcttccatggtaaggggggcctgcgtccctgcacactgcgaggactgccttg<br>gccacaggcccactccctacgacacgtgactcgttttagagctctgtcccagaggcgttcg<br>tatgtgacccacagatggcgtcaatgtgaacacctctctttgtgctgaatttctgggccatt<br>cttttcctgtcttatttctaaatttccttcttccaagatgaaaacaaaagaaaaacttaaaac<br>agaaggtattaaaaaaacaagagattccaccattatttaggttcacctgcaaaacaaaa<br>atcttactccagccctcaatgccatcctgacacactttatgcaaaaagaattttcccagat<br>aggctagccagaaaaaacttcaagtcctctgtaacatctgaggtgaccaagaggcagaa<br>gagcagagcagtcgggggccgtgtcctggctgatcccaactgcagctctgctgtggggg<br>cccgtgggagggaggcagaccctgggcttctgctggccacggagactctgctcctgc<br>atggaaagggagcctgggagccagcagcccacgcctggggagcctgcctggggccat<br>gtgaccatggcctctccctgggaacgggctgaccacaacacacccctgctgccatccacttc<br>tgtttactctgcaaatgtaagaaagaaccacttggccagaagtgtccccagatgcttttt<br>tttttttttttgggagacagttttgctcttgtctccccggctggagtgcagtggcatgatctca<br>actctcaactcactgtaacctccgcctcccggatactcctgcctcagcctcctgggtagctg<br>ggattacaagcacccaaccacgcccagctaattttgtattttcggtagagacgggatttc<br>accatgttggccaggctagtctcgaactcatgacctcaagtgatccgcccacttcggtctc<br>ccaaagtgctgggattacaggcatgagccacggcgctggcccccaaatgctcttgaac<br>cggaaacccagggatgggagatgctcactgagctgctgcttttatgtgtgctggtgctatg<br>tgtgttcatgtccgcggcagctgtcttttttgctactataagggaattctggccaccctgggt<br>ggggtgtggtcggggtgagaacccaagcgttggaactgtagacccgtcctgtcgactgt<br>gtgcccctgggcatgtgtgagcctcagtttcctcatctgtaaggggggcaatgatacctac<br>ctcacaggggtgttgtgaggattaaatgtgaggaggatagtggcaaaaaaaaaaaaa<br>aaaa | |
| NM_001323538 CDS | atgaggtacattctgatcgactggctggtggaagttgccaccatgaaggacttcacaagc<br>ctgtgcctgcacctgaccgtggagtgtgtggaccggtacctgcggaggaggctggtgcc<br>gcggtacaggctccagctgctgggcatcgcctgcatggtcatctgcacccggtttatcagt<br>aaagagatcctgaccatccgggaggccgtatggctcacggacaacacttacaagtacga<br>ggacctggtgagaatgatgggcgagatcgtctccgccttggaagggaagattcgagtcc<br>ccactgtggtggattacaaggaggtcctgctgacgctagtccctgtggagctgagaaccc<br>agcacctgtgcagcttcctctgcgagctctccctgctgcacaccagcctgtccgcctacgcc<br>ccagcccgcctggctgccgcagccctgctcctggccagactgacgcacggcagacaca<br>gccctggaccactcagctgtgggacctcaccggattctcctatgaagacctcattccctgc<br>gtcttgagcctccataagaagtgcttccatgatgacgccccaaggactacaggcaagtc<br>tctctgaccgccgtgaagcagcggtttgaggacaagcgctatgagaaatcagccagg<br>aagaggtgctgagctacagccagttgtgtgctgcattaggagtgacacaagacagcccc<br>gacccccgactttcctcagcacaggggagatccacgccttcctcagctctccctcggggc<br>ggagaaccaaacgaagcgggagaacagcctccaggaagacagaggcagcttcgtta<br>ccaccccactgcggagctgtccagccaggaggagacgctgctgggcagcttcctcgac<br>tggagcctggactgctgctctggctatgaaggcgaccaggagagtgaggggcgagaagg<br>agggcgacgtgacagctcccagcggcatcctcgatgtcaccgtggtctacctgaaccca<br>gaacagcattgctgccaggaatccagtgatgaggaggcttgtccagaggacaagggac<br>cccaggacccacaggcactggcgctggacacccagatccctgcaaccctggacccaaa<br>cccctggtccgcaccagccgggagccaggggaaggacgtcacgacctcagggtactcctc<br>cgtcagcaccgcaagtcccacaagctccgtggacggtggcttgggggccctgccccaac<br>ctacctcagtgctgtccctggacagtgactcgcacacacagccctgccaccatcaggcca<br>ggaagtcatgtttacagtgtcgtcccccaagtccccggagagcagtgttcccagcaac<br>aggtgaagcggataaacctatgcatacacagtgaggaggaggacatgaacctgggcct<br>tgtgaggctgtaa | 5 |
| NP_001310467 | MRYILIDWLVEVATMKDFTSLCLHLTVECVDRYLRRRLVPRYRLQLLGI<br>ACMVICTRFISKEILTIREAVWLTDNTYKYEDLVRMMGEIVSALEGKIRV<br>PTVVDYKEVLLTLVPVELRTQHLCSFLCELSLLHTSLSAYAPARLAAAAL<br>LLARLTHGQTQPWTTQLWDLTGFSYEDLIPCVLSLHKKCFHDDAPKDY<br>RQVSLTAVKQRFEDKRYGEISQEEVLSYSQLCAALGVTQDSPDPPTFLS<br>TGEIHAFLSSPSGRRTKRKRENSLQEDRGSFVTTPTAELSSQEETLLGS<br>FLDWSLDCCSGYEGDQESEGEKEGDVTAPSGILDVTVVYLNPEQHCC<br>QESSDEEACPEDKGPQDPQALALDTQIPATPGPKPLVRTSREPGKDVT<br>TSGYSSVSTASPTSSVDGGLGALPQPTSVLSLDSDSHTQPCHHQARK<br>SCLQCRPPSPPESSVPQQQVKRINLCIHSEEEDMNLGLVRL | 6 |

DETAILED DESCRIPTION OF THE INVENTION

1. Definitions

Unless defined otherwise, all technical and scientific terms used herein have the same meaning as commonly understood by those of ordinary skill in the art to which the invention belongs. Further, unless otherwise required by context, singular terms shall include pluralities and plural terms shall include the singular. Although any methods and materials similar or equivalent to those described herein can be used in the practice or testing of the present invention, preferred methods and materials are described. For the purposes of the present invention, the following terms are defined below.

The singular terms "a", "an" and "the" include plural referents unless context clearly indicates otherwise. It is further to be understood that all base sizes or amino acid sizes, and all molecular weight or molecular mass values, given for nucleic acids or polypeptides are approximate, and are provided for description.

As used herein, "and/or" refers to and encompasses any and all possible combinations of one or more of the associated listed items, as well as the lack of combinations when interpreted in the alternative (or).

Further, the terms "about" and "approximate", as used herein when referring to a measurable value such as an amount, dose, time, temperature, activity, level, number, frequency, percentage, dimension, size, amount, weight, position, length and the like, is meant to encompass variations of ±15%, ±10%, ±5%, ±1%, ±0.5%, or even ±0.1% of the specified amount, dose, time, temperature, activity, level, number, frequency, percentage, dimension, size, amount, weight, position, length and the like.

The term "activity" as used herein shall be understood as a measure for the ability of a transcription product or a translation product to produce a biological effect or a measure for a level of biologically active molecules. Accordingly, in the context of cyclin F, the term "activity" refers to any one or more of the following activities: (1) associating with other subunits to form a Skp1-Cul1-F-box (SCF) E3 ubiquitin-protein ligase complex ($SCF^{Cyclin\ F}$); (2) suppressing B-Myb activity to promote cell cycle checkpoint control; and (3) interacting with a substrate (e.g., CDC6, RRM2, CP110, and SLBP, as well as TDP-43, as disclosed herein) to promote ubiquitylation and degradation of the substrate.

As used herein, the term "administered" refers to the placement of an agent described herein, into a subject by a method or route which results in at least partial localization of the compound at a desired site. An agent described herein can be administered by any appropriate route which results in effective treatment in the subject, i.e., administration results in delivery to a desired location in the subject where at least a portion of the composition delivered. Exemplary modes of administration include, but are not limited to, injection, infusion, instillation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebrospinal, and intrasternal injection and infusion.

The terms "administration concurrently" or "administering concurrently" or "co-administering" and the like refer to the administration of a single composition containing two or more actives, or the administration of each active as separate compositions and/or delivered by separate routes either contemporaneously or simultaneously or sequentially within a short enough period of time that the effective result is equivalent to that obtained when all such actives are administered as a single composition. By "simultaneously" is meant that the active agents are administered at substantially the same time, and desirably together in the same formulation. By "contemporaneously" it is meant that the active agents are administered closely in time, e.g., one agent is administered within from about one minute to within about one day before or after another. Any contemporaneous time is useful. However, it will often be the case that when not administered simultaneously, the agents will be administered within about one minute to within about eight hours and suitably within less than about one to about four hours. When administered contemporaneously, the agents are suitably administered at the same site on the subject. The term "same site" includes the exact location, but can be within about 0.5 to about 15 centimeters, preferably from within about 0.5 to about 5 centimeters. The term "separately" as used herein means that the agents are administered at an interval, for example at an interval of about a day to several weeks or months. The active agents may be administered in either order. The term "sequentially" as used herein means that the agents are administered in sequence, for example at an interval or intervals of minutes, hours, days or weeks. If appropriate the active agents may be administered in a regular repeating cycle.

The term "agent" or "modulatory agent" includes a compound that induces a desired pharmacological and/or physiological effect. The term also encompass pharmaceutically acceptable and pharmacologically active ingredients of those compounds specifically mentioned herein including but not limited to salts, esters, amides, prodrugs, active metabolites, analogs and the like. When the above term is used, then it is to be understood that this includes the active agent per se as well as pharmaceutically acceptable, pharmacologically active salts, esters, amides, prodrugs, metabolites, analogs, etc. The term "agent" is not to be construed narrowly but extends to small molecules, proteinaceous molecules such as peptides, polypeptides and proteins as well as compositions comprising them and genetic molecules such as RNA, DNA and mimetics and chemical analogs thereof as well as cellular agents. The term "agent" includes a cell that is capable of producing and secreting a polypeptide referred to herein as well as a polynucleotide comprising a nucleotide sequence that encodes that polypeptide. Thus, the term "agent" extends to nucleic acid constructs including vectors such as viral or non-viral vectors, expression vectors and plasmids for expression in and secretion in a range of cells. As used herein, the terms "candidate agent" and "test agent" are used interchangeably to refer to agents and/or compositions that are to be screened for their ability to stimulate and/or increase and/or promote motor neuron survival, and/or to inhibit or reduce motor neuron degeneration, and/or to inhibit or reduce abnormal protein accumulation in motor neurons.

As used herein, an "agent that enhances the level or activity of cyclin F" refers to an agent that increases the level of cyclin F mRNA or protein, an activity of cyclin F, the half-life of cyclin F mRNA or protein, or the binding of cyclin F to another molecule (e.g., a substrate for cyclin F such as TDP-43 and/or other components of the $SCF^{Cyclin\ F}$ complex). For example, the agent may directly or indirectly enhance the ability of cyclin F to associate with other components of the $SCF^{Cyclin\ F}$ complex and ubiquitinate proteins for clearance by the proteasome. Expression levels of mRNA can be determined using standard RNase protection assays or in situ hybridization assays, and the level of protein can be determined using standard Western or immunohistochemistry analysis. The ubiquitination level of a protein can also be measured using standard assays. In some embodiments, an agent that enhances the level or activity of cyclin F increases cyclin F activity by at least 20, 40, 60, 80, or 90%. In some embodiments, the level of cyclin F is at least 2, 3, 5, 10, 20, or 50-fold higher in the presence of the cyclin F-enhancing agent.

The terms "cis-acting element", "cis-acting sequence" or "cis-regulatory region" are used interchangeably herein to mean any sequence of nucleotides, which modulates transcriptional activity of an operably linked promoter and/or expression of an operably linked nucleotide sequence. Those skilled in the art will be aware that a cis-sequence may be capable of activating, silencing, enhancing, repressing or otherwise altering the level of expression and/or cell-type-specificity and/or developmental specificity of any nucleotide sequence, including coding and non-coding sequences.

By "coding sequence" is meant any nucleic acid sequence that contributes to the code for the polypeptide product of a gene or for the final mRNA product of a gene (e.g. the mRNA product of a gene following splicing). By contrast, the term "non-coding sequence" refers to any nucleic acid sequence that does not contribute to the code for the polypeptide product of a gene or for the final mRNA product of a gene.

As used herein, a "companion diagnostic" refers to a diagnostic method and or reagent that is used to identify subjects susceptible to treatment with a particular treatment or to monitor treatment and/or to identify an effective dosage for a subject or sub-group or other group of subjects. For purposes herein, a companion diagnostic refers to reagents, such as a reagent for determining the level or activity of cyclin F (e.g., as described herein) in a sample. The companion diagnostic refers to the reagents and also to the test(s) that is/are performed with the reagent.

Throughout this specification, unless the context requires otherwise, the words "comprise," "comprises" and "comprising" will be understood to imply the inclusion of a stated step or element or group of steps or elements but not the exclusion of any other step or element or group of steps or elements. Thus, use of the term "comprising" and the like indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

As used herein, the term "condition" includes anatomic and physiological deviations from the normal that constitute an impairment of the normal state of the living animal or one of its parts, that interrupts or modifies the performance of the bodily functions.

The terms "conditional expression", "conditionally expressed" "conditionally expressing" and the like refer to the ability to activate or suppress expression of a gene of interest by the presence or absence of a stimulus or other signal (e.g., chemical, light, hormone, stress, or a pathogen). In specific embodiments, conditional expression of a nucleic acid sequence of interest is dependent on the presence of an inducer or the absence of an inhibitor.

A "conservative amino acid substitution" is one in which the amino acid residue is replaced with an amino acid residue having a similar side chain. Families of amino acid residues having similar side chains have been defined in the art, which can be generally sub-classified as follows:

TABLE 1

AMINO ACID SUB-CLASSIFICATION

| Sub-classes | Amino acids |
| --- | --- |
| Acidic | Aspartic acid, Glutamic acid |
| Basic | Noncyclic: Arginine, Lysine; Cyclic: Histidine |
| Charged | Aspartic acid, Glutamic acid, Arginine, Lysine, Histidine |
| Small | Glycine, Serine, Alanine, Threonine, Proline |
| Polar/neutral | Asparagine, Histidine, Glutamine, Cysteine, Serine, Threonine |
| Polar/large | Asparagine, Glutamine |
| Hydrophobic | Tyrosine, Valine, Isoleucine, Leucine, Methionine, Phenylalanine, Tryptophan |
| Aromatic | Tryptophan, Tyrosine, Phenylalanine |
| Residues that influence chain orientation | Glycine and Proline |

Conservative amino acid substitution also includes groupings based on side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. For example, it is reasonable to expect that replacement of a leucine with an isoleucine or valine, an aspartate with a glutamate, a threonine with a serine, or a similar replacement of an amino acid with a structurally related amino acid will not have a major effect on the properties of the resulting variant polypeptide. Whether an amino acid change results in a functional polypeptide can readily be determined by assaying its activity. Conservative substitutions are shown in Table 2 under the heading of exemplary and preferred substitutions. Amino acid substitutions falling within the scope of the invention, are, in general, accomplished by selecting substitutions that do not differ significantly in their effect on maintaining (a) the structure of the peptide backbone in the area of the substitution, (b) the charge or hydrophobicity of the molecule at the target site, or (c) the bulk of the side chain. After the substitutions are introduced, the variants are screened for biological activity.

TABLE 2

EXEMPLARY AND PREFERRED AMINO ACID SUBSTITUTIONS

| Original Residue | Exemplary Substitutions | Preferred Substitutions |
| --- | --- | --- |
| Ala | Val, Leu, Ile | Val |
| Arg | Lys, Gln, Asn | Lys |
| Asn | Gln, His, Lys, Arg | Gln |
| Asp | Glu | Glu |
| Cys | Ser | Ser |
| Gln | Asn, His, Lys, | Asn |
| Glu | Asp, Lys | Asp |
| Gly | Pro | Pro |
| His | Asn, Gln, Lys, Arg | Arg |
| Ile | Leu, Val, Met, Ala, Phe, Norleu | Leu |
| Leu | Norleu, Ile, Val, Met, Ala, Phe | Ile |
| Lys | Arg, Gln, Asn | Arg |
| Met | Leu, Ile, Phe | Leu |
| Phe | Leu, Val, Ile, Ala | Leu |
| Pro | Gly | Gly |
| Ser | Thr | Thr |

TABLE 2-continued

EXEMPLARY AND PREFERRED AMINO ACID SUBSTITUTIONS

| Original Residue | Exemplary Substitutions | Preferred Substitutions |
|---|---|---|
| Thr | Ser | Ser |
| Trp | Tyr | Tyr |
| Tyr | Trp, Phe, Thr, Ser | Phe |
| Val | Ile, Leu, Met, Phe, Ala, Norleu | Leu |

The term "contacting" or "contact" as used herein in connection with contacting a motor neuron or motor neuron surrogate cell includes subjecting the motor neuron or surrogate cell to an appropriate culture media which comprises the indicated compound and/or agent. Where the motor neuron or surrogate cell is in vivo, "contacting" or "contact" includes administering the compound and/or agent in a pharmaceutical composition to a subject via an appropriate administration route such that the compound and/or agent contacts the motor neuron or surrogate cell in vivo. In specific embodiments, the contacted motor neuron or surrogate cell are assayed for cell survival. Measurement of cell survival can be based on the number of viable cells after period of time has elapsed after contacting of cells with a compound or agent. For example, number of viable cells can be counted after about at least 5 minutes, 10 minutes, 20 minutes, 30 minutes, 40 minutes, 50 minutes, 1 hour, 2 hours, 4 hours, 6 hours, 12 hours, 24 hours, 2 days, 3 days or more and compared to number of viable cells in a non-treated control.

The term "construct" refers to a recombinant genetic molecule including one or more isolated nucleic acid sequences from different sources. Thus, constructs are chimeric molecules in which two or more nucleic acid sequences of different origin are assembled into a single nucleic acid molecule and include any construct that contains (1) nucleic acid sequences, including regulatory and coding sequences that are not found together in nature (i.e., at least one of the nucleotide sequences is heterologous with respect to at least one of its other nucleotide sequences), or (2) sequences encoding parts of functional RNA molecules or proteins not naturally adjoined, or (3) parts of promoters that are not naturally adjoined. Representative constructs include any recombinant nucleic acid molecule such as a plasmid, cosmid, virus, autonomously replicating polynucleotide molecule, phage, or linear or circular single stranded or double stranded DNA or RNA nucleic acid molecule, derived from any source, capable of genomic integration or autonomous replication, comprising a nucleic acid molecule where one or more nucleic acid molecules have been operably linked. Constructs of the present invention will generally include the necessary elements to direct expression of a nucleic acid sequence of interest that is also contained in the construct, such as, for example, a target nucleic acid sequence or a modulator nucleic acid sequence. Such elements may include control elements such as a promoter that is operably linked to (so as to direct transcription of) the nucleic acid sequence of interest, and often includes a polyadenylation sequence as well. Within certain embodiments of the invention, the construct may be contained within a vector. In addition to the components of the construct, the vector may include, for example, one or more selectable markers, one or more origins of replication, such as prokaryotic and eukaryotic origins, at least one multiple cloning site, and/or elements to facilitate stable integration of the construct into the genome of a host cell. Two or more constructs can be contained within a single nucleic acid molecule, such as a single vector, or can be containing within two or more separate nucleic acid molecules, such as two or more separate vectors. An "expression construct" generally includes at least a control sequence operably linked to a nucleotide sequence of interest. In this manner, for example, promoters in operable connection with the nucleotide sequences to be expressed are provided in expression constructs for expression in an organism or part thereof including a host cell. For the practice of the present invention, conventional compositions and methods for preparing and using constructs and host cells are well known to one skilled in the art, see for example, Molecular Cloning: A Laboratory Manual, $3^{rd}$ edition Volumes 1, 2, and 3. J. F. Sambrook, D. W. Russell, and N. Irwin, Cold Spring Harbor Laboratory Press, 2000.

The term "control motor neuron" as used herein means a motor neuron from one or more subjects not having a neurodegenerative condition (e.g., control subjects).

By "corresponds to" or "corresponding to" is meant an amino acid sequence that displays substantial sequence similarity or identity to a reference amino acid sequence. In general the amino acid sequence will display at least about 70, 71, 72, 73, 74, 75, 76, 77, 78, 79, 80, 81, 82, 83, 84, 85, 86, 97, 88, 89, 90, 91, 92, 93, 94, 95, 96, 97, 98, 99% or even up to 100% sequence similarity or identity to at least a portion of the reference amino acid sequence.

The terms "decrease", "reduce" or "inhibit" and their grammatical equivalents are all used herein generally to mean a decrease by a statistically significant amount. However, for avoidance of doubt, the terms "decrease", "reduce" or "inhibit" and their grammatical equivalents mean a decrease by at least 10% as compared to a reference level, for example a decrease by at least about 20%, or at least about 30%, or at least about 40%, or at least about 50%, or at least about 60%, or at least about 70%, or at least about 80%, or at least about 90%, where the decrease is less than 100%. In one embodiment, the decrease includes a 100% decrease (e.g. absent level as compared to a reference sample), or any decrease between 10-100% as compared to a reference level.

As used herein, the term "detectable label" refers to a molecule or an element or functional group in a molecule that allows for the detection, imaging, and/or monitoring of the presence the molecule. Without limitations, a detectable label can be an echogenic substance (either liquid or gas), non-metallic isotope, an optical reporter, a boron neutron absorber, a paramagnetic metal ion, a ferromagnetic metal, a gamma-emitting radioisotope, a positron-emitting radioisotope, or an x-ray absorber.

A "detectable response" generally refers to a change in, or occurrence of, a signal that is detectable either by observation or instrumentally. In certain instances, the detectable response is fluorescence or a change in fluorescence, e.g., a change in fluorescence intensity, fluorescence excitation or emission wavelength distribution, fluorescence lifetime, and/or fluorescence polarization.

As used herein, the terms "diagnosis," "diagnosing" and the like are used interchangeably herein to encompass determining the likelihood that a subject will develop a condition, or the existence or nature of a condition in a subject. These terms also encompass determining the severity of disease or episode of disease, as well as in the context of rational therapy, in which the diagnosis guides therapy, including initial selection of therapy, modification of therapy (e.g., adjustment of dose or dosage regimen), and the like.

By "likelihood" is meant a measure of whether a subject with particular measured or derived biomarker values actually has a condition (or not) based on a given mathematical model. An increased likelihood for example may be relative or absolute and may be expressed qualitatively or quantitatively. For instance, an increased likelihood may be determined simply by determining the subject's measured cyclin F level or activity and placing the subject in an "increased likelihood" category, based upon previous population studies. The term "likelihood" is also used interchangeably herein with the term "probability". The term "risk" relates to the possibility or probability of a particular event occurring at some point in the future. "Risk stratification" refers to an arraying of known clinical risk factors to allow physicians to classify patients into a low, moderate, high or highest risk of developing a particular disease.

As used herein, "dosage unit" refers to physically discrete units suited as unitary dosages for the subject to be treated; each unit containing a predetermined quantity of agent calculated to produce the desired therapeutic effect in association with the required pharmaceutical carrier.

As used herein, the term "effective amount" means an amount of the compound and/or agent which is effective to promote the survival of motor neuron cells or to prevent or slow the death of such cells. Determination of a therapeutically effective amount is well within the capability of those skilled in the art. Generally, a therapeutically effective amount can vary with the subject's history, age, condition, sex, as well as the severity and type of the medical condition in the subject, and administration of other agents that inhibit pathological processes in neurodegenerative conditions.

As used herein, the terms "encode", "encoding" and the like refer to the capacity of a nucleic acid to provide for another nucleic acid or a polypeptide. For example, a nucleic acid sequence is said to "encode" a polypeptide if it can be transcribed and/or translated to produce the polypeptide or if it can be processed into a form that can be transcribed and/or translated to produce the polypeptide. Such a nucleic acid sequence may include a coding sequence or both a coding sequence and a non-coding sequence. Thus, the terms "encode", "encoding" and the like include a RNA product resulting from transcription of a DNA molecule, a protein resulting from translation of a RNA molecule, a protein resulting from transcription of a DNA molecule to form a RNA product and the subsequent translation of the RNA product, or a protein resulting from transcription of a DNA molecule to provide a RNA product, processing of the RNA product to provide a processed RNA product (e.g., mRNA) and the subsequent translation of the processed RNA product.

The term "expression" with respect to a gene sequence refers to transcription of the gene to produce a RNA transcript (e.g., mRNA, antisense RNA, siRNA, shRNA, miRNA, etc.) and, as appropriate, translation of a resulting mRNA transcript to a protein. Thus, as will be clear from the context, expression of a coding sequence results from transcription and translation of the coding sequence. Conversely, expression of a non-coding sequence results from the transcription of the non-coding sequence.

As used herein, the term "gene" refers to a nucleic acid molecule capable of being used to produce mRNA, antisense RNA, siRNA, shRNA, miRNA, and the like, and in some embodiments, polypeptide. Genes may or may not be capable of being used to produce a functional protein. Genes can include both coding and non-coding regions (e.g., introns, regulatory elements including promoters, enhancers, termination sequences and 5' and 3' untranslated regions). In certain embodiments, the term "gene" includes within its scope the open reading frame encoding specific polypeptides, introns, and adjacent 5' and 3' non-coding nucleotide sequences involved in the regulation of expression. In this regard, the gene may further comprise control sequences such as promoters, enhancers, termination and/or polyadenylation signals that are naturally associated with a given gene, or heterologous control sequences. The gene sequences may be cDNA or genomic DNA or a fragment thereof. The gene may be introduced into an appropriate vector for extrachromosomal maintenance or for introduction into a host.

The terms "increase", "enhance", or "activate" and their grammatical equivalents are all used herein to generally mean an increase by a statically significant amount; for the avoidance of any doubt, the terms "increase", "enhance", or "activate" and their grammatical equivalents mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

As used herein, the phrase "inhibiting motor neuron degeneration" refers to reducing loss of motor neuron viability, reducing loss of motor neuron function and/or reducing loss of the number of motor neurons. In some embodiments, contacting of a motor neuron with an agent described herein results in at least about 10%, 20%, 30%, 40%, 50% 60%, 70%, 80%, 90%, 95%, 100%, 2-fold, 3-fold, 4-fold, 5-fold or more decrease in motor neuron degeneration relative to non-treated control. Motor neuron degeneration can be assessed by for example by assaying oxidative stress or endoplasmic reticulum stress or apoptosis or neuronal death in general.

The term "level" as used herein encompasses the absolute amount of cyclin F, the relative amount or concentration of cyclin F as well as any value or parameter which correlates thereto or can be derived therefrom. For example, the level can be weight, moles, abundance, concentration such as µg/L or a relative amount such as 9/10, 4/5, 7/10, 3/5, 7/10, 2/5, 3/10, 1/5, 1/10, 1/20, 1/50, $10^{-1}$, $10^{-2}$, $10^{-3}$, $10^{-4}$, $10^{-5}$, $10^{-6}$, $10^{-7}$, $10^{-8}$, $10^{-9}$, $10^{-10}$, $10^{-11}$, 10–12, $10^{-13}$, $10^{-14}$ or about $10^{-15}$ of a reference or control level. Optionally, the term level includes the level of cyclin F normalized to an internal normalization control, such as the expression of a housekeeping gene.

The term "level" as applied to the level of cyclin F includes within its scope the level of a CCNF transcript product (e.g., CCNF mRNA) and/or a CCNF translation product (e.g., cyclin F).

The terms "level" and/or "activity" as used herein further refer to gene expression levels or gene activity. Gene expression can be defined as the utilization of the information contained in a gene by transcription and translation leading to the production of a gene product. The measured "expression level" is an indicator for the amount of transcription or translation product produced.

As used herein, the term "modulate" means to cause or facilitate a qualitative or quantitative change, alteration, or modification in a molecule, a process, pathway, or phenomenon of interest. Without limitation, such change may be an increase, decrease, a change in binding characteristics, or change in relative strength or activity of different components or branches of the process, pathway, or phenomenon.

The term "modulator" refers to any molecule or compound that causes or facilitates a qualitative or quantitative change, alteration, or modification in a process, pathway, or phenomenon of interest. As used herein, the term "modulator" comprises both inhibitors and activators of a biological pathway or target.

As used herein, the phrase "motor neuron degeneration" or "degeneration of motor neuron" means a condition of deterioration of motor neurons, wherein the neurons die or change to a lower or less functionally-active form.

The term "neurodegenerative condition" is an inclusive term encompassing acute and chronic conditions, disorders or diseases of the central or peripheral nervous system and is generally caused by or associated with the deterioration of cells or tissues of the nervous system. A neurodegenerative condition may be age-related, or it may result from injury or trauma, or it may be related to a specific disease or disorder. Acute neurodegenerative conditions include, but are not limited to, conditions associated with neuronal cell death or compromise including cerebrovascular insufficiency, focal or diffuse brain trauma, diffuse brain damage, spinal cord injury or peripheral nerve trauma, e.g., resulting from physical or chemical burns, deep cuts or limb severance. Examples of acute neurodegenerative disorders are: cerebral ischemia or infarction including embolic occlusion and thrombotic occlusion, reperfusion following acute ischemia, perinatal hypoxic-ischemic injury, cardiac arrest, as well as intracranial hemorrhage of any type (such as epidural, subdural, subarachnoid and intracerebral), and intracranial and intravertebral lesions (such as contusion, penetration, shear, compression and laceration), as well as whiplash and shaken infant syndrome. Chronic neurodegenerative conditions include, but are not limited to, Alzheimer's disease, diffuse Lewy body disease, progressive supranuclear palsy (Steel-Richardson syndrome), multisystem degeneration (Shy-Drager syndrome), chronic epileptic conditions associated with neurodegeneration, motor neuron diseases including amyotrophic lateral sclerosis (ALS), frontotemporal dementia (FTD), degenerative ataxias, cortical basal degeneration, ALS-Parkinson's-Dementia complex of Guam, subacute sclerosing panencephalitis, Huntington's disease, Parkinson's disease, synucleinopathies (including multiple system atrophy), primary progressive aphasia, striatonigral degeneration, Machado-Joseph disease/spinocerebellar ataxia type 3 and olivopontocerebellar degenerations, Gilles De La Tourette's disease, bulbar and pseudobulbar palsy, spinal and spinobulbar muscular atrophy (Kennedy's disease), primary lateral sclerosis, familial spastic paraplegia, Werdnig-Hoffmann disease, Kugelberg-Welander disease, Tay-Sach's disease, Sandhoff disease, familial spastic disease, Wohlfart-Kugelberg-Welander disease, spastic paraparesis, progressive multifocal leukoencephalopathy, familial dysautonomia (Riley-Day syndrome), and prion diseases (including, but not limited to Creutzfeldt-Jakob, Gerstmann-Straussler-Scheinker disease, Kuru and fatal familial insomnia), demyelination diseases and disorders including multiple sclerosis and hereditary diseases such as Leukodystrophies. In specific embodiments, the neurodegenerative condition is selected from ALS and FTD.

The term "neurotropic viral vector" refers to a viral vector that selectively infects neuronal cells, including motor neurons.

By "obtained" is meant to come into possession. Samples so obtained include, for example, nucleic acid extracts or polypeptide extracts isolated or derived from a particular source. For instance, the extract may be isolated directly from a biological fluid or tissue of a subject.

The term "operably connected" or "operably linked" as used herein refers to a juxtaposition wherein the components so described are in a relationship permitting them to function in their intended manner. For example, a regulatory sequence (e.g., a promoter) "operably linked" to a nucleotide sequence of interest (e.g., a coding and/or non-coding sequence) refers to positioning and/or orientation of the control sequence relative to the nucleotide sequence of interest to permit expression of that sequence under conditions compatible with the control sequence. The control sequences need not be contiguous with the nucleotide sequence of interest, so long as they function to direct its expression. Thus, for example, intervening non-coding sequences (e.g., untranslated, yet transcribed, sequences) can be present between a promoter and a coding sequence, and the promoter sequence can still be considered "operably linked" to the coding sequence.

The terms "overexpress," "overexpression," or "overexpressed" interchangeably refer to a gene (e.g., a TDP-43 gene) that is transcribed or translated at a detectably greater level in comparison to a normal cell (e.g., a normal motor neuron). Overexpression therefore refers to both overexpression of protein and RNA (due to increased transcription, post transcriptional processing, translation, post translational processing, altered stability, and altered protein degradation), as well as local overexpression due to altered protein traffic patterns (increased nuclear localization), and augmented functional activity, e.g., as in an increased enzyme hydrolysis of substrate. Overexpression can also be by 10%, 20%, 30%, 40%, 50%, 60%, 70%, 80%, 90% or more in comparison to a normal cell or comparison cell (e.g., a normal motor neuron).

The terms "patient", "subject", "host" or "individual" used interchangeably herein, refer to any subject, particularly a vertebrate subject, and even more particularly a mammalian subject, for whom therapy or prophylaxis is desired. Suitable vertebrate animals that fall within the scope of the invention include, but are not restricted to, any member of the subphylum Chordata including primates (e.g., humans, monkeys and apes, and includes species of monkeys such from the genus *Macaca* (e.g., cynomologus monkeys such as *Macaca fascicularis*, and/or rhesus monkeys (*Macaca mulatta*)) and baboon (*Papio ursinus*), as well as marmosets (species from the genus *Callithrix*), squirrel monkeys (species from the genus *Saimiri*) and tamarins (species from the genus *Saguinus*), as well as species of apes such as chimpanzees (*Pan troglodytes*)), rodents (e.g., mice rats, guinea pigs), lagomorphs (e.g., rabbits, hares), bovines (e.g., cattle), ovines (e.g., sheep), caprines (e.g., goats), porcines (e.g., pigs), equines (e.g., horses), canines (e.g., dogs), felines (e.g., cats), avians (e.g., chickens, turkeys, ducks, geese, companion birds such as canaries, budgerigars etc.), marine mammals (e.g., dolphins, whales), reptiles (snakes, frogs, lizards etc.), and fish. A preferred subject is a human in need of increasing the level or activity of cyclin F and/or treatment of a neurodegenerative condition. However, it will be understood that the aforementioned terms do not imply that symptoms are present.

As used here, the term "pharmaceutically acceptable refers to those compounds, agents, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject agent from one organ, or portion of the body, to another organ, or portion of the body. Each carrier must be "acceptable" in the sense of being compatible with the other ingredients of the formulation and not injurious to the patient.

The term "polynucleotide" is used herein interchangeably with "nucleic acid" to indicate a polymer of nucleosides. Typically, a polynucleotide of this invention is composed of nucleosides that are naturally found in DNA or RNA (e.g., adenosine, thymidine, guanosine, cytidine, uridine, deoxyadenosine, deoxythymidine, deoxyguanosine, and deoxycytidine) joined by phosphodiester bonds. However, the term encompasses molecules comprising nucleosides or nucleoside analogs containing chemically or biologically modified bases, modified backbones, etc., whether or not found in naturally occurring nucleic acids, and such molecules may be preferred for certain applications. Where this application refers to a polynucleotide it is understood that both DNA, RNA, and in each case both single- and double-stranded forms (and complements of each single-stranded molecule) are provided. "Polynucleotide sequence" as used herein can refer to the polynucleotide material itself and/or to the sequence information (e.g. The succession of letters used as abbreviations for bases) that biochemically characterizes a specific nucleic acid. A polynucleotide sequence presented herein is presented in a 5' to 3' direction unless otherwise indicated.

The terms "polypeptide" as used herein refers to a polymer of amino acids. The terms "protein" and "polypeptide" are used interchangeably herein. A peptide is a relatively short polypeptide, typically between about 2 and 60 amino acids in length. Polypeptides used herein typically contain amino acids such as the 20 L-amino acids that are most commonly found in proteins. However, other amino acids and/or amino acid analogs known in the art can be used. One or more of the amino acids in a polypeptide may be modified, for example, by the addition of a chemical entity such as a carbohydrate group, a phosphate group, a fatty acid group, a linker for conjugation, functionalization, etc. A polypeptide that has a non-polypeptide moiety covalently or noncovalently associated therewith is still considered a "polypeptide". Exemplary modifications include glycosylation and palmitoylation. Polypeptides may be purified from natural sources, produced using recombinant DNA technology, synthesized through chemical means such as conventional solid phase peptide synthesis, etc. The term "polypeptide sequence" or "amino acid sequence" as used herein can refer to the polypeptide material itself and/or to the sequence information (e.g., the succession of letters or three letter codes used as abbreviations for amino acid names) that biochemically characterizes a polypeptide. A polypeptide sequence presented herein is presented in an N-terminal to C-terminal direction unless otherwise indicated.

The term "promoter" refers to a nucleotide sequence, usually upstream (5') to a transcribable sequence, which controls the expression of the transcribable sequence by providing the recognition for RNA polymerase and other factors required for proper transcription. "Promoter" includes a minimal promoter that is a short nucleic acid sequence comprised of a TATA-box and other sequences that serve to specify the site of transcription initiation, to which control elements (e.g., cis-acting elements) are added for control of expression. "Promoter" also refers to a nucleotide sequence that includes a minimal promoter plus control elements (e.g., cis-acting elements) that are capable of controlling the expression of a coding sequence or functional RNA. This type of promoter sequence consists of proximal and more distal upstream elements, the latter elements often referred to as enhancers. Accordingly, an "enhancer" is a nucleic acid sequence which can stimulate promoter activity and may be an innate element of the promoter or a heterologous element inserted to enhance the level or tissue specificity of a promoter. It is capable of operating in both orientations (normal or flipped), and is capable of functioning even when moved either upstream or downstream from the promoter. Both enhancers and other upstream promoter elements bind sequence-specific nucleic acid-binding proteins that mediate their effects. Promoters may be derived in their entirety from a native gene, or be composed of different elements derived from different promoters found in nature, or even be comprised of synthetic nucleic acid segments. A promoter may also contain nucleic acid sequences that are involved in the binding of protein factors which control the effectiveness of transcription initiation in response to physiological or developmental conditions. Promoter elements, particularly a TATA element, that are inactive or that have greatly reduced promoter activity in the absence of upstream activation are referred to as "minimal or core promoters." In the presence of a suitable transcription factor, the minimal promoter functions to permit transcription. A "minimal or core promoter" thus consists only of all basal elements needed for transcription initiation, e.g., a TATA box and/or an initiator.

As used herein, the phrase "promoting motor neuron survival" refers to an increase in survival of motor neuron cells as compared to a control. In some embodiments, contacting of a motor neuron with an agent described herein results in at least about 10%, 20%, 30%, 40%, 50% 60%, 70%, 80%, 90%, 95%, 100%, 2-fold, 3-fold, 4-fold, 5-fold or more increase in motor neuron survival relative to non-treated control. Motor neuron survival can be assessed by for example (i) increased survival time of motor neurons in culture; (ii) increased production of a neuron-associated molecule in culture or in vivo, e.g., choline acetyltransferase, acetylcholinesterase and cyclin F; (iii) reduced abnormal accumulation of proteins including TDP-43 in culture or in vivo; or (iv) decreased symptoms of motor neuron dysfunction in vivo. Such effects may be measured by any method known in the art. In one non-limiting example, increased survival of motor neurons may be measured by the method described by Arakawa et al. (1990, *J. Neurosci.* 10:3507-3515); increased production of neuron-associated molecules may be measured by bioassay, enzymatic assay, antibody binding, Northern blot assay, etc., depending on the molecule to be measured; reduced abnormal accumulation of proteins may be assayed through detection of aggregated proteins in aggresomes and inclusion bodies as described for example by Shen et al. (2011, *Cell Biochem Biophys* 60:173-185), and motor neuron dysfunction may be measured by assessing the physical manifestation of motor neuron disorder. In one embodiment, the increase in motor neuron survival can be assessed by measuring the increase in cyclin F levels. Cell survival can also be measured by uptake of calcein AM, an analog of the viable dye, fluorescein diacetate. Calcein is taken up by viable cells and cleaved intracellularly to fluorescent salts which are retained by intact membranes of viable cells. Microscopic counts of viable neurons correlate directly with relative fluorescence values obtained with the fluorometric viability assay. This method thus provides a reliable and quantitative measurement of cell survival in the total cell population of a given culture (Bozyczko-Coyne et al., J. Neur. Meth. 50:205-216, 1993). Other methods of assessing cell survival are described in U.S. Pat. Nos. 5,972,639; 6,077,684 and 6,417,160, contents of which are incorporated herein by reference. In vivo motor neuron survival can be assessed by an increase in motor neuron, neuromotor or neuromuscular function in a subject. In one non-limiting example, motor neuron survival in a subject can be assessed by reversion, alleviation, amelioration, inhibition, slowing down or stopping of the progression, aggravation or severity of a condition associated with motor neuron dysfunction or death in a subject, e.g., ALS or FTD.

The term "regulated promoter" refers to promoters that direct gene expression not constitutively, but in a temporally- and/or spatially-regulated manner, and include both tissue-specific and inducible promoters. It includes natural and synthetic sequences as well as sequences which may be a combination of synthetic and natural sequences. Different promoters may direct the expression of a gene in different tissues or cell types, or at different stages of development, or in response to different environmental conditions. New promoters of various types useful in host cells are constantly being discovered. Since in most cases the exact boundaries of regulatory sequences have not been completely defined, nucleic acid fragments of different lengths may have identical promoter activity. Illustrative regulated promoters include but are not limited to safener-inducible promoters, promoters derived from the tetracycline-inducible system, promoters derived from salicylate-inducible systems, promoters derived from alcohol-inducible systems, promoters derived from glucocorticoid-inducible systems, promoters derived from pathogen-inducible systems, promoters derived from carbohydrate inducible systems, promoters derived from hormone inducible systems, promoters derived from antibiotic inducible systems, promoters derived from metal inducible systems, promoters derived from heat shock inducible systems, and promoters derived from ecdysome-inducible systems.

"Regulatory sequences", "regulatory elements" and the like refer to nucleotide sequences located upstream (5' non-coding sequences), within, or downstream (3' non-coding sequences) of a coding sequence, and which influence the transcription, RNA processing or stability, or translation of the associated coding sequence, either directly or indirectly. Regulatory elements include enhancers, promoters, translation leader sequences, introns, Rep recognition element, intergenic regions and polyadenylation signal sequences. They include natural and synthetic sequences as well as sequences which may be a combination of synthetic and natural sequences.

The term "recombinant polynucleotide" as used herein refers to a polynucleotide formed in vitro by the manipulation of nucleic acid into a form not normally found in nature. For example, the recombinant polynucleotide may be in the form of an expression vector. Generally, such expression vectors include transcriptional and translational regulatory nucleic acid operably linked to the nucleotide sequence.

By "recombinant polypeptide" is meant a polypeptide made using recombinant techniques, i.e., through the expression of a recombinant polynucleotide.

The term "reduced level" as used herein with respect to the level of cyclin F in a motor neuron refers to any level of cyclin F that is below a median level for an age-matched random population of healthy subjects (e.g., an age-matched random population of 10, 20, 30, 40, 50, 100, or 500 healthy subjects) that do not have a neurodegenerative condition. In specific embodiments, a reduced level of cyclin F corresponds to a cyclin F level that is associated with one or both of the following: (1) abnormal localization of TDP-43 to a cellular compartment (e.g., the cytoplasm and/or nucleus); and (2) formation of abnormal TDP-43 structures (e.g., aggregates or inclusions comprising TDP-43). In certain embodiments, a reduced level or activity of cyclin F in a motor neuron is less than about 9/10, 4/5, 7/10, 3/5, 1/2, 2/5, 3/10, 1/5, 1/10, 1/20, 1/50, $10^{-1}$, $10^{-2}$, $10^{-3}$, $10^{-4}$, $10^{-5}$, $10^{-6}$, $10^{-7}$, $10^{-8}$, $10^{-9}$, $10^{-10}$, $10^{-11}$, $10^{-12}$, $10^{-13}$, $10^{-14}$ or about $10^{-15}$ of the level or activity of cyclin F in a control motor neuron.

As used herein, an "RNA interference molecule" refers to a compound which interferes with or inhibits expression of a target gene or genomic sequence by RNA interference (RNAi). Such RNA interfering agents include, but are not limited to, nucleic acid molecules including RNA molecules which are homologous to the target gene or genomic sequence, or a fragment thereof, short interfering RNA (siRNA), short hairpin or small hairpin RNA (shRNA), microRNA (miRNA) and small molecules which interfere with or inhibit expression of a target gene by RNA interference (RNAi).

The term "sample" as used herein includes any biological specimen that may be extracted, untreated, treated, diluted or concentrated from a subject. Samples may include, without limitation, biological fluids such as whole blood, serum, red blood cells, white blood cells, plasma, saliva, urine, stool (i.e., feces), tears, sweat, sebum, nipple aspirate, ductal lavage, tumor exudates, synovial fluid, ascitic fluid, peritoneal fluid, amniotic fluid, cerebrospinal fluid, lymph, fine needle aspirate, amniotic fluid, any other bodily fluid, cell lysates, cellular secretion products, inflammation fluid, semen and vaginal secretions. Samples may include tissue samples and biopsies, tissue homogenates and the like. In certain embodiments, the sample contains a tissue and in representative examples of this type, the sample is from a resection, biopsy, or core needle biopsy. In addition, fine needle aspirate samples can be used. Samples can include paraffin-embedded and frozen tissue. In specific embodiments, the sample comprises neuronal tissue, including motor neurons. In other embodiments, the sample comprises cells that are surrogates for motor neurons, non-limiting examples of which include fibroblasts, as disclosed for example by Yang et al. (2015, *Neurotox Res* 28:138-146) and blood cells, as disclosed for example in www.sciencedaily.com/releases/2014/04/140408121918.htm. The term "sample" also includes untreated or pretreated (or pre-processed) samples. In some embodiments, the sample is an untreated biological sample. The sample can be obtained by removing a sample of cells from a subject, but can also be accomplished by using previously isolated cells (e.g., isolated at a prior time point and isolated by the same or another person).

The term "sequence identity" as used herein refers to the extent that sequences are identical on a nucleotide-by-nucleotide basis or an amino acid-by-amino acid basis over a window of comparison. Thus, a "percentage of sequence identity" is calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. The present invention contemplates the use in the methods and systems of the present invention of full-length cyclin F polypeptides as well as their biologically active fragments. Typically, biologically active fragments of a full-length cyclin F polypeptide may participate in an interaction, for example, an intra-molecular or an inter-molecular interaction.

"Similarity" refers to the percentage number of amino acids that are identical or constitute conservative substitutions as defined in Tables 1 and 2 supra. Similarity may be determined using sequence comparison programs such as GAP (Deveraux et al. 1984, *Nucleic Acids Research* 12: 387-395). In this way, sequences of a similar or substantially different length to those cited herein might be compared by insertion of gaps into the alignment, such gaps being determined, for example, by the comparison algorithm used by GAP.

Terms used to describe sequence relationships between two or more polynucleotides or polypeptides include "reference sequence," "comparison window", "sequence identity," "percentage of sequence identity" and "substantial identity". A "reference sequence" is at least 12 but frequently 15 to 18 and often at least 25 monomer units, inclusive of nucleotides and amino acid residues, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, WI, USA) or by inspection and the best alignment (i.e., resulting in the highest percentage homology over the comparison window) generated by any of the various methods selected. Reference also may be made to the BLAST family of programs as for example disclosed by Altschul et al., 1997, *Nucl. Acids Res.* 25:3389. A detailed discussion of sequence analysis can be found in Unit 19.3 of Ausubel et al., "Current Protocols in Molecular Biology", John Wiley & Sons Inc, 1994-1998, Chapter 15.

As used herein, the term "small molecule" can refer to compounds that are "natural product-like", however, the term "small molecule" is not limited to "natural product-like" compounds. Rather, a small molecule is typically characterized in that it contains several carbon-carbon bonds, and has a molecular weight of less than 5000 Daltons (5 kDa), preferably less than 3 kDa, still more preferably less than 2 kDa, and most preferably less than 1 kDa. In some cases it is preferred that a small molecule have a molecular weight equal to or less than 700 Da.

The term "statistically significant" or "significantly" refers to statistical significance and generally means a two standard deviation (2SD) below normal, or lower, concentration of the marker. The term refers to statistical evidence that there is a difference. It is defined as the probability of making a decision to reject the null hypothesis when the null hypothesis is actually true. The decision is often made using the p-value.

As used herein, the terms "treatment", "treating", and the like, refer to obtaining a desired pharmacologic and/or physiologic effect. The effect may be prophylactic in terms of completely or partially preventing a disease or symptom thereof and/or may be therapeutic in terms of a partial or complete cure for a condition and/or adverse effect attributable to the condition. "Treatment", as used herein, covers any treatment of a condition in a mammal, particularly in a human, and includes: (a) preventing the condition from occurring in a subject which may be predisposed to the condition but has not yet been diagnosed as having it; (b) inhibiting the condition, i.e., arresting its development; and (c) relieving the condition, i.e., causing regression of the condition. Thus, "treatment of a neurodegenerative condition" includes within its scope delaying or preventing the onset of such a condition (e.g. death of motor neurons), at reversing, alleviating, ameliorating, inhibiting, slowing down or stopping the progression, aggravation or deterioration the progression or severity of such a condition. In one embodiment, the symptom of a neurodegenerative condition is alleviated by at least 20%, at least 30%, at least 40%, or at least 50%. In one embodiment, the symptom of a neurodegenerative condition is alleviated by more than 50%. In one embodiment, the symptom of a neurodegenerative condition is alleviated by 80%, 90%, or greater. Treatment also includes improvements in neuromuscular function. In some embodiments, neuromuscular function improves by at least about 10%, 20%, 30%, 40%, 50% or more.

The term "transgene" as used herein, refers to any nucleotide sequence used in the transformation of a plant, animal, or other organism. Thus, a transgene can be a coding sequence, a non-coding sequence, a cDNA, a gene or fragment or portion thereof, a genomic sequence, a regulatory element and the like. A "transgenic" organism, such as a transgenic plant, transgenic microorganism, or transgenic animal, is an organism into which a transgene has been delivered or introduced and the transgene can be expressed in the transgenic organism to produce a product, the presence of which can impart an effect and/or a phenotype in the organism.

By "vector" is meant a polynucleotide molecule, suitably a DNA molecule derived, for example, from a plasmid, bacteriophage, yeast or virus, into which a polynucleotide can be inserted or cloned. A vector may contain one or more unique restriction sites and can be capable of autonomous replication in a defined host cell including a target cell or tissue or a progenitor cell or tissue thereof, or be integrable with the genome of the defined host such that the cloned sequence is reproducible. Accordingly, the vector can be an autonomously replicating vector, i.e., a vector that exists as an extra-chromosomal entity, the replication of which is independent of chromosomal replication, e.g., a linear or closed circular plasmid, an extra-chromosomal element, a mini-chromosome, or an artificial chromosome. The vector can contain any means for assuring self-replication. Alternatively, the vector can be one which, when introduced into the host cell, is integrated into the genome and replicated together with the chromosome(s) into which it has been integrated. A vector system can comprise a single vector or plasmid, two or more vectors or plasmids, which together contain the total DNA to be introduced into the genome of the host cell, or a transposon. The choice of the vector will typically depend on the compatibility of the vector with the host cell into which the vector is to be introduced. In the present case, the vector is preferably a viral or viral-derived vector, which is operably functional in animal and preferably mammalian cells. Non-limiting viral vectors that are useful for the practice of the present invention include adeno-associated viral vectors (AAV), herpes simplex viral vectors and lentiviral vectors. The vector can also include a selection marker such as an antibiotic resistance gene that can be used for selection of suitable transformants. Examples of such resistance genes are known to those of skill in the art and include the nptII gene that confers resistance to the antibiotics kanamycin and G418 (Geneticin®) and the hph gene which confers resistance to the antibiotic hygromycin B.

The terms "wild-type", "native" and "naturally occurring" are used interchangeably herein to refer to a gene or gene product that has the characteristics of that gene or gene product when isolated from a naturally occurring source. A wild type, native or naturally occurring gene or gene product (e.g., a polypeptide) is that which is most frequently observed in a population and is thus arbitrarily designed the "normal" or "wild-type" form of the gene or gene product.

As used herein, underscoring or italicizing the name of a gene shall indicate the gene, in contrast to its protein product, which is indicated by the name of the gene in the absence of any underscoring or italicizing. For example, "cyclin F" shall mean the cyclin F gene, whereas "cyclin F" shall indicate the protein product or products generated from transcription and translation and/or alternative splicing of the "cyclin F" gene.

Each embodiment described herein is to be applied mutatis mutandis to each and every embodiment unless specifically stated otherwise.

2. Abbreviations

The following abbreviations are used throughout the application:
MND=motor neuron disease
 ALS=amyotrophic lateral sclerosis
 FTD=frontotemporal dementia
  hr=hour(s)
 min=minute(s)
  s=second(s)

3. Agents and Methods for Promoting Survival or Inhibiting Degeneration of Motor Neurons The present disclosure demonstrates, inter alia, that a subset of MND patients have motor neurons with an abnormally low level or activity of cyclin F and abnormal protein accumulation, and that cyclin F supplementation can inhibit abnormal protein accumulation in motor neurons, inhibit motor neuron degeneration and promote motor neuron survival.

Based on these findings, the present invention provides methods for promoting motor neuron survival, inhibiting motor neuron degeneration, inhibiting abnormal protein accumulation in motor neurons, treating or preventing neurodegenerative conditions (e.g., ALS or FTD), identifying agents that promote survival of motor neurons, inhibit degeneration of motor neurons and/or inhibit abnormal protein accumulation in motor neurons, identifying agents that are useful for treating neurodegenerative conditions, diagnosing neurodegenerative conditions, predicting the progression of neurodegenerative conditions, and monitoring the effectiveness of a therapy in reducing the progression of a neurodegenerative condition.

Accordingly, the present invention encompasses methods of promoting motor neuron survival, inhibiting motor neuron degeneration and/or inhibiting abnormal protein accumulation in motor neurons, comprising contacting a motor neuron or a population of cells comprising a motor neuron with an agent that enhances the level or activity of cyclin F in the motor neuron.

3.1 Cyclin F-Enhancing Agents

The present invention contemplates any agent that enhances or increases the level or activity of cyclin F in a motor neuron, to thereby promote motor neuron survival, inhibit motor neuron degeneration, and inhibit abnormal protein accumulation in the motor neuron. In some embodiments, an agent that enhances the level or activity of cyclin F increases the level or activity of cyclin F by at least 5%, 10%, 20%, 30%, 40%, 50%, 60%, 70%, 80%, 90%, or 95% or at least 1, 2, 3, 5, 10, 20, 50, or 100-fold more relative to a control.

In specific embodiments, the agent is a nucleic acid construct that comprises a coding sequence for cyclin F operably connected to a promoter. Any coding sequence for cyclin F may be used and suitably corresponds to a wild-type CCNF coding sequence, illustrative examples of which are set forth in SEQ ID NO: 1, 2, 4 and 5 or a sequence corresponding thereto (e.g., a sequence that hybridizes under stringency conditions to any one of the sequences set forth in SEQ ID NO: 1, 2, 4 or 5). In certain embodiments, the coding sequence encodes an amino acid sequence as set forth in SEQ ID NO: 3 or 6, or a sequence corresponding thereto.

Suitably, the nucleic acid construct is in the form of a vector, which is may be a viral vector. Suitable viral vectors for the practice of this invention include, but are not limited to adeno-associated viral vectors (AAV), herpes simplex viral vectors (U.S. Pat. No. 5,672,344) and lentiviral vectors. In specific embodiments, the viral vector is a neurotropic viral vector.

In the practice of the invention, AAV of any serotype can be used. The serotype of the viral vector used in certain embodiments of the invention is selected from the group consisting from AAV1, AAV2, AAV3, AAV4, AAV5, AAV6, AAV7, and AAV8 (see, e.g., Gao et al., 2002, *PNAS* 99:11854-11859; and Viral Vectors for Gene Therapy: Methods and Protocols, ed. Machida, Humana Press, 2003). Other serotypes besides those listed herein can be used. Furthermore, pseudotyped AAV vectors may also be utilized in the methods described herein. Pseudotyped AAV vectors are those which contain the genome of one AAV serotype in the capsid of a second AAV serotype; for example, an AAV vector that contains the AAV2 capsid and the AAV1 genome or an AAV vector that contains the AAV5 capsid and the AAV 2 genome (Auricchio et al., 2001. *Hum. Mol. Genet.* 10(26):3075-81). AAV vectors are derived from single-stranded (ss) DNA parvoviruses that are nonpathogenic for mammals (reviewed in Muzyscka, 1992. *Curr. Top. Microb. Immunol.* 158:97-129). Briefly, recombinant AAV-based vectors have the rep and cap viral genes that account for 96% of the viral genome removed, leaving the two flanking 145-basepair (bp) inverted terminal repeats (ITRs), which are used to initiate viral DNA replication, packaging and integration. In the absence of helper virus, wild-type AAV integrates into the human host-cell genome with preferential site-specificity at chromosome 19q 13.3 or it may be maintained episomally. A single AAV particle can accommodate up to 5 kb of ssDNA, therefore leaving about 4.5 kb for a transgene and regulatory elements, which is typically sufficient. However, trans-splicing systems as described, for example, in U.S. Pat. No. 6,544,785, may nearly double this limit.

In an illustrative embodiment, the AAV is AAV4. Adeno-associated virus of many serotypes, especially AAV2, have been extensively studied and characterized as gene therapy vectors. In another illustrative embodiment, the AAV is AAV5, as disclosed for example by and Klaw et al. (2013, *Mol Ther Nucleic Acids.* 2(7): e108). Those skilled in the art will be familiar with the preparation of functional AAV-based gene therapy vectors. Numerous references to various methods of AAV production, purification and preparation for administration to human subjects can be found in the extensive body of published literature (see, e.g., Viral Vectors for Gene Therapy: Methods and Protocols, ed. Machida, Humana Press, 2003). Additionally, AAV-based gene therapy targeted to cells of the CNS has been described in U.S. Pat. Nos. 6,180,613 and 6,503,888. Additional exemplary AAV vectors are recombinant AAV2/1, AAV2/2, AAV2/5, AAV2/7, AAV2/8 and AAV2/9 serotype vectors encoding human protein. In specific embodiments, the AAV is a neurotropic AAV selected from rAAV2/1, rAAV2/8 and rAAV2/9, as described for example in Ayers et al. (2015, *Mol Ther.* 23(1): 53-62).

3.2 Screening Assay

The present invention also contemplates cyclin F-enhancing agents that are identified using a suitable screening assay. The identified agents are proposed to have any of the characteristics or effects described herein. For example, agents identified by the screening assay described herein may be suitable for use in promoting motor neuron survival, inhibiting motor neuron degeneration, inhibiting abnormal protein accumulation in motor neurons, and/or treating or preventing neurodegenerative conditions (e.g., ALS or FTD). For example, candidate agents for increasing motor neuron survival, inhibiting motor neuron degeneration or inhibiting abnormal protein accumulation in motor neurons can be identified by determining the effect of a test agent on a motor neuron or a cell that is a surrogate for a motor neuron (also referred to herein as a "surrogate cell"), in which the level or activity of cyclin F is reduced, and/or in which another gene associated with development of a neurodegenerative condition (e.g., TDP-43 or another protein susceptible to aggregation such as SOD1) is expressed or overexpressed, and where a greater number of motor neurons or surrogate cells in the presence of a test agent relative to a control indicate that the test agent can promote motor neuron survival, inhibit motor neuron degeneration, inhibit abnormal protein accumulation in a motor neuron.

Thus, in specific embodiments, the screening assay of the present invention comprises: (a) contacting a population of cells with a test agent, wherein the cells have a reduced level or activity of cyclin F and/or abnormal protein accumulation relative to a control, and (b) measuring (i) the level or activity of cyclin F and/or (ii) abnormal protein accumulation in the cells, in the presence of the test agent, and (c) identifying the candidate agent for treating or preventing a neurodegenerative condition, wherein the test agent is a candidate agent for treating or preventing a neurodegenerative condition if the test agent (i) increases the level or activity of cyclin F or (ii) reduces abnormal protein accumulation, in the presence of the test agent.

In some embodiments, the cells are motor neurons. The motor neurons can be obtained from any source available to one of skill in the art. Additionally, the motor neurons can be of any origin. Accordingly, in some embodiments, the motor neurons are mammalian motor neurons. In certain embodiments, the motor neurons are human motor neurons or mouse motor neurons. In illustrative examples of this type, the motor neurons are mouse ES cell-derived motor neuron. In other illustrative examples, the motor neurons are selected from motor neuron cells lines such as but not limited to HB9 motor neurons, G93A motor neurons, HUES3 derived motor neurons, and combinations thereof.

Suitably, the motor neurons are from a subject, e.g., a patient. In some embodiments, the subject, e.g., a patient, is suffering from a neurodegenerative condition. In some embodiments, the neurodegenerative condition is ALS or FTD. In certain embodiments, the motor neuron is from a carrier, e.g., a symptom-free carrier.

The motor neurons may intrinsically have a reduced level or activity of cyclin F relative and/or abnormal protein accumulation relative to a control or may have been caused to have a reduced level or activity of cyclin F relative and/or abnormal protein accumulation relative to a control through introduction of at least one transgene. The transgene modulates a gene that is associated with development of a neurodegenerative condition. In specific embodiments, the transgene comprises a cyclin F antagonist nucleic acid molecule that functions to inhibit the transcription or translation of cyclin Ftranscripts. Representative transcripts of this type include nucleotide sequences corresponding to any one the sequences set forth in SEQ ID NO: 1, 2, 4, and 5. Illustrative antagonist nucleic acid molecules include antisense molecules, aptamers, ribozymes and triplex forming molecules, RNAi and external guide sequences. Alternatively, or in addition, a transgene from which a protein susceptible to aggregation (e.g., TDP-43) is expressed may be introduced into the motor neurons. In non-limiting examples of this type, the expression of aggregation susceptible protein (e.g., TDP-43) is conditional through use of a regulatable promoter.

In some embodiments, the screening methods of the present invention employ cells that are not motor neurons but are otherwise surrogates for motor neurons, wherein the cells intrinsically have a reduced level or activity of cyclin F relative and/or abnormal protein accumulation relative to a control or may have been caused to have a reduced level or activity of cyclin F relative and/or abnormal protein accumulation relative to a control through introduction of at least one transgene as described for example above in connection with motor neurons. In illustrative examples of this type, the screening methods of the present invention employ fibroblasts comprising the at least one transgene. In other embodiments, the screening methods of the present invention employ a cell line (e.g., HEK293 cells) that comprise the at least one transgene.

In non-limiting examples of the assay, a test agent is contacted or incubated with the cells and after a sufficient period of time, the influence of the candidate agent is determined on survival of the cells, degeneration or the cells, and/or protein accumulation (e.g., TDP-43 accumulation) in motor neurons. In specific embodiments, cells that have survived are counted and their number compared to a control. A control can be a sample that is that is not contacted with a test agent. A control can be a sample that is treated with a known promoter of motor neuron survival. This can serve as a positive control. A control can be a sample that is treated with a known inhibitor of motor neuron survival.

Some exemplary promoters of motor neuron survival include, but are not limited to, kenpaullone, alsterpaullone, cycloheximide (CHX), and derivatives thereof. Additional promoters of motor neuron survival include those described, for example, in PCT/US2009/061468, filed Oct. 21, 2009.

The test agents can include a wide variety of different compounds, including chemical compounds and mixtures of chemical compounds, e.g., small organic or inorganic molecules; saccharides; oligosaccharides; polysaccharides; biological macromolecules, e.g., peptides, proteins, and peptide analogs and derivatives; peptidomimetics; nucleic acids; nucleic acid analogs and derivatives; an extract made from biological materials such as bacteria, plants, fungi, or animal cells; animal tissues; naturally occurring or synthetic compositions; and any combinations thereof. In some embodiments, the test agent is a small molecule.

The number of possible test agents runs into millions. Methods for developing small molecule, polymeric and genome based libraries are described, for example, in Ding et al. (2002, *J Am. Chem. Soc.* 124: 1594-1596) and Lynn et al. (2001, *J. Am. Chem. Soc.* 123: 8155-8156). Commercially available compound libraries can be obtained from, e.g., Tocris Bioscience, ChemDiv, ArQule, Pharmacopia, graffinity, Panvera, Vitas-M Lab, Biomol International and Oxford. These libraries can be screened using the screening devices and methods described herein. Chemical compound libraries such as those from NIH Roadmap, Molecular Libraries Screening Centers Network (MLSCN) can also be used. A chemical library or compound library is a collection of stored chemicals usually used ultimately in high-throughput screening or industrial manufacture. The chemical library can consist in simple terms of a series of stored chemicals. Each chemical has associated information stored in some kind of database with information such as the chemical structure, purity, quantity, and physiochemical characteristics of the compound.

Depending upon the particular embodiment being practiced, the test agents can be provided free in solution, or may be attached to a carrier, or a solid support, e.g., beads. A number of suitable solid supports may be employed for immobilization of the test agents. Examples of suitable solid supports include agarose, cellulose, dextran (commercially available as, i.e., Sephadex, Sepharose) carboxymethyl cellulose, polystyrene, polyethylene glycol (PEG), filter paper, nitrocellulose, ion exchange resins, plastic films, polyaminemethylvinylether maleic acid copolymer, glass beads, amino acid copolymer, ethylene-maleic acid copolymer, nylon, silk, etc. Additionally, for the methods described herein, test agents may be screened individually, or in groups. Group screening is particularly useful where hit rates for effective test agents are expected to be low such that one would not expect more than one positive result for a given group.

Without limitations, cells can be plated at any density that provides an optimal signal-to-noise ratio. For example, cells can be plated at a density of 1,000 to 20,000 cells/well in a 384-well plate. In some embodiments, cells are plated at density of 1,000; 2,000; 4,000; 8,000; 12,000; 16,000; or 20,000 cells/well in a 384-well plate. In one embodiment, cells are plated at a density of 8,000 cells/well in a 384-well plate. Based on the foregoing, one of ordinary skill can adjust the plating density for other cell culturing vessels. For example, one can calculate the dimensions of a well in the 384-well plate and the vessels to be used and scale the number of cells to be plated based on volume or surface area ratio between a well from the 384-well plate and the vessel to be used.

In specific embodiments, accumulation of a protein susceptible to aggregation (e.g., TDP-43) is measured. In non-limiting examples of this type, the aggregation susceptible protein comprises a detectable label. The detectable label may be any suitable label known in the art, as described for example below. In certain embodiments, the detectable label is an optical reporter such as a fluorescent reporter (e.g., a YFP tag) that may be detected using a high content microscopy system to allow for high-throughput screening. In other embodiments, the detectable label is a phosphorescent moiety, an epitope, radiolabel, or any other detectable moiety known in the art, and may be detected using any of the methods known in the art. In certain embodiments, the detectable label allows for the measurement of cell viability, as described for example below. In embodiments of the screening assay in which protein accumulation is assessed, a decrease in protein accumulation relative to a control indicates that a test agent inhibits protein accumulation. In these instances, the screening assay suitably further comprises detecting an increase in the level or activity of cyclin F in the same cells or cells of the same type in which protein accumulation was inhibited by the test agent. In representative examples of this type, the level of cyclin F in the cells is determined using a suitable immunoassay (e.g., western blot or immunohistochemistry).

In some embodiments, survival of a motor neuron or surrogate cell is assessed and in non-limiting examples of this type, the assessment comprises detecting a motor neuron or surrogate cell marker and a cell-replication marker. A selected test agent can be further limited to the agent where the motor neuron or surrogate cell marker and the cell-replication marker co-localize in the same cell.

Any available method for identifying and counting motor neurons or surrogate cells in a culture can be employed. For example, a motor neuron or surrogate cell can comprise a detectable label or provide a detectable response for identification or counting. In some embodiments, the detectable label is an optical reporter. Suitable optical reporters include, but are not limited to, fluorescent reporters and chemiluminescent groups. A wide variety of fluorescent reporter dyes are known in the art. Typically, the fluorophore is an aromatic or heteroaromatic compound and can be a pyrene, anthracene, naphthalene, acridine, stilbene, indole, benzindole, oxazole, thiazole, benzothiazole, cyanine, carbocyanine, salicylate, anthranilate, coumarin, fluorescein, rhodamine or other like compound. Suitable fluorescent reporters include xanthene dyes, such as fluorescein or rhodamine dyes, including, but not limited to, Alexa Fluor® dyes (Invitrogen Corp.; Carlsbad, Calif.), fluorescein, fluorescein isothiocyanate (FITC), Oregon Green™, rhodamine, Texas red, tetrarhodamine isothiocyanate (TRITC), 5-carboxyfluorescein (FAM), 2'7'-dimethoxy-4'5'-dichloro-6-carboxyfluorescein (JOE), tetrachlorofluorescein (TET), 6-carboxyrhodamine (R6G), N,N,N,N'-tetramethyl-6-carboxyrhodamine (TAMRA), 6-carboxy-X-rhodamine (ROX). Suitable fluorescent reporters also include the naphthylamine dyes that have an amino group in the alpha or beta position. For example, naphthylamino compounds include 1-dimethylamino-naphthyl-5-sulfonate, 1-anilino-8-naphthalene sulfonate, 2-p-toluidinyl-6-naphthalene sulfonate, and 5-(2'-aminoethyl)aminonaphthalene-1-sulfonic acid (EDANS). Other fluorescent reporter dyes include coumarins, such as 3-phenyl-7-isocyanatocoumarin; acridines, such as 9-isothiocyanatoacridine and acridine orange; N-(p(2-benzoxazolyl)phenyl)maleimide; cyanines, such as Cy2, indodicarbocyanine 3 (Cy3), indodicarbocyanine 5 (Cy5), indodicarbocyanine 5.5 (Cy5.5), 34-carboxy-pentyl)-3'ethyl-5,5'-dimethyloxacarbocyanine (CyA); 1H,5H,11H,15H-Xantheno[2,3,4-ij:5,6,7-i'j']diquinolizin-18-ium, 9-[2 (or 4)-[[[6-[2,5-dioxo-1-pyrrolidinyl)oxy]-6-oxohexyl]amino]sulfonyl]-4(or 2)-sulfophenyl]-2,3,6,7,12,13,16,17octahydro-inner salt (TR or Texas Red); BODIPY™ dyes; benzoxadiazoles; stilbenes; pyrenes; and the like. Many suitable forms of these fluorescent compounds are available and can be used.

In some embodiments, the motor neurons or surrogate cells express a fluorescent protein. Examples of fluorescent proteins suitable for use as detectable label include, but are not limited to, green fluorescent protein, red fluorescent protein (e.g., DsRed), yellow fluorescent protein, cyan fluorescent protein, blue fluorescent protein, and variants thereof (see, e.g., U.S. Pat. Nos. 6,403,374, 6,800,733, and 7,157,566). Specific examples of GFP variants include, but are not limited to, enhanced GFP (EGFP), destabilized EGFP, the GFP variants described in Doan et al. (2005, Mol. Microbiol. 55:1767-1781), the GFP variant described in Crameri et al. (1996, Nat. Biotechnol. 14:315319), the cerulean fluorescent proteins described in Rizzo et al. (2004, Nat. Biotechnol. 22:445) and Tsien (1998, Annu. Rev. Biochem. 67:509), and the yellow fluorescent protein described in Nagal et al. (2002, Nat. Biotechnol. 20:87-90). DsRed variants are described in, e.g., Shaner et al. (2004, Nat. Biotechnol. 22:1567-1572), and include mStrawberry, mCherry, morange, mBanana, mHoneydew, and mTangerine. Additional DsRed variants are described in, e.g., Wang et al. (2004, Proc. Natl. Acad. Sci. U.S.A. 101:16745-16749) and include mRaspberry and mPlum. Further examples of DsRed variants include mRFPmars described in Fischer et al. (2004, FEBS Lett. 577:227-232) and mRFPruby described in Fischer et al. (2006, FEBS Lett. 580:2495-2502).

A non-limiting list of fluorescent proteins incudes AceGFP, AcGFP1, AmCyan1, AQ143, AsRed2, Azami-Green (mAG), Cerulean, Cerulean, Citrine, cOFP, CopGFP, Cyan, CyPet, Dronpa, DsRed/DsRed2/DsRed-Express, DsRed-Monomer, EBFP, ECFP, EGFP, Emerald, eqFP611, EYFP, GFPs, HcRedl, HcRed-tandem, J-Red, Kaede, KFP, KikGR, mBanana, mCFP, mCherry, mCitrine, mEosEP, mHoneydew, MiCy, mKO, mOrange, mPlum, mRaspberry, mRFP1, mStrawberry, mTangerine, mYFP, mYFP, mYFP, PA-GFP, PA-mRFP, PhiYFP, PS-CFP-2, Renilla, tdFosFP, tdTomato, T-Sapphire, TurboGFP, UV-T-Sapphire, Venus, YPet, ZsYellowI, and derivatives and analogs thereof. In one embodiment, the fluorescent protein is Green Fluorescent Protein (GFP).

Specific devices or methods known in the art for the detection of fluorescence, e.g., from fluorophores or fluorescent proteins, include, but are not limited to, in vivo near-infrared fluorescence (see, e.g., Frangioni, 2003. Curr. Opin. Chem. Biol. 7:626-634), the Maestro™ in vivo fluorescence imaging system (Cambridge Research & Instrumentation, Inc.; Woburn, Mass.), in vivo fluorescence imaging using a flying-spot scanner (see, e.g., Ramanujam et al. (2001, IEEE Transactions on Biomedical Engineering 48:1034-1041), and the like. Other methods or devices for detecting an optical response include, without limitation, visual inspection, CCD cameras, video cameras, photographic film, laser-scanning devices, fluorometers, photodiodes, quantum counters, epifluorescence microscopes, scanning microscopes, flow cytometers, fluorescence microplate readers, or signal amplification using photomultiplier tubes.

A fluorescent protein can be expressed from a transgenic reporter gene in the motor neuron or surrogate cell. Expression of the fluorescent protein from the transgenic reporter gene can be operably linked to expression of a motor neuron specific gene or can be under the control of a motor neuron specific promoter. Accordingly, in some embodiments, the sequence encoding the fluorescent protein is operably linked to a promoter for a gene specific for motor neurons. In one embodiment, the sequence encoding the fluorescent protein is operably linked to the HB9 gene promoter.

In some embodiments, motor neurons or surrogate cells are counted by an image-based method. Presence of a detectable label makes image-based method more amenable to automation. When the motor neurons or surrogate cells express a fluorescent protein, surviving motor neurons can be those that are expressing the fluorescent protein when the counting is performed. In some embodiments, the number of motor neuron surviving after incubation with the test agent is at least about at least about 5%, 10%, 15%, 20%, 25%, 30%, 35%, 40%, 45%, 50%, 55%, 60%, 65%, 70%, 75%, 80%, 85%, 90%, 95%, 100%, 1.1-fold, 1.25-fold, 1.5-fold, 1.75-fold, 2-fold, 3-fold, 4-fold, 5-fold, 10-fold or higher than a control.

In some embodiments, the number of motor neurons or surrogate cells in a sample is assessed via automated image acquisition and analysis using a Cellomics ArrayScan VII. The acquisition thresholds/parameters are established such that the computer-based calls of number of motor neurons are consistent with human-based calls. Such automated image acquisition and analysis allows for high-throughput screening of compounds.

Number of motor neurons can be assessed by: (i) increased total number of cells in the culture, as compared to an untreated control; (ii) increased total number of cells expressing a detectable label in the test culture, as compared to an untreated control; (iii) increased ratio of cells expressing a detectable label to the total number of cells in the culture, as compared to an untreated control; or (iv) a combination thereof.

The assay can be performed any suitable container or apparatus available to one of skill in the art for cell culturing. For example, the assay can be performed in 24-, 96-, or 384-well plates. In one embodiment, the assay is performed in a 384-well plate.

In embodiments of the screening assay in which survival of a motor neuron or surrogate cell is assessed, an increase in survival relative to a control indicates that a test agent promotes survival of the motor neuron or surrogate cell, or inhibits or reduces degeneration or death of the motor neuron or surrogate cell. In these instances, the screening assay suitably further comprises detecting an increase in the level or activity of cyclin F in the same cells or cells of the same type in which cell survival was increased or cell degeneration or death was inhibited by the test agent. In representative examples of this type, the level of cyclin F in the cells is determined using a suitable immunoassay (e.g., western blot or immunohistochemistry).

In some embodiments, the screening method is a high-throughput screening. High-throughput screening (HTS) is a method for scientific experimentation that uses robotics, data processing and control software, liquid handling devices, and sensitive detectors. High-Throughput Screening or HTS allows a researcher to quickly conduct millions of biochemical, genetic or pharmacological tests. High-Throughput Screening are well known to one skilled in the art, for example, those described in U.S. Pat. Nos. 5,976,813; 6,472,144; 6,692,856; 6,824,982; and 7,091,048, and contents of each of which is herein incorporated by reference in its entirety.

HTS uses automation to run a screen of an assay against a library of candidate compounds. An assay is a test for specific activity: usually inhibition or stimulation of a biochemical or biological mechanism. Typical HTS screening libraries or "decks" can contain from 100,000 to more than 2,000,000 compounds.

The key labware or testing vessel of HTS is the microtiter plate: a small container, usually disposable and made of plastic that features a grid of small, open divots called wells. Modern microplates for HTS generally have either 384, 1536, or 3456 wells. These are all multiples of 96, reflecting the original 96-well microplate with 8×12 9 mm spaced wells.

To prepare for an assay, the researcher fills each well of the plate with the appropriate reagents that he or she wishes to conduct the experiment with, such as a motor neuron or surrogate cell population. After some incubation time has passed to allow the reagent to absorb, bind to, or otherwise react (or fail to react) with the compounds in the wells, measurements are taken across all the plate's wells, either manually or by a machine. Manual measurements are often necessary when the researcher is using microscopy to (for example) seek changes that a computer could not easily determine by itself. Otherwise, a specialized automated analysis machine can run a number of experiments on the wells such as colorimetric measurements, radioactivity counting, etc. In this case, the machine outputs the result of each experiment as a grid of numeric values, with each number mapping to the value obtained from a single well. A high-capacity analysis machine can measure dozens of plates in the space of a few minutes like this, generating thousands of experimental data points very quickly.

In another aspect, the invention provides a compound or agent selected by the screening assay described herein. It is to be understood that analogs, derivatives, isomers, and pharmaceutically acceptable salts of the compounds selected by the screening assays described herein are also encompassed herein.

4. Contacting of Motor Neurons or Surrogate Cells

Cells such as motor neurons or non-motor neuron cells that are suitably surrogates for motor neurons (also referred to herein as "surrogate cells"), or populations of cells comprising motor neurons or surrogate cells, as described for example herein, can be contacted with the agents described herein in a cell culture e.g., in vitro or ex vivo, or administrated to a subject, e.g., in vivo. In some embodiments, an agent described herein can be administrated to a subject to treat, prevent, and/or diagnose neurodegenerative conditions, including those described herein. In some embodiments, a compound and/or agent described herein can be administered to a subject to treat, prevent, and/or diagnose ALS. In some embodiments, a compound and/or agent described herein can be administered to a subject to treat, prevent, and/or diagnose FTD.

For in vitro methods, motor neurons can be obtained from different sources. For example, motor neurons can be obtained from a subject, or derived from non-motor neuron cells from a subject. In some embodiments, motor neuron is a whole cell. In some embodiments, the subject is suffering from a neurodegenerative condition. In some embodiments, the subject is at risk of developing a neurodegenerative condition. In some embodiments, the subject is suspected of having a neurodegenerative condition. In some embodiments, the subject is at risk of developing a condition characterized by neuronal cell death. In some embodiments, the subject is suspected of suffering from a condition characterized by neuronal cell death. In some embodiments, the subject is suffering from neuronal cell death. In some embodiments, the subject is suffering from SMA. In some embodiments, the subject is suffering from ALS. In some embodiments, the subject is a carrier e.g., a symptom-free carrier. In some embodiments, motor neuron cells are derived from a subject's embryonic stem cells (ESCs). In some embodiments, the subject is human. In some embodiments, the subject is mouse. In some embodiments, mouse is a transgenic mouse. Methods of inducing motor neuron differentiation from embryonic stem cells are known in the art, for example as described in Di Giorgio et al., Nature Neuroscience (2007), published online 15 Apr. 2007; doi: 10.1038/nn1885 and Wichterle et al., Cell (2002) 110:385-397. In some instances, induced pluripotent stem cells can be generated from a subject and then differentiated into motor neurons. One exemplary method of deriving motor neurons from a subject is described in Dimos, J. T., et al. Science (2008) 321, 1218-122 (Epub Jul. 31, 2008).

For in vivo methods, a therapeutically effective amount of an agent described herein can be administered to a subject. Methods of administering agents to a subject are known in the art and easily available to one of skill in the art.

Those skilled in the art will also appreciate that the agents described herein can be used for inhibiting motor neuron degeneration or promoting motor neuron survival, which can lead to treatment, prevention or amelioration of a number of conditions characterized by motor neuron degeneration. The motor neuron diseases (MND) are a group of neurodegenerative conditions that selectively affect motor neurons, the nerve cells that control voluntary muscle activity including speaking, walking, breathing, swallowing and general movement of the body. Skeletal muscles are innervated by a group of neurons (lower motor neurons) located in the ventral horns of the spinal cord which project out the ventral roots to the muscle cells. These nerve cells are themselves innervated by the corticospinal tract or upper motor neurons that project from the motor cortex of the brain. On macroscopic pathology, there is a degeneration of the ventral horns of the spinal cord, as well as atrophy of the ventral roots. In the brain, atrophy may be present in the frontal and temporal lobes. On microscopic examination, neurons may show spongiosis, the presence of activated astrocytes and microglia, and a number of inclusions including characteristic "skein-like" inclusions, bunina bodies, and vacuolization. Motor neuron diseases are varied and destructive in their effect. They commonly have distinctive differences in their origin and causation, but a similar result in their outcome for the patient: severe muscle weakness. Amyotrophic lateral sclerosis (ALS), frontotemporal dementia (FTD), primary lateral sclerosis (PLS), progressive muscular atrophy (PMA), pseudobulbar palsy, progressive bulbar palsy, spinal muscular atrophy (SMA) and post-polio syndrome are all examples of MND. The major site of motor neuron degeneration classifies the neurodegenerative condition.

ALS, which affects both upper and lower motor neurons, is the most common form of MND. Progressive bulbar palsy affects the lower motor neurons of the brain stem, causing slurred speech and difficulty chewing and swallowing. Individuals with these conditions almost always have abnormal signs in the arms and legs. Primary lateral sclerosis is a disease of the upper motor neurons, while progressive muscular atrophy affects only lower motor neurons in the spinal cord. Means for diagnosing MND are well known to those skilled in the art. Non limiting examples of symptoms are described below.

4.1 Amyotrophic Lateral Sclerosis (ALS)

Amyotrophic lateral sclerosis (ALS), also called Lou Gehrig's disease or classical motor neuron disease, is a progressive, ultimately fatal disorder that eventually disrupts signals to all voluntary muscles. In the United States, doctors use the terms motor neuron disease and ALS interchangeably. Both upper and lower motor neurons are affected. Approximately 75 percent of people with classic ALS will also develop weakness and wasting of the bulbar muscles (muscles that control speech, swallowing, and chewing). Symptoms are usually noticed first in the arms and hands, legs, or swallowing muscles. Muscle weakness and atrophy occur disproportionately on both sides of the body. Affected individuals lose strength and the ability to move their arms, legs, and body. Other symptoms include spasticity, exaggerated reflexes, muscle cramps, fasciculations, and increased problems with swallowing and forming words. Speech can become slurred or nasal. When muscles of the diaphragm and chest wall fail to function properly, individuals lose the ability to breathe without mechanical support. Although the disease does not usually impair a person's mind or personality, several recent studies suggest that some people with ALS may have alterations in cognitive functions such as problems with decision-making and memory. ALS most commonly strikes people between 40 and 60 years of age, but younger and older people also can develop the disease. Men are affected more often than women. Most cases of ALS occur sporadically, and family members of those individuals are not considered to be at increased risk for developing the disease. However, there is a familial form of ALS in adults, which often results from mutation of genes responsible for RNA metabolism (e.g., TDP43 and FUS) and protein degradation (e.g., UBQLN2, TBK1 and CCNF). In addition, a rare juvenile-onset form of ALS is genetic. Most individuals with ALS die from respiratory failure, usually within 3 to 5 years from the onset of symptoms. However, about 10 percent of affected individuals survive for 10 or more years.

4.2 Frontotemporal Dementia (FTD)

Frontotemporal dementia (FTD) is the clinical presentation of frontotemporal lobar degeneration, which is characterized by progressive neuronal loss predominantly involving the frontal and/or temporal lobes, and typical loss of over 70% of spindle neurons, while other neuron types remain intact In FTD, portions of frontal and temporal lobes atrophy or shrink. The frontal and temporal lobes of the brain are generally associated with personality, behavior and language. Common signs and symptoms vary, depending upon the portion of the brain affected. Some people with FTD undergo dramatic changes in their personality and become socially inappropriate, impulsive or emotionally indifferent, while others lose the ability to use language. signs and symptoms include significant changes in social and personal behavior, apathy, blunting of emotions, and deficits in both expressive and receptive language. Currently, there is no cure for FTD, but there are treatments that help alleviate symptoms.

4.3 Spinal Muscular Atrophy (SMA)

Spinal muscular atrophy (SMA) refers to a number of different disorders, all having in common a genetic cause and the manifestation of weakness due to loss of the motor neurons of the spinal cord and brainstem. Weakness and wasting of the skeletal muscles is caused by progressive degeneration of the anterior horn cells of the spinal cord. This weakness is often more severe in the legs than in the arms. SMA has various forms, with different ages of onset, patterns of inheritance, and severity and progression of symptoms. Some of the more common SMAs are described below.

Defects in SMN gene products are considered as the major cause of SMA and SMN protein levels correlate with survival of subject suffering from SMA. The most common form of SMA is caused by mutation of the SMN gene. The region of chromosome 5 that contains the SMN (survival motor neuron) gene has a large duplication. A large sequence that contains several genes occurs twice in adjacent segments. There are thus two copies of the gene, SMN1 and SMN2. The SMN2 gene has an additional mutation that makes it less efficient at making protein, though it does so in a low level. SMA is caused by loss of the SMN1 gene from both chromosomes. The severity of SMA, ranging from SMA 1 to SMA 3, is partly related to how well the remaining SMN 2 genes can make up for the loss of SMN 1.

SMA type I, also called Werdnig-Hoffmann disease, is evident by the time a child is 6 months old. Symptoms may include hypotonia (severely reduced muscle tone), diminished limb movements, lack of tendon reflexes, fasciculations, tremors, swallowing and feeding difficulties, and impaired breathing. Some children also develop scoliosis (curvature of the spine) or other skeletal abnormalities. Affected children never sit or stand and the vast majority usually die of respiratory failure before the age of 2.

Symptoms of SMA type II usually begin after the child is 6 months of age. Features may include inability to stand or walk, respiratory problems, hypotonia, decreased or absent tendon reflexes, and fasciculations. These children may learn to sit but do not stand. Life expectancy varies, and some individuals live into adolescence or later.

Symptoms of SMA type III (Kugelberg-Welander disease) appear between 2 and 17 years of age and include abnormal gait; difficulty running, climbing steps, or rising from a chair; and a fine tremor of the fingers. The lower extremities are most often affected. Complications include scoliosis and joint contractures—chronic shortening of muscles or tendons around joints, caused by abnormal muscle tone and weakness, which prevents the joints from moving freely.

Other forms of SMA include e.g., Hereditary Bulbo-Spinal SMA Kennedy's disease (X linked, Androgen receptor), SMA with Respiratory Distress (SMARD 1) (chromosome 11, IGHMBP2 gene), Distal SMA with upper limb predominance (chromosome 7, glycyl tRNA synthase), and X-Linked infantile SMA (gene UBE1).

Current treatment for SMA consists of prevention and management of the secondary effect of chronic motor unit loss. Some drugs under clinical investigation for the treatment of SMA include butyrates, Valproic acids, hydroxyurea and Riluzole.

Symptoms of Fazio-Londe disease appear between 1 and 12 years of age and may include facial weakness, dysphagia (difficulty swallowing), stridor (a high-pitched respiratory sound often associated with acute blockage of the larynx), difficulty speaking (dysarthria), and paralysis of the eye muscles. Most individuals with SMA type III die from breathing complications.

Kennedy disease, also known as progressive spinobulbar muscular atrophy, is an X-linked recessive disease. Daughters of individuals with Kennedy disease are carriers and have a 50 percent chance of having a son affected with the disease. Onset occurs between 15 and 60 years of age. Symptoms include weakness of the facial and tongue muscles, hand tremor, muscle cramps, dysphagia, dysarthria, and excessive development of male breasts and mammary glands. Weakness usually begins in the pelvis before spreading to the limbs. Some individuals develop noninsulin-dependent diabetes mellitus.

The course of the disorder varies but is generally slowly progressive. Individuals tend to remain ambulatory until late in the disease. The life expectancy for individuals with Kennedy disease is usually normal.

Congenital SMA with arthrogryposis (persistent contracture of joints with fixed abnormal posture of the limb) is a rare disorder. Manifestations include severe contractures, scoliosis, chest deformity, respiratory problems, unusually small jaws, and drooping of the upper eyelids.

Progressive bulbar palsy, also called progressive bulbar atrophy, involves the bulb-shaped brain stem—the region that controls lower motor neurons needed for swallowing, speaking, chewing, and other functions. Symptoms include pharyngeal muscle weakness (involved with swallowing), weak jaw and facial muscles, progressive loss of speech, and tongue muscle atrophy. Limb weakness with both lower and upper motor neuron signs is almost always evident but less prominent. Affected persons have outbursts of laughing or crying (called emotional lability). Individuals eventually become unable to eat or speak and are at increased risk of choking and aspiration pneumonia, which is caused by the passage of liquids and food through the vocal folds and into the lower airways and lungs. Stroke and myasthenia gravis each have certain symptoms that are similar to those of progressive bulbar palsy and must be ruled out prior to diagnosing this disorder. In about 25 percent of ALS cases early symptoms begin with bulbar involvement. Some 75 percent of individuals with classic ALS eventually show some bulbar involvement. Many clinicians believe that progressive bulbar palsy by itself, without evidence of abnormalities in the arms or legs, is extremely rare.

Pseudobulbar palsy, which shares many symptoms of progressive bulbar palsy, is characterized by upper motor neuron degeneration and progressive loss of the ability to speak, chew, and swallow. Progressive weakness in facial muscles leads to an expressionless face. Individuals may develop a gravelly voice and an increased gag reflex. The tongue may become immobile and unable to protrude from the mouth. Individuals may also experience emotional lability.

Primary lateral sclerosis (PLS) affects only upper motor neurons and is nearly twice as common in men as in women. Onset generally occurs after age 50. The cause of PLS is unknown. It occurs when specific nerve cells in the cerebral cortex (the thin layer of cells covering the brain which is responsible for most higher level mental functions) that control voluntary movement gradually degenerate, causing the muscles under their control to weaken. The syndrome—which scientists believe is only rarely hereditary—progresses gradually over years or decades, leading to stiffness and clumsiness of the affected muscles. The disorder usually affects the legs first, followed by the body trunk, arms and hands, and, finally, the bulbar muscles. Symptoms may include difficulty with balance, weakness and stiffness in the legs, clumsiness, spasticity in the legs which produces slowness and stiffness of movement, dragging of the feet (leading to an inability to walk), and facial involvement resulting in dysarthria (poorly articulated speech). Major differences between ALS and PLS (considered a variant of ALS) are the motor neurons involved and the rate of disease progression. PLS may be mistaken for spastic paraplegia, a hereditary disorder of the upper motor neurons that causes spasticity in the legs and usually starts in adolescence. Most neurologists follow the affected individual's clinical course for at least 3 years before making a diagnosis of PLS. The disorder is not fatal but may affect quality of life. PLS often develops into ALS.

Progressive muscular atrophy (PMA) is marked by slow but progressive degeneration of only the lower motor neurons. It largely affects men, with onset earlier than in other MNDs. Weakness is typically seen first in the hands and then spreads into the lower body, where it can be severe. Other symptoms may include muscle wasting, clumsy hand movements, fasciculations, and muscle cramps. The trunk muscles and respiration may become affected. Exposure to cold can worsen symptoms. The disease develops into ALS in many instances.

Post-polio syndrome (PPS) is a condition that can strike polio survivors decades after their recovery from poliomyelitis. PPS is believed to occur when injury, illness (such as degenerative joint disease), weight gain, or the aging process damages or kills spinal cord motor neurons that remained functional after the initial polio attack. Many scientists believe PPS is latent weakness among muscles previously affected by poliomyelitis and not a new MND. Symptoms include fatigue, slowly progressive muscle weakness, muscle atrophy, fasciculations, cold intolerance, and muscle and joint pain. These symptoms appear most often among muscle groups affected by the initial disease. Other symptoms include skeletal deformities such as scoliosis and difficulty breathing, swallowing, or sleeping. Symptoms are more frequent among older people and those individuals most severely affected by the earlier disease. Some individuals experience only minor symptoms, while others develop SMA and, rarely, what appears to be, but is not, a form of ALS. PPS is not usually life threatening. Doctors estimate the incidence of PPS at about 25 to 50 percent of survivors of paralytic poliomyelitis.

In some embodiments, neurodegenerative condition can be ALS or FTD.

In some embodiments, the methods described herein further comprise selecting a subject diagnosed with a neurodegenerative condition. A subject suffering from a neurodegenerative condition can be selected based on the symptoms presented. For example, a subject suffering from ALS may show symptoms of fasciculations, cramps, tight and stiff muscles (spasticity), twitching in arms, shoulder or tongue, muscle weakness affecting a hand, arm or leg, slurred and nasal speech, or difficulty chewing or swallowing.

In some embodiments, the methods described herein further comprise selecting a subject at risk of developing a neurodegenerative condition. A subject at risk of developing a neurodegenerative condition can be selected based on a genetic diagnostic test (e.g., for a mutation in a gene associated with a neurodegenerative condition (e.g., that assays cyclin F level or activity) or based on the symptoms presented. For example, a subject suffering from ALS may show symptoms of fasciculations, cramps, tight and stiff muscles (spasticity), twitching in arms, shoulder or tongue, muscle weakness affecting a hand, arm or leg, slurred and nasal speech, or difficulty chewing or swallowing.

In some embodiments, the methods described herein further comprise selecting a subject suspected of having a neurodegenerative condition. A subject suspected of having a neurodegenerative condition can be selected based on a diagnostic test (e.g., that assays cyclin F level or activity) or based on the symptoms presented or a combination thereof. For example, a subject suffering from ALS may show symptoms of fasciculations, cramps, tight and stiff muscles (spasticity), twitching in arms, shoulder or tongue, muscle weakness affecting a hand, arm or leg, slurred and nasal speech, or difficulty chewing or swallowing.

5. Diagnostic Tests, Monitoring Disease Progression, and Efficacy of Treatment Certain aspects of the present disclosure relate to diagnostic tests and methods of diagnosing neurodegenerative conditions and/or conditions characterized by motor neuron degeneration. Other aspects of the disclosure relate to methods for monitoring progression of a neurodegenerative condition in a subject, and methods of monitoring the effectiveness of a therapy in reducing the progression of a neurodegenerative condition in a subject.

In an aspect, a method for diagnosing a neurodegenerative condition in a subject, comprises: detecting in the subject a motor neuron or a cell that is a surrogate for a motor neuron (e.g., a skin cell such as a skin fibroblast, or a blood cells such as a peripheral blood mononuclear cell, etc.) having a reduced level of cyclin F relative to a control.

In representative examples of this type, the diagnostic method comprises: (a) obtaining a sample comprising cells from the subject; (b) conducting at least one assay on the cells in the sample to detect the level or activity of cyclin F in the cells; and (c) diagnosing the subject as having a neurodegenerative condition if the level or activity of the cyclin F in the cells is reduced relative to a level or activity of cyclin F in a control sample. In specific embodiments, the cells are selected from motor neurons or cells that are surrogates for motor neurons (e.g., skin cells such as skin fibroblasts, blood cells such as peripheral blood mononuclear cells, etc.).

In an aspect, a method for predicting the progression of a neurodegenerative condition in a subject, comprises: (a) obtaining a first sample from the subject, wherein the first sample comprises motor neurons and/or cells that are surrogates for motor neurons (e.g., skin cells such as skin fibroblasts, blood cells such as peripheral blood mononuclear cells, etc.); (b) obtaining a second sample from the subject at a time which is later than when the first sample was obtained, wherein the second sample comprises motor neurons and/or cells that are surrogates for motor neurons (e.g., skin cells such as skin fibroblasts, blood cells such as peripheral blood mononuclear cells, etc.); (c) conducting at least one assay on the cell samples to detect a level or activity of cyclin F; and (d) predicting the progression of the neurodegenerative condition in the subject, wherein: (i) the neurodegenerative condition is predicted to progress if the level or activity of cyclin F in the second sample is decreased relative to the level or activity of cyclin F in the first sample; or (ii) the neurodegenerative condition is not predicted to progress if the level or activity of cyclin F in the second sample is increased or unchanged relative to the level or activity of cyclin F in the first sample.

In an aspect, a method of monitoring the effectiveness of a therapy in reducing the progression of a neurodegenerative condition in a subject, comprises: (a) conducting at least one assay to determine the level or activity of cyclin F in a sample comprising motor neurons and/or cells that are surrogates for motor neurons (e.g., skin cells such as skin fibroblasts, blood cells such as peripheral blood mononuclear cells, etc.) from a subject having a neurodegenerative condition prior to and following administration of the therapy to the subject; and (b) comparing the level or activity of cyclin F in the sample from the subject prior to the administration of the therapy to the level or activity of cyclin F in the sample from the subject following administration of the therapy; and (c) monitoring the effectiveness of the therapy in reducing the progression of the neurodegenerative condition in the subject. In some embodiments, an increase in the level or activity of cyclin F in the sample following administration of the therapy as compared to the level or activity of cyclin F in the sample prior to the administration of the therapy is an indication that the therapy is effective in reducing the progression of the neurodegenerative condition in the subject. In some embodiments, a decrease in the level or activity of cyclin F in the sample from the subject following administration of the therapy as compared to the level or activity of cyclin F in the sample prior to the administration of the therapy is an indication that the therapy is not effective in reducing the progression of the neurodegenerative condition in the subject. In some embodiments, an absence of a change in the level or activity of cyclin F in the sample from the subject following administration of the therapy as compared to the level or activity of cyclin F in the sample prior to the administration of the therapy is an indication that the therapy is not effective in reducing the progression of the neurodegenerative condition in the subject.

Any suitable control can be used. In some embodiments, the control is a subject that does not have the neurodegenerative condition. In some embodiments, the control is a reference standard or level indicative of a subject that does not have the neurodegenerative condition. In some embodiments, the control is a reference standard or level indicative of a subject for which progression of the neurodegenerative condition is halted or reversed.

The disclosure contemplates using any assay that is capable of detecting the level or activity of cyclin F in a cell.

In some embodiments, the at least one assay comprises a substrate binding assay to detect the binding of cyclin F to TDP-43. Those skilled in the art will appreciate how to conduct substrate binding assays suitable for detecting the level or activity of cyclin F in a cell.

In some embodiments, the at least one assay comprises an assay that measures a level of cyclin F mRNA or cyclin F protein in a motor neuron or surrogate cell. Any assays that are capable of measuring mRNA or protein in a cell can be used (e.g., hybridization assays (e.g., microarrays, qRT-PCR, etc.), sequencing assays (e.g., serial analysis of gene expression (SAGE), cap analysis of gene expression (CAGE), massively parallel signature sequencing (MPSS), GRO-seq, and RNA-seq) and immunological based assays (e.g., Western blotting, immunohistochemistry, flow cytometry, etc.). It should be appreciated by the skilled artisan that increased levels of cyclin F mRNA and/or cyclin F protein in a motor neuron or surrogate cell relative to a control motor neuron or surrogate cell obtained from a subject that does not have the neurodegenerative condition or a reference standard or level is indicative that the subject has or is at risk for developing the neurodegenerative condition and/or a condition characterized by motor neuron degeneration.

In some embodiments, the methods further comprise selecting a subject suspected of having a neurodegenerative condition. In some embodiments, the diagnostic methods further comprise selecting a subject suspected of having a condition characterized by motor neuron degeneration.

Those skilled in the art will appreciate that the effectiveness of any therapy in reducing the progression of a neurodegenerative condition in a subject can be monitored in accordance with the methods described herein.

6. Methods of Treatment

Certain aspects of the present invention relate to methods for treating neurodegenerative conditions, and conditions characterized by motor neuron degeneration.

In an aspect, a method of treating or preventing a neurodegenerative condition in a subject in need thereof comprises administering to the subject an effective amount of an agent that enhances or increases the level or activity of cyclin F.

In an aspect, a method of treating or preventing a condition characterized by motor neuron degeneration in a subject in need thereof comprises administering to the subject an effective amount of an agent that enhances or increases the level or activity of cyclin F.

Suitably, the agent enhances or increases the level or activity of cyclin F and promotes motor neuron survival and/or inhibits motor neuron degeneration in the subject. In some embodiments, the agent enhances or increases the level or activity of cyclin F and ameliorates at least one symptom associated with the neurodegenerative condition in the subject. In some embodiments, the agent enhances or increases the level or activity of cyclin F and treats the subject's neurodegenerative condition. In some embodiments, the agent enhances or increases the level or activity of cyclin F and prevents the subject from developing a neurodegenerative condition. In some embodiments, the agent enhances or increases the level or activity of cyclin F and prevents the subject's neurodegenerative condition from progressing.

In some embodiments, the agent increases the level of a $SCF^{Cyclin\ F}$ complex comprising a substrate of the complex (e.g., TDP-43) and promotes motor neuron survival and/or inhibits motor neuron degeneration in the subject. In some embodiments, the agent increases the level of a $SCF^{Cyclin\ F}$ complex comprising a substrate of the complex (e.g., TDP-43) and ameliorates at least one symptom associated with the neurodegenerative condition in the subject. In some embodiments, the agent increases the level of a $SCF^{Cyclin\ F}$ complex comprising a substrate of the complex (e.g., TDP-43) and treats the subject's neurodegenerative condition. In some embodiments, the agent increases the level of a $SCF^{Cyclin\ F}$ complex comprising a substrate of the complex (e.g., TDP-43) and prevents the subject from developing a neurodegenerative condition. In some embodiments, the agent increases the level of a $SCF^{Cyclin\ F}$ complex comprising a substrate of the complex (e.g., TDP-43) and prevents the subject's neurodegenerative condition from progressing.

In some embodiments, the agent decreases the amount of a protein that is susceptible to protein aggregation (e.g., TDP-43) and promotes motor neuron survival and/or inhibits motor neuron degeneration in the subject. In some embodiments, the agent decreases the amount of a protein that is susceptible to protein aggregation (e.g., TDP-43) and ameliorates at least one symptom associated with the neurodegenerative condition in the subject. In some embodiments, the agent decreases the amount of a protein that is susceptible to protein aggregation (e.g., TDP-43) and treats the subject's neurodegenerative condition. In some embodiments, the agent decreases the amount of a protein that is susceptible to protein aggregation (e.g., TDP-43) and prevents the subject from developing a neurodegenerative condition. In some embodiments, the agent decreases the amount of a protein that is susceptible to protein aggregation (e.g., TDP-43) and prevents the subject's neurodegenerative condition from progressing.

Any agent that level or activity of cyclin F can be used in the embodiments described herein.

In some embodiments, the subject is a human.

In some embodiments, the subject selected for treatment of a neurodegenerative condition, or a condition characterized by motor neuron degeneration. In some embodiments, the subject is at risk of developing a neurodegenerative condition, or a condition characterized by motor neuron degeneration. In some embodiments, the subject is suspected of having a neurodegenerative condition, or a condition characterized by motor neuron degeneration. In some embodiments, the subject is suffering from a neurodegenerative condition. The neurodegenerative condition can be any neurodegenerative condition described herein. In some embodiments, the neurodegenerative condition is marked by motor neuron degeneration. In some embodiments, the neurodegenerative condition is a motor neuron disease. In some embodiments, the neurodegenerative condition is characterized by a reduced or abnormally low level or activity of cyclin F in motor neurons. In some embodiments, the neurodegenerative condition is ALS. In some embodiments, the neurodegenerative condition is FTD.

In some embodiments, another therapeutic agent is also administered to the subject. Such another therapeutic or "ancillary" agent is typically administered concurrently with the cyclin F-enhancing agent. For example, the therapeutic agent can be administered in the same formulation or in separate formulations Ex e.g., Butyrates, Valproic acid, Hydroxyurea or Riluzole. In some embodiments, the agents described herein are used in combination with another therapeutic agent suitable for use in treating one or more symptoms of ALS, including, but not limited to, one or more of (i) hydrogenated pyrido [4,3-b] indoles or pharmaceutically acceptable salts thereof and (ii) agents that promote or increase the supply of energy to muscle cells, COX-2 inhibitors, poly(ADP-ribose)polymerase-1 (PARP-I) inhibitors, 30S ribosomal protein inhibitors, NMDA antagonists, NMDA receptor antagonists, sodium channel blockers, glutamate release inhibitors, K(V)4.3 channel blockers, anti-inflammatory agents, 5-HT1A receptor agonists, neurotrophic factor enhancers, agents that promote motoneuron phenotypic survival and/or neuritogenesis, agents that protect the blood brain barrier from disruption, inhibitors of the production or activity of one or more proinflammatory cytokines, immunomodulators, neuroprotectants, modulators of the function of astrocytes, antioxidants (such as small molecule catalytic antioxidants), free radical scavengers, agents that decrease the amount of one or more reactive oxygen species, agents that inhibit the decrease of non-protein thiol content, stimulators of a normal cellular protein repair pathway (such as agents that activate molecular chaperones), neurotrophic agents, inhibitors of nerve cell death, stimulators of neurite growth, agents that prevent the death of nerve cells and/or promote regeneration of damaged brain tissue, cytokine modulators, agents that reduce the level of activation of microglial cells, cannabinoid CB1 receptor ligands, nonsteroidal anti-inflammatory drugs, cannabinoid CB2 receptor ligands, creatine, creatine derivatives, stereoisomers of a dopamine receptor agonist such as pramipexole hydrochloride, ciliary neurotrophic factors, agents that encode a ciliary neurotrophic factor, glial derived neurotrophic factors, agents that encode a glial derived neurotrophic factor, neurotrophin 3, agents that encode neurotrophin 3, or any combination thereof.

In some embodiments, the agents described herein are used in combination with another therapeutic agent suitable for use in treating one or more symptoms of ALS or FTD, including, but not limited to, one or more of antibiotics (e.g., Aminoglycosides, Cephalosporins, Chloramphenicol, Clindamycin, Erythromycins, Fluoroquinolones, Macrolides, Azolides, Metronidazole, Penicillins, Tetracyclines, Trimethoprim-sulfamethoxazole, Vancomycin), steroids (e.g., Andranes (e.g., Testosterone), Cholestanes (e.g., Cholesterol), Cholic acids (e.g., Cholic acid), Corticosteroids (e.g., Dexamethasone), Estraenes (e.g., Estradiol), Pregnanes (e.g., Progesterone), narcotic and non-narcotic analgesics (e.g., Morphine, Codeine, Heroin, Hydromorphone, Levorphanol, Meperidine, Methadone, Oxydone, Propoxyphene, Fentanyl, Methadone, Naloxone, Buprenorphine, Butorphanol, Nalbuphine, Pentazocine), anti-inflammatory agents (e.g., Alclofenac, Alclometasone Dipropionate, Algestone Acetonide, alpha Amylase, Amcinafal, Amcinafide, Amfenac Sodium, Amiprilose Hydrochloride, Anakinra, Anirolac, Anitrazafen, Apazone, Balsalazide Disodium, Bendazac, Benoxaprofen, Benzydamine Hydrochloride, Bromelains, Broperamole, Budesonide, Carprofen, Cicloprofen, Cintazone, Cliprofen, Clobetasol Propionate, Clobetasone Butyrate, Clopirac, Cloticasone Propionate, Cormethasone Acetate, Cortodoxone, Decanoate, Deflazacort, Delatestryl, Depo-Testosterone, Desonide, Desoximetasone, Dexamethasone Dipropionate, Diclofenac Potassium, Diclofenac Sodium, Diflorasone Diacetate; Diflumidone Sodium, Diflunisal, Difluprednate, Diftalone, Dimethyl Sulfoxide, Drocinonide, Endrysone, Enlimomab, Enolicam Sodium, Epirizole, Etodolac, Etofenamate, Felbinac, Fenamole, Fenbufen, Fenclofenac, Fenclorac, Fendosal, Fenpipalone, Fentiazac, Flazalone, Fluazacort, Flufenamic Acid, Flumizole, Flunisolide Acetate, Flunixin, Flunixin Meglumine, Fluocortin Butyl, Fluorometholone Acetate, Fluquazone, Flurbiprofen, Fluretofen, Fluticasone Propionate, Furaprofen, Furobufen, Halcinonide, Halobetasol Propionate, Halopredone Acetate, Ibufenac, Ibuprofen, Ibuprofen Aluminum, Ibuprofen Piconol, Ilonidap, Indomethacin, Indomethacin Sodium, Indoprofen, Indoxole, Intrazole, Isoflupredone Acetate, Isoxepac, Isoxicam, Ketoprofen, Lofemizole Hydrochloride, Lomoxicam, Loteprednol Etabonate, Meclofenamate Sodium, Meclofenamic Acid, Meclorisone Dibutyrate, Mefenamic Acid, Mesalamine, Meseclazone, Mesterolone, Methandrostenolone, Methenolone, Methenolone Acetate, Methylprednisolone Suleptanate, Morniflumate, Nabumetone, Nandrolone, Naproxen, Naproxen Sodium, Naproxol, Nimazone, Olsalazine Sodium, Orgotein, Orpanoxin, Oxandrolane, Oxaprozin, Oxyphenbutazone, Oxymetholone, Paranyline Hydrochloride, Pentosan Polysulfate Sodium, Phenbutazone Sodium Glycerate, Pirfenidone, Piroxicam, Piroxicam Cinnamate, Piroxicam Olamine, Pirprofen, Prednazate, Prifelone, Prodolie Acid, Proquazone, Proxazole, Proxazole Citrate, Rimexolone, Romazarit, Salcolex, Salnacedin, Salsalate, Sanguinarium Chloride, Seclazone, Sermetacin, Stanozolol, Sudoxicam, Sulindac, Suprofen, Talmetacin, Talniflumate, Talosalate, Tebufelone, Tenidap, Tenidap Sodium, Tenoxicam, Tesicam, Tesimide, Testosterone, Testosterone Blends, Tetrydamine, Tiopinac, Tixocortol Pivalate, Tolmetin, Tolmetin Sodium, Triclonide, Triflumidate, Zidometacin, Zomepirac Sodium), or anti-histaminic agents (e.g., Ethanolamines (like diphenhydrmine carbinoxamine), Ethylenediamine (like tripelennamine pyrilamine), Alkylamine (like chlorpheniramine, dexchlorpheniramine, brompheniramine, triprolidine), other anti-histamines like astemizole, loratadine, fexofenadine, Bropheniramine, Clemastine, Acetaminophen, Pseudoephedrine, Triprolidine).

In one aspect, the invention features a kit comprising an agent identified by the method described herein, and instructions to treat a neurodegenerative condition e.g. ALS or FTD using a method described herein.

7. Formulations and Administration

For administration to a subject, the agents described herein can be administered orally, parenterally, for example, subcutaneously, intravenously, intramuscularly, intraperitoneally, by intranasal instillation, or by application to mucous membranes, such as, that of the nose, throat, and bronchial tubes. One method for targeting the nervous system, such as spinal cord glia, is by intrathecal delivery. The targeted agent is released into the surrounding CSF and/or tissues and the released compound can penetrate into the spinal cord parenchyma, just after acute intrathecal injections. For a comprehensive review on drug delivery strategies including CNS delivery, see Ho et al., Curr. Opin. Mol. Ther. (1999), 1:336-3443; Groothuis et al., J. Neuro Virol. (1997), 3:387-400; and Jan, Drug Delivery Systmes: Technologies and Commercial Opportunities, Decision Resources, 1998, content of all which is incorporate herein by reference.

They can be administered alone or with suitable pharmaceutical carriers, and can be in solid or liquid form such as, tablets, capsules, powders, solutions, suspensions, or emulsions.

The agents can be formulated in pharmaceutically acceptable compositions which comprise an effective amount of the agent, formulated together with one or more pharmaceutically acceptable carriers (additives) and/or diluents. The agents can be specially formulated for administration in solid or liquid form, including those adapted for the following: (1) oral administration, for example, drenches (aqueous or non-aqueous solutions or suspensions), lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) transmucosally; or (9) nasally. Additionally, compounds and/or agents can be implanted into a patient or injected using a drug delivery system. See, for example, Urquhart, et al. (1984. *Ann. Rev. Pharmacol. Toxicol.* 24: 199-236); Lewis, ed. "Controlled Release of Pesticides and Pharmaceuticals" (Plenum Press, New York, 1981); U.S. Pat. Nos. 3,773,919; and 353,270,960.

Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other nontoxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

Pharmaceutically-acceptable antioxidants include, but are not limited to, (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lectitin, propyl gallate, alpha-tocopherol, and the like; and (3) metal chelating agents, such as citric acid, ethylenediamine tetraacetic acid (EDTA), sorbitol, tartaric acid, phosphoric acids, and the like.

PEG includes within it scope any ethylene glycol polymer that contains about 20 to about 2000000 linked monomers, typically about 50-1000 linked monomers, usually about 100-300. Polyethylene glycols include PEGs containing various numbers of linked monomers, e.g., PEG20, PEG30, PEG40, PEG60, PEG80, PEG100, PEG115, PEG200, PEG 300, PEG400, PEG500, PEG600, PEG1000, PEG1500, PEG2000, PEG3350, PEG4000, PEG4600, PEG5000, PEG6000, PEG8000, PEG11000, PEG12000, PEG2000000 and any mixtures thereof.

The agents can be formulated in a gelatin capsule, in tablet form, dragee, syrup, suspension, topical cream, suppository, injectable solution, or kits for the preparation of syrups, suspension, topical cream, suppository or injectable solution just prior to use. Also, compounds and/or agents can be included in composites, which facilitate its slow release into the blood stream, e.g., silicon disc, polymer beads.

The formulations can conveniently be presented in unit dosage form and may be prepared by any of the methods well known in the art of pharmacy. Techniques, excipients and formulations generally are found in, e.g., Remington's Pharmaceutical Sciences, Mack Publishing Co., Easton, Pa. 1985, 17th edition, Nema et al., PDA J. Pharm. Sci. Tech. 1997 51:166-171. Methods to make invention formulations include the step of bringing into association or contacting an active agent with one or more excipients or carriers. In general, the formulations are prepared by uniformly and intimately bringing into association one or more agents with liquid excipients or finely divided solid excipients or both, and then, if appropriate, shaping the product.

The preparative procedure may include the sterilization of the pharmaceutical preparations. The agents may be mixed with auxiliary agents such as lubricants, preservatives, stabilizers, salts for influencing osmotic pressure, etc., which do not react deleteriously with the agents.

Examples of injectable form include solutions, suspensions and emulsions. Injectable forms also include sterile powders for extemporaneous preparation of injectable solutions, suspensions or emulsions. The agents of the present invention can be injected in association with a pharmaceutical carrier such as normal saline, physiological saline, bacteriostatic water, Cremophor™ EL (BASF, Parsippany, N.J.), phosphate buffered saline (PBS), Ringer's solution, dextrose solution, ethanol, polyol (e.g., glycerol, propylene glycol, and liquid polyethylene glycol), vegetable oils, and suitable mixtures thereof, and other aqueous carriers known in the art. Appropriate non-aqueous carriers may also be used and examples include fixed oils and ethyl oleate. In all cases, the composition must be sterile and should be fluid to the extent that easy syringability exists. It must be stable under the conditions of manufacture and storage and must be preserved against the contaminating action of microorganisms such as bacteria and fungi. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions can be brought about by including in the composition an agent which delays absorption, for example, aluminum monostearate and gelatin. A suitable carrier is 5% dextrose in saline. Frequently, it is desirable to include additives in the carrier such as buffers and preservatives or other substances to enhance isotonicity and chemical stability.

In some embodiments, agents described herein can be administrated encapsulated within liposomes. The manufacture of such liposomes and insertion of molecules into such liposomes being well known in the art, for example, as described in U.S. Pat. No. 4,522,811. Liposomal suspensions (including liposomes targeted to particular cells, e.g., a pituitary cell) can also be used as pharmaceutically acceptable carriers.

In one embodiment, the agents are prepared with carriers that will protect the compound and/or agent against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc.

In the case of oral ingestion, excipients useful for solid preparations for oral administration are those generally used in the art, and the useful examples are excipients such as lactose, sucrose, sodium chloride, starches, calcium carbonate, kaolin, crystalline cellulose, methyl cellulose, glycerin, sodium alginate, gum arabic and the like, binders such as polyvinyl alcohol, polyvinyl ether, polyvinyl pyrrolidone, ethyl cellulose, gum arabic, shellac, sucrose, water, ethanol, propanol, carboxymethyl cellulose, potassium phosphate and the like, lubricants such as magnesium stearate, talc and the like, and further include additives such as usual known coloring agents, disintegrators such as alginic acid and PRIMOGEL™, and the like.

The agents can be orally administered, for example, with an inert diluent, or with an assimilable edible carrier, or they may be enclosed in hard or soft shell capsules, or they may be compressed into tablets, or they may be incorporated directly with the food of the diet. For oral therapeutic administration, these compounds and/or agents may be incorporated with excipients and used in the form of tablets, capsules, elixirs, suspensions, syrups, and the like. Such compositions and preparations should contain at least 0.1% of compound and/or agent. The percentage of the agent in these compositions may, of course, be varied and may conveniently be between about 2% to about 60% of the weight of the unit. The amount of compound and/or agent in such therapeutically useful compositions is such that a suitable dosage will be obtained. Preferred compositions according to the present invention are prepared so that an oral dosage unit contains between about 100 and 2000 mg of compound and/or agent.

Examples of bases useful for the formulation of suppositories are oleaginous bases such as cacao butter, polyethylene glycol, lanolin, fatty acid triglycerides, witepsol (trademark, Dynamite Nobel Co. Ltd.) and the like. Liquid preparations may be in the form of aqueous or oleaginous suspension, solution, syrup, elixir and the like, which can be prepared by a conventional way using additives.

The compositions can be given as a bolus dose, to maximize the circulating levels for the greatest length of time after the dose. Continuous infusion may also be used after the bolus dose.

The agents can also be administered directly to the airways in the form of an aerosol. For administration by inhalation, the agents in solution or suspension can be delivered in the form of an aerosol spray from pressured container or dispenser which contains a suitable propellant, e.g., a gas such as carbon dioxide, or hydrocarbon propellant like propane, butane or isobutene. The agents can also be administered in a no-pressurized form such as in an atomizer or nebulizer.

The agents can also be administered parenterally. Solutions or suspensions of these agents can be prepared in water suitably mixed with a surfactant, such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions. Under ordinary conditions of storage and use, these preparations contain a preservative to prevent the growth of microorganisms.

It may be advantageous to formulate oral or parenteral compositions in dosage unit form for ease of administration and uniformity of dosage.

Administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the agents are formulated into ointments, salves, gels, or creams as generally known in the art.

The agents can be administrated to a subject in combination with other pharmaceutically active agents. Exemplary pharmaceutically active compounds and/or agents include, but are not limited to, those found in Harrison's Principles of Internal Medicine, 13.sup.th Edition, Eds. T. R. Harrison et al. McGraw-Hill N.Y., N.Y.; Physician's Desk Reference, 50.sup.th Edition, 1997, Oradell N.J., Medical Economics Co.; Pharmacological Basis of Therapeutics, 8.sup.th Edition, Goodman and Gilman, 1990; United States Pharmacopeia, The National Formulary, USP XII NF XVII, 1990, the complete contents of all of which are incorporated herein by reference. In some embodiments, the pharmaceutically active agent is selected from the group consisting of butyrates, valproic acid, hydroxyurea and Riluzole.

The agents and the other pharmaceutically active agent can be administrated to the subject in the same pharmaceutical composition or in different pharmaceutical compositions (at the same time or at different times). For example, an Aurora kinase inhibitor and an additional agent for treating a neurodegenerative condition can be administrated to the subject in the same pharmaceutical composition or in different pharmaceutical compositions (at the same time or at different times).

The amount of agent which can be combined with a carrier material to produce a single dosage form will generally be that amount of the agent which produces a therapeutic effect. Generally, out of one hundred percent, this amount will range from about 0.1% to 99% of compound, preferably from about 5% to about 70%, most preferably from 10% to about 30%.

The tablets, capsules, and the like may also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, or saccharin. When the dosage unit form is a capsule, it may contain, in addition to materials of the above type, a liquid carrier, such as a fatty oil.

Various other materials may be present as coatings or to modify the physical form of the dosage unit. For instance, tablets may be coated with shellac, sugar, or both. A syrup may contain, in addition to the active ingredient, sucrose as a sweetening agent, methyl and propylparabens as preservatives, a dye, and flavoring such as cherry or orange flavor.

The pharmaceutical compositions can be included in a container, pack, or dispenser together with instructions for administration.

Guidance regarding the efficacy and dosage which will deliver an effective amount of a compound and/or agent to treat ALS or FTD can be obtained from animal models of ALS or FTD, see e.g., those described in Hsieh-Li et al. (2000. *Nature Genetics* 24:66-70) and references cited therein.

Toxicity and therapeutic efficacy can be determined by standard pharmaceutical procedures in cell cultures or experimental animals, e.g., for determining the LD50 (the dose lethal to 50% of the population) and the ED50 (the dose effective in 50% of the population). The dose ratio between toxic and therapeutic effects is the therapeutic index and it can be expressed as the ratio LD50/ED50. Compositions that exhibit large therapeutic indices, are preferred.

The data obtained from the cell culture assays and animal studies can be used in formulating a range of dosage for use in humans. The dosage of such compounds and/or agents lies preferably within a range of circulating concentrations that include the ED50 with little or no toxicity. The dosage may vary within this range depending upon the dosage form employed and the route of administration utilized.

The effective dose can be estimated initially from cell culture assays. A dose may be formulated in animal models to achieve a circulating plasma concentration range that includes the IC50 (i.e., the concentration of the therapeutic which achieves a half-maximal inhibition of symptoms) as determined in cell culture. Levels in plasma may be measured, for example, by high performance liquid chromatography. The effects of any particular dosage can be monitored by a suitable bioassay. Examples of suitable bioassays include DNA replication assays, transcription based assays, GDF-8 binding assays, and immunological assays.

The dosage may be determined by a physician and adjusted, as necessary, to suit observed effects of the treatment. Generally, the compositions are administered so that the compound and/or agent is given at a dose from 1 µg/kg to 100 mg/kg, 1 µg/kg to 50 mg/kg, 1 µg/kg to 20 mg/kg, 1 µg/kg to 10 mg/kg, 1 µg/kg to 1 mg/kg, 100 µg/kg to 100 mg/kg, 100 µg/kg to 50 mg/kg, 100 µg/kg to 20 mg/kg, 100 µg/kg to 10 mg/kg, 100 µg/kg to 1 mg/kg, 1 mg/kg to 100 mg/kg, 1 mg/kg to 50 mg/kg, 1 mg/kg to 20 mg/kg, 1 mg/kg to 10 mg/kg, 10 mg/kg to 100 mg/kg, 10 mg/kg to 50 mg/kg, or 10 mg/kg to 20 mg/kg. For antibody compounds and/or agents, one preferred dosage is 0.1 mg/kg of body weight (generally 10 mg/kg to 20 mg/kg). If the antibody is to act in the brain, a dosage of 50 mg/kg to 100 mg/kg is usually appropriate.

With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment or make other alteration to treatment regimen. The dosing schedule can vary from once a week to daily depending on a number of clinical factors, such as the subject's sensitivity to the polypeptides. The desired dos can be administered at one time or divided into subdoses, e.g., 2-4 subdoses and administered over a period of time, e.g., at appropriate intervals through the day or other appropriate schedule. Such sub-doses can be administered as unit dosage forms. Examples of dosing schedules are administration once a week, twice a week, three times a week, daily, twice daily, three times daily or four or more times daily.

8. Kits

An agent described herein can be provided in a kit. The kit includes (a) the agent, e.g., a composition that includes the agent, and (b) informational material. The informational material can be descriptive, instructional, marketing or other material that relates to the methods described herein and/or the use of the agent for the methods described herein. For example, the informational material describes methods for administering the agent to promote motor neuron survival, treat or prevent a neurodegenerative condition (e.g., ALS or FTD), or at least one symptom of the neurodegenerative condition, or a condition associated with dysfunctional or decreases motor neurons.

In one embodiment, the informational material can include instructions to administer the agent in a suitable manner, e.g., in a suitable dose, dosage form, or mode of administration (e.g., a dose, dosage form, or mode of administration described herein). In another embodiment, the informational material can include instructions for identifying a suitable subject, e.g., a human, e.g., an adult human. The informational material of the kits is not limited in its form. In many cases, the informational material, e.g., instructions, is provided in printed matter, e.g., a printed text, drawing, and/or photograph, e.g., a label or printed sheet. However, the informational material can also be provided in other formats, such as Braille, computer readable material, video recording, or audio recording. In another embodiment, the informational material of the kit is a link or contact information, e.g., a physical address, email address, hyperlink, website, or telephone number, where a user of the kit can obtain substantive information about the modulator and/or its use in the methods described herein. Of course, the informational material can also be provided in any combination of formats.

In addition to the agent, the composition of the kit can include other ingredients, such as a solvent or buffer, a stabilizer or a preservative, and/or a second agent for treating a condition or disorder described herein, e.g. increased pancreatic islet mass. Alternatively, the other ingredients can be included in the kit, but in different compositions or containers than the agent. In such embodiments, the kit can include instructions for admixing the agent and the other ingredients, or for using the agent together with the other ingredients.

The agent can be provided in any form, e.g., liquid, dried or lyophilized form. It is preferred that the agent be substantially pure and/or sterile. When the agent is provided in a liquid solution, the liquid solution preferably is an aqueous solution, with a sterile aqueous solution being preferred. When the compound and/or agent is provided as a dried form, reconstitution generally is by the addition of a suitable solvent. The solvent, e.g., sterile water or buffer, can optionally be provided in the kit.

The kit can include one or more containers for the composition containing the compound and/or agent. In some embodiments, the kit contains separate containers, dividers or compartments for the agent (e.g., in a composition) and informational material. For example, the agent (e.g., in a composition) can be contained in a bottle, vial, or syringe, and the informational material can be contained in a plastic sleeve or packet. In other embodiments, the separate elements of the kit are contained within a single, undivided container. For example, the agent (e.g., in a composition) is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of the agent (e.g., in a composition). For example, the kit includes a plurality of syringes, ampules, foil packets, or blister packs, each containing a single unit dose of the agent. The containers of the kits can be air tight and/or waterproof.

The compound and/or agent (e.g., in a composition) can be administered to a subject, e.g., an adult subject, e.g., a subject in need of motor neurons. The method can include evaluating a subject, e.g., to evaluate motor neuron survival, and thereby identifying a subject as having decreased motor neurons or being pre-disposed to motor neuron death or dysfunction.

In order that the invention may be readily understood and put into practical effect, particular preferred embodiments will now be described by way of the following non-limiting examples.

EXPERIMENTAL

BioID and IP Identifies Endogenous TDP-43 as an Interaction Partner of Cyclin F

Endogenous proteins were labeled by BioID-Cyclin F in live HEK293 cells (FIG. 1). Biotinylated proteins were purified using streptavidin beads, trypsin digested and identified using mass spectrometry. A label free approach was used to identify proteins that were in common between BioID/MS and IP/MS. Proteins that bound to an IgG control were considered as protein contaminants. Using this approach it was possible to identify stable interactors of Cyclin F (Skp1 and Cul1) that are required for ubiquitin ligase activity. In addition peptides belonging to TAR DNA-binding protein of 43 kDa (TDP43) were noted and this result was validated using immunoblotting (FIG. 1).

Figure 2:
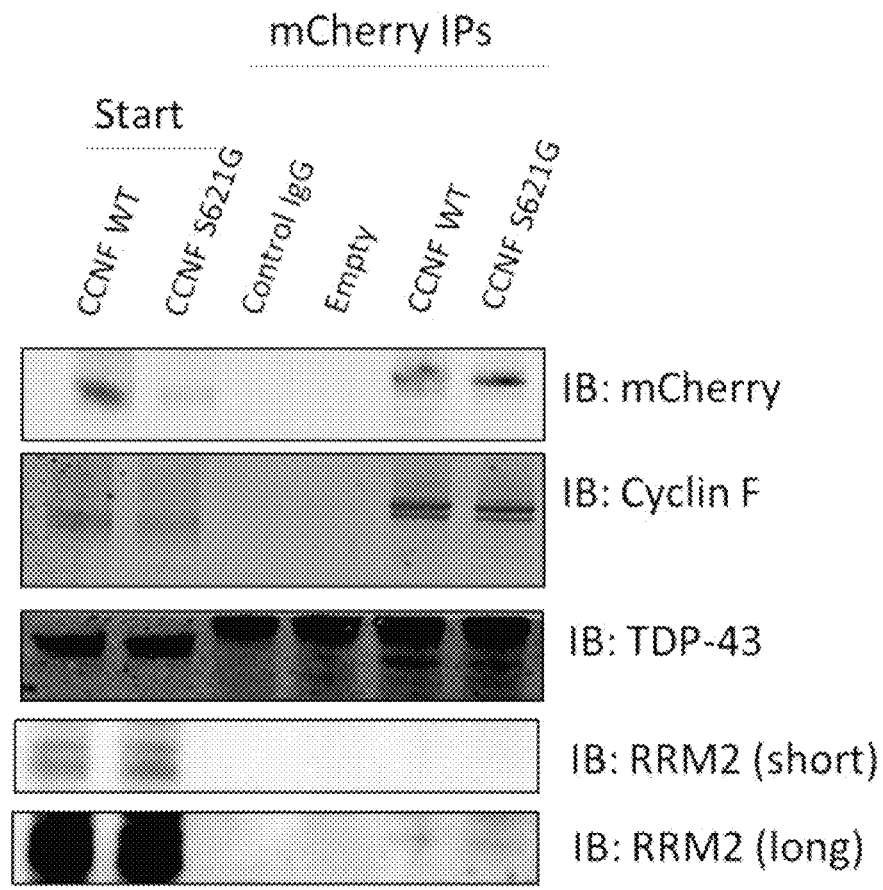
FIG. 2 is a photgraphic representation demonstrating that Cyclin F co-immunoprecipitates TDP-43 in HEK and neuron-like cells. A. mCherry-Cyclin F co-immunoprecipitates endogenous TDP-43 in Neuro2A cells. B. Cyclin F-flag co-immunoprecipitates overexpressed TDP-43-HA in HEK293 cells. C. TDP-43 immunoprecipitates with mCherry-Cyclin $F^{WT}$ and mCherry-Cyclin $F^{S621G}$ in Neuro2A cells.
Figure 2:
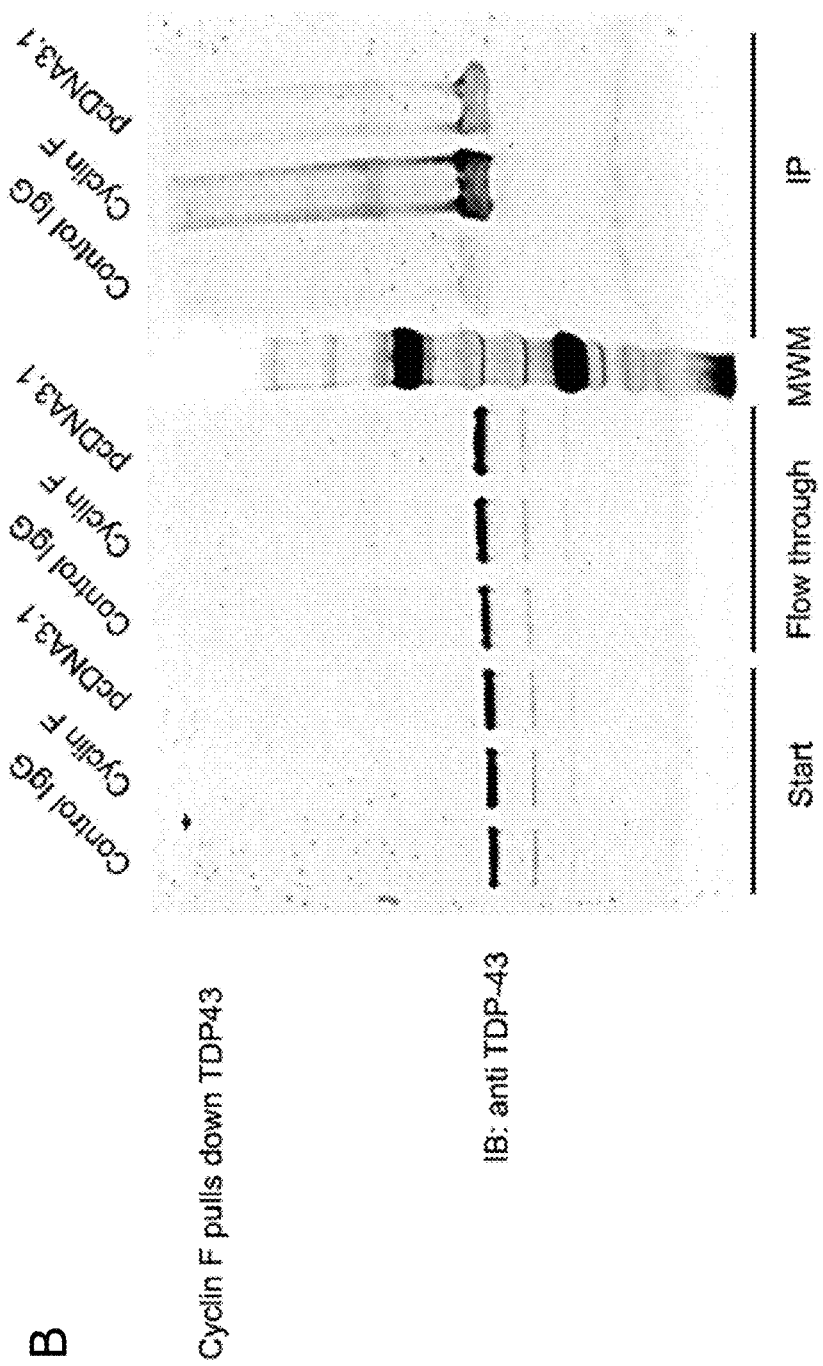
Figure 2:
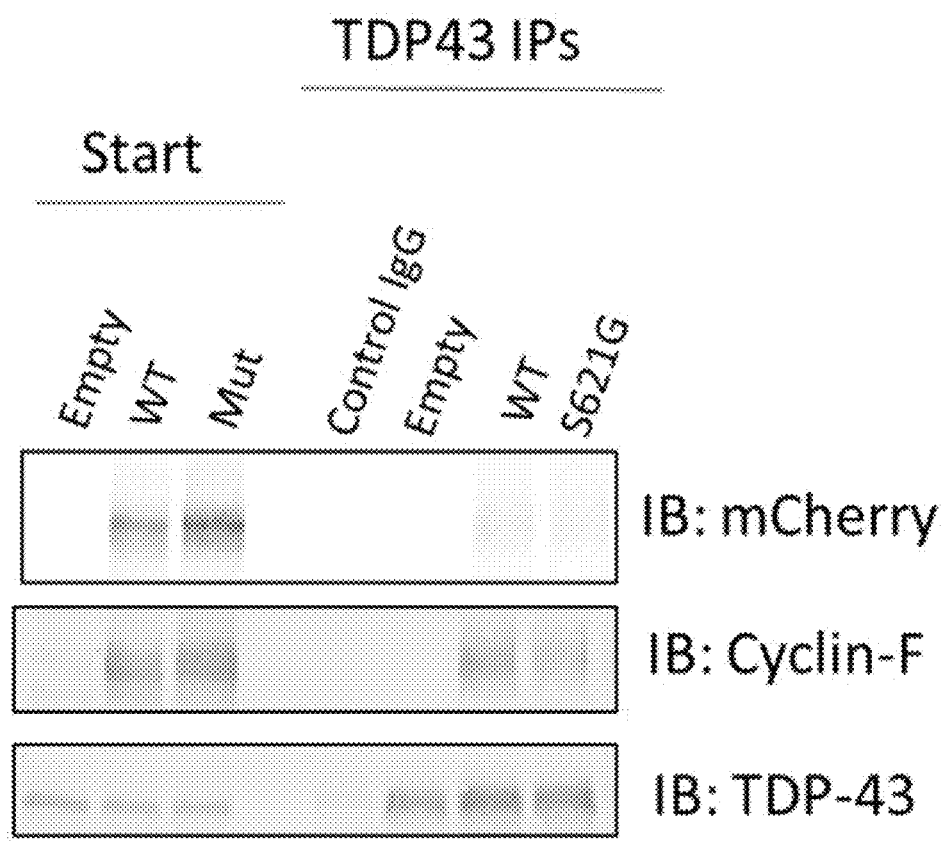

The interaction between Cyclin F and TDP-43 was further validated using a classic immunoprecipitation approach in HEK293 and Neuro2a cells. Cyclin F-flag and TDP43-HA were co-transfected into HEK293 cells. Immunoprecipitation of Cyclin F using anti-flag M2 antibodies revealed TDP-43 co-immunoprecipitated with Cyclin F-flag (FIG. 2). Furthermore Cyclin F-mCherry was able to co-immunoprecipitate with endogenous TDP-43 in neuron-like Neuro2a cells, and TDP-43 was able to co-immunoprecipitate Cyclin F-mCherry (FIG. 2).

Cyclin F Regulates the Intracellular Levels of TDP43

Figure 3:
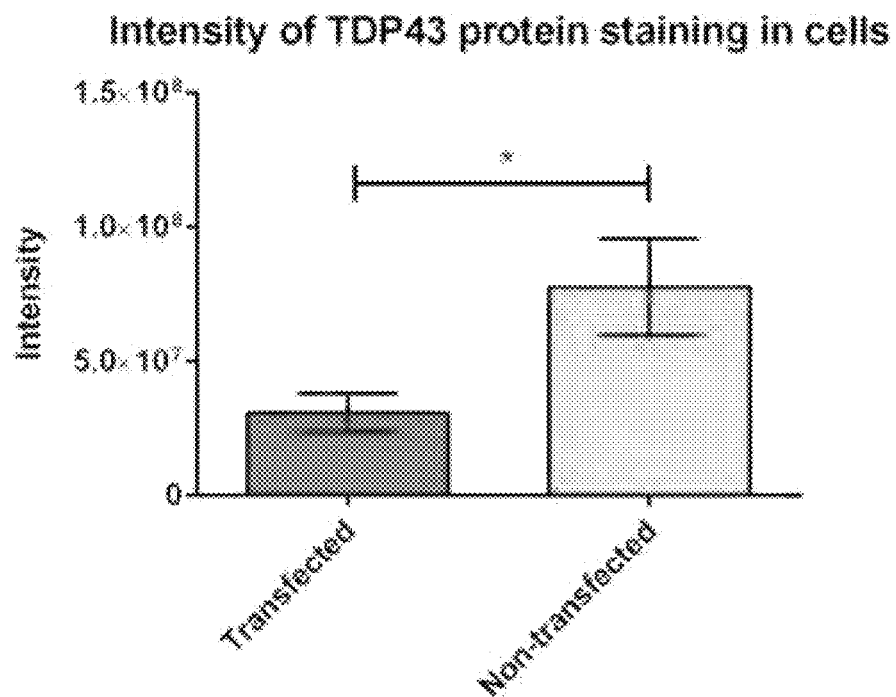
FIG. 3 is a graphical and photographic representation showing that TDP-43 and Cyclin F co-localize in the nucleus of HEK293 cells. Cells overexpressing Cyclin F show a decrease in TDP-43 staining.
Figure 3:
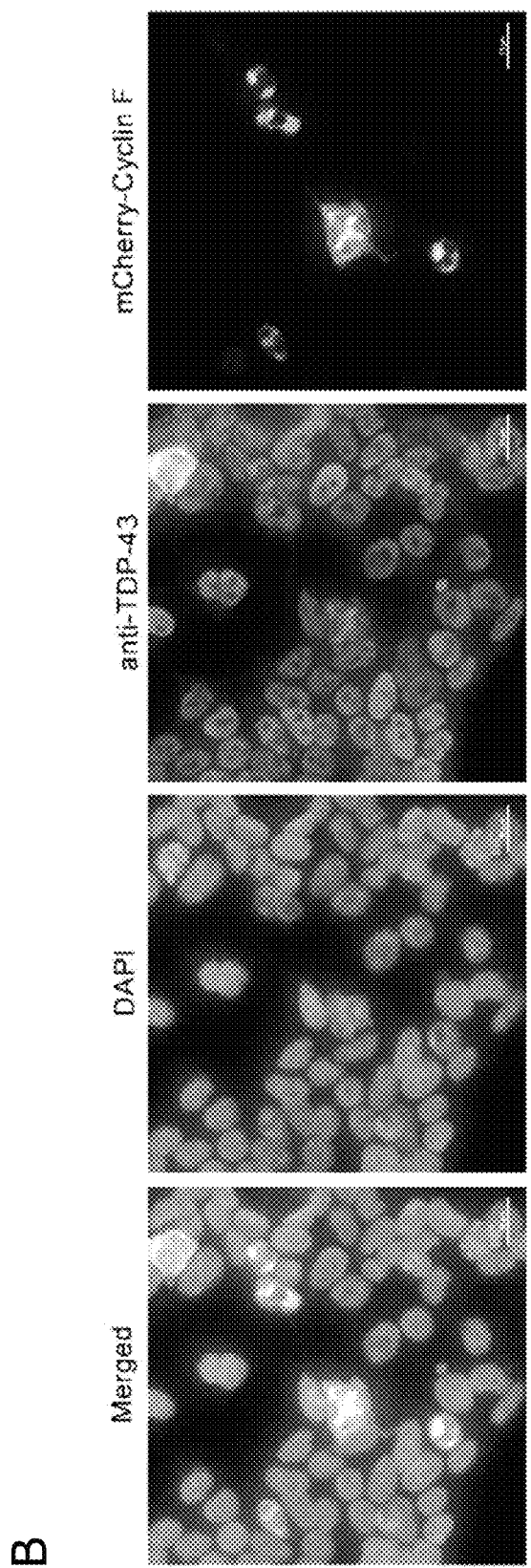
Figure 4:
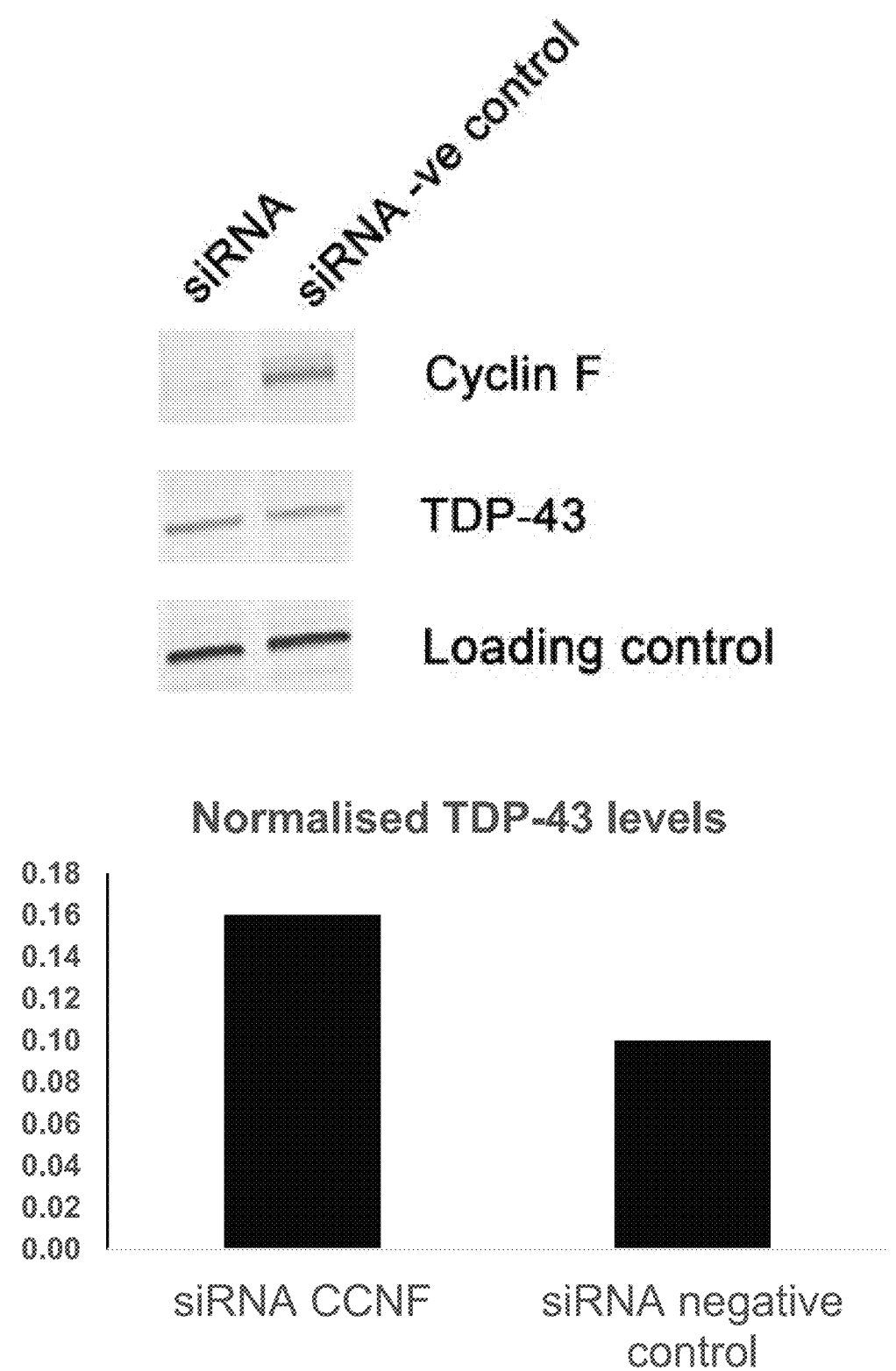
FIG. 4 is a photographic and graphical representation showing that cells with siRNA-mediated reduction in Cyclin F expression have greater TDP-43 expression compared to a negative control.
Figure 5:
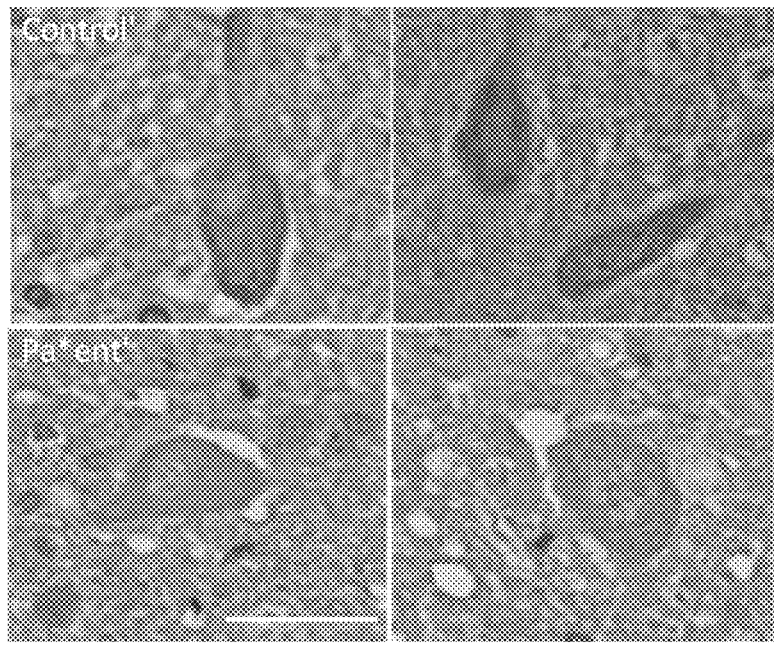
FIG. 5 is a photographic representation showing that substantially less Cyclin F is observed in motor neurons of a sporadic MND patient as compared to a healthy control. Postmortem patient spinal cord tissue is immuno labeled for Cyclin F (brown) and nucleus (blue).

TDP-43 was stably over-expressed in T-REx Flp-In HEK293 cells, resulting in substantial levels of intracellular TDP43. When mCherry-Cyclin F was transiently transfected into these cells (such that only some cells express mCherry-Cyclin F), it was found that lower TDP-43 intensity was present in cells co-expressing mCherry-Cyclin F (FIG. 3). Conversely, when endogenous Cyclin F was silenced (using siRNA) in the stably transfected TDP43 T-REx Flp-In HEK293 cells, the level of TDP-43 was increased compared to the non-siRNA effected cells (negative control) (FIG. 4). In sporadic ALS patient tissue, lower levels of Cyclin F expression were observed in motor neurons in comparison to healthy control tissue (FIG. 5).

Materials and Methods

BioID

Briefly, a gene encoding FLAG-BirA*-Cyclin F was cloned into the pcDNA5/FRT/TO expression vector. HEK293 cells stably expressing FLAG-BirA*-Cyclin F were generated using the Flp-In T-Rex system (Invitrogen). Stably transfected cells were selected in DMEM containing 10% FBS, antibiotics (100 mg/mL streptomycin and 100 U/mL penicillin) and 200 µg/mL of Hygromycin B Gold (InvivoGen) and kept in a 37° C. incubator with 5% $CO_2$ and 95% humidity. For gene expression and biotinylation of endogenous proteins, 1 µg/mL of tetracycline (Sigma) and 50 µg/mL of biotin (Sigma) were simultaneously added to cell culture media. After 24 hours, cells were harvested in ice-cold PBS and pelleted at 3000×g for 3 min. Pellets were washed twice with PBS and snap frozen at −80° C. Cell pellets were lysed in modified RIPA lysis buffer (50 mM Tris-HCl pH 7.5, 150 mM NaCl, 1 mM EDTA, 1 mM EGTA, 1% Triton X-100, 0.1% SDS, turbonuclease and protease inhibitor cocktail (Roche)) for 1 hour at 4° C., then probe sonicated (10 s, Setting 3, Branson Sonifier 450) to disrupt protein aggregates. Lysates were centrifuged at 35,000×g for 30 mins. Supernatant was incubated with streptavidin-coupled magnetic beads (GE Healthcare) for 3 hr at 4° C. Magnetic beads were re-captured using a magnet and then washed six times in 50 mM ammonium biocarbonate (pH 8.3). Proteins captured by the beads were reduced in 10 mM dithiothreitol for 30 min at 50° C. For alkylation, 25 mM of iodoacetamide was added to cell lysates at room temperature. Samples were kept in the dark for 30 min. Once alkylated, samples were subject to trypsin digestion (sequencing grade modified trypsin, Promega) at 37° C. overnight. Supernatant containing tryptic peptides were collected and dried down. Lyophilized peptides were re-suspended in 0.1% formic acid and analyzed using MS.

FLAG and mCherry Affinity Purification

Either HEK293 or Neuro-2A cells were transfected with constructs encoding mCherry-Cyclin F, Flag-Cyclin For TDP-43-HA using Lipofectamine 2000. Transfected cells were harvested after 24 hours and cell pellets were resuspended in NP40 lysis buffer (1% (v/v) Nonidet P-40, Tris-buffered saline (TBS), 2 mM EDTA, cOmplete protease inhibitor cocktail and phosSTOP (Roche)). Cell resuspensions were probe sonicated (10 s, Setting 3, Branson Sonifier 450) to disrupt protein aggregates. Resulting lysates were centrifuged at 14,000×g for 30 mins to remove cell debris. A 500 µg aliquot of each supernatant was incubated with either 2 µg of anti-FLAG M2 (Sigma), 1 µg of anti-mCherry (Clontech) or 1 µg of anti-TDP43 (Abnova) for 1 hr at 4° C. To capture the antibody-protein complex, supernatants were incubated with Protein A/G magnetic beads (Pierce) at 4° C. for 2 hr. Beads were collected using a magnet and washed three times in NP40 lysis buffer. For western blot analysis, beads were resuspended in 1×LDS buffer containing 30 mM DTT and boiled at 95° C. for 5 min.

SDS PAGE and Immunoblotting

Equal amount of protein was separated on a 4-12% Bis-Tris SDS PAGE gel. Proteins were transferred onto a nitrocellulose membrane using a Trans-blot Turbo semi-dry transfer cell. Membranes were blocked in 5% milk powder in PBST for half an hour prior to incubation with primary antibody overnight at 4° C. or 1 hr at RT. Primary antibodies used in this study were: rabbit polyclonal anti-Cyclin F (1:300; cat# sc-952, Santa Cruz Biotechnology), mouse monoclonal anti-mCherry (1:300; cat#632543, Clontech) mouse monoclonal anti-TDP-43 (1:1000; cat# H00023435-M01, Abnova), mouse Monoclonal®-tubulin (1:1000; cat# T5168, Sigma). After incubation, membranes were washed in PBS-T three times for 10 minutes before fluorescently labeled IRDye 800CW. Goat Anti-Rabbit IgG (1:15,000; cat#926-32211, LI-COR) secondary antibody was applied for 30 minutes at RT. Proteins were imaged using a Li-Cor Odyssey imaging system at the appropriate wavelength.

Immunofluorescence

HEK293 Flp-In T-Rex cells stably expressing HA-tagged TDP-43 were grown on coverslips, then transfected with a construct encoding mCherry-Cyclin F using Lipofectamine 2000 (Invitrogen). After 24 hr, cells were fixed in 4% formaldehyde for 15 min, and washed in PBS. Cells were permeabilized using PBS containing 0.2% Triton X-100 for 10 min, then blocked using 1% BSA-PBST with 0.2M glycine for 30 mins. Permeabilized cells were incubated with 1:1000 anti-TDP-43 (ProteinTech) overnight at 4° C. Samples were then incubated with species-specific Alexa Fluor 488, then Hoechst. mCherry-Cyclin F and TDP-43 were imaged using a Zeiss microscope.

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Example 1

Expression of Wild-Type CCNF Transgene Reduces Pathological Levels of TDP-43 in Neurons Expressing a Mutant TDP-43 Allele Associated with ALS TDP-43$^{A315T}$ mice express human TDP-43 carrying the pathogenic A315T ALS mutation under the control of a neuronal inducible promoter system (Ke et al., 2015, supra). In the absence of doxycycline (Dox), TDP-43$^{A315T}$ mice express the transgene in neurons of the CNS, including motor cortex and spinal cord. TDP-43$^{A315T}$ mice develop early-onset and progressive motor deficits and muscular atrophy. Biochemically, accumulation of insoluble cytoplasmic TDP-43 was found in TDP-43$^{A315T}$ mice, together with a pronounced neuronal loss.

Figure 6:
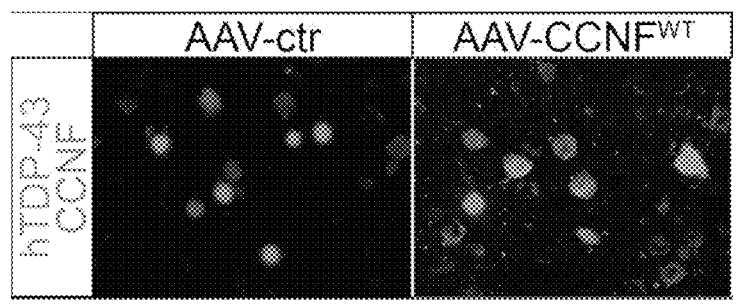
FIG. 6 is a photographic representation showing that expression of a wild-type CCNFtransgene reduces pathological levels of TDP-43 in neurons expressing a mutant TDP-43 allele (TDP-43$^{A315T}$) associated with the development of ALS. Robust expression of TDP-43$^{A315T}$ (red) is observed in neurons of TDP-43$^{A315T}$ mice, following induction of TDP-43$^{A315T}$ expression (removal of dox), as described in Ke et al. (2015. *Acta Neuropathologica*, 130(5): 661-678). However, in TDP-43$^{A315T}$ mice injected with AAV9-CCNF$^{WT}$, robust wild-type Cyclin F (green) expression is observed in neurons, with no evidence of TDP-43$^{A315T}$ (red) in the virally-transduced neurons, suggesting clearance of TDP-43.

To investigate whether wild-type CCNF expression can rescue accumulation of insoluble cytoplasmic TDP-43, AAV9-CCNF($1\times10^{12}$ viral particles) were injected into newborn TDP-43$^{A315T}$ transgenic mice, and at 4 weeks of age Dox was removed from their food to induce TOP-43A3157-expression. After 4 weeks in normal housing conditions, mice were cardiac perfused with 4% paraformaldehyde and fixed brain sections were evaluated immunohistochemically. Immunolabeling was performed using a human-specific TDP-43 antibody to detect the TDP-43$^{A315T}$, and Cyclin F is fused to a GFP reporter. As expected, in mice injected with AAV9-empty constructs, robust nuclear expression of TDP-43$^{A315T}$ (red) was observed in neurons (see FIG. 6). However, in AAV9-CCNF$^{WT}$ injected mice almost no expression of TDP-43$^{A315T}$ (red) was found in Cyclin F$^{WT}$ (green) expressing neurons.

These data demonstrate that it is possible to therapeutically deliver CCNF$^{WT}$ with a delivery vector such as AAV9, and it substantially reduces pathological levels of TDP-43 in neurons.

The citation of any reference herein should not be construed as an admission that such reference is available as "Prior Art" to the instant application.

Throughout the specification the aim has been to describe the preferred embodiments of the invention without limiting the invention to any one embodiment or specific collection of features. Those of skill in the art will therefore appreciate that, in light of the instant disclosure, various modifications and changes can be made in the particular embodiments exemplified without departing from the scope of the present invention. All such modifications and changes are intended to be included within the scope of the appended claims.

What is claimed is:

1. A method for reducing abnormal accumulation of TAR DNA-binding protein 43 (TDP-43) in motor neurons in a subject with amyotrophic lateral sclerosis (ALS) and/or frontotemporal dementia (FTD), wherein the abnormal accumulation of TDP-43 is the accumulation of TDP-43 in nuclear and/or cytoplasmic inclusions in motor neurons relative to motor neurons from a healthy control, the method comprising:

identifying the subject with ALS and/or FTD as having an abnormal accumulation of TDP-43 in motor neurons relative to motor neurons from a healthy control and determining that the subject with ALS and/or FTD has motor neurons with a reduced level and activity of cyclin F relative to motor neurons from a healthy subject that does not have ALS and/or FTD;

administering to the subject a construct comprising a nucleic acid sequence encoding cyclin F operably connected to a promoter that is operable in the motor neurons, and wherein the nucleic acid sequence encodes the amino acid sequence of SEQ ID NO: 3 or 6;

expressing the cyclin F in the motor neurons; and reducing the abnormal accumulation of TDP-43 in the motor neurons.

2. The method of claim 1, wherein the construct is in a form of a vector.

3. The method of claim 1, wherein the nucleic acid sequence is an RNA sequence.

4. The method of claim 2, wherein the vector is an adeno-associated virus (AAV) vector.

5. The method of claim 1, wherein the reduction of abnormal accumulation of TDP43 inhibits degradation of a motor neuron having a reduced level and activity of cyclin F relative to a motor neuron from a healthy subject that does not have ALS and/or FTD.

6. The method of claim 1, wherein the reduction of abnormal accumulation of TDP43 promotes survival of a motor neuron having a reduced level and activity of cyclin F relative to a motor neuron from a healthy subject that does not have ALS and/or FTD.

* * * * *

SEQUENCE LISTING

```
<160> NUMBER OF SEQ ID NOS: 6

<210> SEQ ID NO 1
<211> LENGTH: 4287
<212> TYPE: DNA
<213> ORGANISM: Homo sapiens

<400> SEQUENCE: 1
ctgcgcctgc gcgagggcta cgcgcgctcc ggccggggcg cgggcgcgct ctcaggcggg      60
ctccggcggc agcgacgcga gcgcggcgat ggggagcggc ggcgtggtcc actgtaggtg     120
tgccaagtgt ttctgttatc ctacaaagcg aagaataagg aggaggcccc gaaacctgac     180
catcttgagt ctccccgaag atgtgctctt tcacatcctg aaatggcttt ctgtagagga     240
catcctggcc gtccgagctg tacactccca gctgaaggac ctggtggaca accacgccag     300
tgtgtgggca tgtgccagct tccaggagct gtggccgtct ccagggaacc tgaagctctt     360
tgaaagggct gctgaaaagg ggaatttcga agctgctgtg aagctgggca tagcctacct     420
ctacaatgaa ggcctgtctg tgtctgatga ggcccgcgca gaagtgaatg gcctgaaggc     480
ctctcgcttc ttcagtctcg ctgagcggct gaatgtgggt gccgcacctt tcatctggct     540
cttcatccgc cctccgtggt cggtgagcgg aagctgctgc aaggccgtgg ttcacgagag     600
cctcagggca gagtgccagc tgcagaggac tcacaaagca tccatattgc actgcttggg     660
cagagtgctg agtctgttcg aggatgagga gaagcagcag caggcccatg acctgtttga     720
ggaggctgct catcagggat gtctgaccag ctcctacctc ctctgggaaa gcgacaggag     780
gacagatgtg tcagatcctg ggcgatgcct ccacagcttc cgaaaactca gggactacgc     840
tgccaaaggc tgctgggaag cgcagctgtc tttagccaaa gcctgtgcaa atgcaaacca     900
gcttggactg gaggtgagag cttccagtga gatcgtctgc cagctatttc aggcttccca     960
ggctgtcagt aaacaacaag tcttctccgt gcagaaggga ctcaatgaca caatgaggta    1020
```

```
cattctgatc gactggctgg tggaagttgc caccatgaag gacttcacaa gcctgtgcct    1080
gcacctgacc gtggagtgtg tggaccggta cctgcggagg aggctggtgc cgcggtacag    1140
gctccagctg ctgggcatcg cctgcatggt catctgcacc cggtttatca gtaaagagat    1200
cctgaccatc cggaggccg tatggctcac ggacaacact tacaagtacg aggacctggt    1260
gagaatgatg ggcgagatcg tctccgcctt ggaagggaag attcgagtcc ccactgtggt    1320
ggattacaag gaggtcctgc tgacgctagt ccctgtggag ctgagaaccc agcacctgtg    1380
cagcttcctc tgcgagctct ccctgctgca caccagcctg tccgcctacg ccccagcccg    1440
cctggctgcc gcagccctgc tcctggccag actgacgcac gggcagacac agccctggac    1500
cactcagctg tgggacctca ccggattctc ctatgaagac ctcattccct gcgtcttgag    1560
cctccataag aagtgcttcc atgatgacgc ccccaaggac tacaggcaag tctctctgac    1620
cgccgtgaag cagcggtttg aggacaagcg ctatggagaa atcagccagg aagaggtgct    1680
gagctacagc cagttgtgtg ctgcattagg agtgacacaa gacagccccg acccccgac    1740
tttcctcagc acagggagagt ccacgccctt cctcagctct ccctcggggc ggagaaccaa    1800
acggaagcgg gagaacagcc tccaggaaga cagaggcagc ttcgttacca cccccactgc    1860
ggagctgtcc agccaggagg agacgctgct gggcagcttc ctcgactgga gcctggactg    1920
ctgctctggc tatgaaggcg accaggagag tgagggcgag aaggagggcg acgtgacagc    1980
tcccagcggc atcctcgatg tcaccgtggt ctacctgaac ccagaacagc attgctgcca    2040
ggaatccagt gatgaggagg cttgtccaga ggacaaggga cccaggacc acaggcact    2100
ggcgctggac acccagatcc ctgcaacccc tggacccaaa ccctggtcc gcaccagccg    2160
ggagccaggg aaggacgtca cgacctcagg gtactcctcc gtcagcaccg caagtcccac    2220
aagctccgtg gacggtggct gggggcccct gccccaacct acctcagtgc tgtccctgga    2280
cagtgactcg cacacacagc cctgccacca tcaggccagg aagtcatgtt tacagtgtcg    2340
tcccccaagt cccccggaga gcagtgttcc ccagcaacag gtgaagcgga taaacctatg    2400
catacacagt gaggaggagg acatgaacct gggccttgtg aggctgtaag tgtgtcagca    2460
catttgccgc agtggatgtg tactgagggg gctggaggcg aagggtggga gcatagcata    2520
ggaacgctgc atagaccatg gaggcctttg cgcagagagc agagaggatg acttgcggcc    2580
accaagtttc tgtctccgcg ggagtcccgt gcaagccatc agaatgttga atgagggtg    2640
aagagctcag atccctctct ttggaaagtt tagcctggaa gcagttggcc acactgtgtg    2700
gagggcacct ctctgtccct tccgtgtctc actgtctctg gaagcttcag cccatgtgtg    2760
tcctggtgtt cccagcccca ccagagcccc gtgccgggag ctgacagctt tcacgcttaa    2820
ggcacgtgtg acctgggtag tcagacacca cttgagcccc tgcccacatc tgctggtttg    2880
gggcttcagt ggggagctga cagctgtgag cacaccactg tcccctcatc cacctcggcc    2940
tgcatggggc acccacttcc ttctgggtgg ggcttccatg gtaaggggc ctgcgtccct    3000
gcacactgcg aggactgcct tggccacagg cccactccct acgacacgtg actcgtttta    3060
gagctctgtc ccagaggcgt tcgtatgtga cccacagatg gcgtcaatgt gaacacctct    3120
ctttgtgctg aatttctggg ccattctttt cctgtcttat ttctaaattt ccttcttcca    3180
agatgaaaac aaaagaaaaa cttaaaacag aaggtattaa aaaacaaga gattcccacc    3240
attatttagg ttcacctgca aaacaaaaat cttactccag cccctcaatg ccatcctgac    3300
acactttatg caaaaagaat tttcccagat aggctagcca gaaaaaactt caagtcctct    3360
```

| | |
|---|---|
| gtaacatctg aggtgaccaa gaggcagaag agcagagcag tcgggggccg tgtcctggct | 3420 |
| gatcccaact gcagctctgc tgtgggggcc cgtgggaggg aggcagaccc ctgggctttc | 3480 |
| ctgctggcca cggagactct gctcctgcat ggaaagggag cctgggagcc agcagcccac | 3540 |
| gcctggggag cctgcctggg gccatgtgac catggcctct ccctgggaac gggctgacca | 3600 |
| caacacaccc tgctgccatc cacttctgtt tactctgcaa atgtaagaaa gaaccacttg | 3660 |
| gccagaagtg tcccccagat gcttttttt tttttttttt ggagacagtt ttgctcttgt | 3720 |
| ctccccggct ggagtgcagt ggcatgatct caactctcaa ctcactgtaa cctccgcctc | 3780 |
| ccggatactc ctgcctcagc ctcctgggta gctgggatta caagcaccca accacgccca | 3840 |
| gctaattttt gtattttcgg tagagacggg atttcaccat gttggccagg ctagtctcga | 3900 |
| actcatgacc tcaagtgatc cgcccacttc ggtctcccaa agtgctggga ttacaggcat | 3960 |
| gagccacggc gcctggcccc caaatgctct tgaaccggaa acccagggat gggagatgct | 4020 |
| cactgagctg ctgcttttat gtgtgctggt gctatgtgtg ttcatgtccg cggcagctgt | 4080 |
| cttttgcta ctataaggga attctggcca ccctgggtgg ggtgtggtcg gggtgagaac | 4140 |
| ccaagcgttg gaactgtaga cccgtcctgt cgactgtgtg cccctgggca tgtgtgagcc | 4200 |
| tcagtttcct catctgtaag gggggcaatg atacctacct cacaggggtg ttgtgaggat | 4260 |
| taaatgtgag gaggatagtg gcagatg | 4287 |

<210> SEQ ID NO 2
<211> LENGTH: 2361
<212> TYPE: DNA
<213> ORGANISM: Homo sapiens

<400> SEQUENCE: 2

| | |
|---|---|
| atggggagcg gcggcgtggt ccactgtagg tgtgccaagt gtttctgtta tcctacaaag | 60 |
| cgaagaataa ggaggaggcc ccgaaacctg accatcttga gtctccccga agatgtgctc | 120 |
| tttcacatcc tgaaatggct ttctgtagag acatcctggg ccgtccgagc tgtacactcc | 180 |
| cagctgaagg acctggtgga caaccacgcc agtgtgtggg catgtgccag cttccaggag | 240 |
| ctgtggccgt ctccagggaa cctgaagctc tttgaaaggg ctgctgaaaa ggggaatttc | 300 |
| gaagctgctg tgaagctggg catagcctac ctctacaatg aaggcctgtc tgtgtctgat | 360 |
| gaggcccgcg cagaagtgaa tggcctgaag gcctctcgct tcttcagtct cgctgagcgg | 420 |
| ctgaatgtgg gtgccgcacc tttcatctgg ctcttcatcc gccctccgtg gtcggtgagc | 480 |
| ggaagctgct gcaaggccgt ggttcacgag agcctcaggg cagagtgcca gctgcagagg | 540 |
| actcacaaag catccatatt gcactgcttg ggcagagtgc tgagtctgtt cgaggatgag | 600 |
| gagaagcagc agcaggccca tgacctgttt gaggaggctg ctcatcaggg atgtctgacc | 660 |
| agctcctacc tcctctggga aagcgacagg aggacagatg tgtcagatcc tgggcgatgc | 720 |
| ctccacagct tccgaaaact cagggactac gctgccaaag gctgctggga agcgcagctg | 780 |
| tctttagcca aagcctgtgc aaatgcaaac cagcttggac tggaggtgag agcttccagt | 840 |
| gagatcgtct gccagctatt tcaggcttcc caggctgtca gtaaacaaca agtcttctcc | 900 |
| gtgcagaagg gactcaatga cacaatgagg tacattctga tcgactggct ggtggaagtt | 960 |
| gccaccatga aggacttcac aagcctgtgc ctgcacctga ccgtggagtg tgtggaccgg | 1020 |
| tacctgcgga ggaggctggt gccgcggtac aggctccagc tgctgggcat cgcctgcatg | 1080 |
| gtcatctgca cccggttat cagtaaagag atcctgacca tccggaggc cgtatggctc | 1140 |
| acggacaaca cttacaagta cgaggacctg gtgagaatga tgggcgagat cgtctccgcc | 1200 |

```
ttggaaggga agattcgagt ccccactgtg gtggattaca aggaggtcct gctgacgcta    1260
gtccctgtgg agctgagaac ccagcacctg tgcagcttcc tctgcgagct ctccctgctg    1320
cacaccagcc tgtccgccta cgccccagcc cgcctggctg ccgcagccct gctcctggcc    1380
agactgacgc acgggcagac acagccctgg accactcagc tgtgggacct caccggattc    1440
tcctatgaag acctcattcc ctgcgtcttg agcctccata gaagtgcttc catgatgac     1500 gcccccaagg actacaggca gtctctctg accgccgtga agcagcggtt tgaggacaag    1560
cgctatggag aaatcagcca ggaagaggtg ctgagctaca gccagttgtg tgctgcatta    1620
ggagtgacac aagacagccc cgaccccccg actttcctca gcacagggga gatccacgcc    1680
ttcctcagct ctccctcggg gcggagaacc aaacggaagc gggagaacag cctccaggaa    1740
gacagaggca gcttcgttac cacccccact gcggagctgt ccagccagga ggagacgctg    1800
ctgggcagct tcctcgactg gagcctggac tgctgctctg gctatgaagg cgaccaggag    1860
agtgagggcg agaaggaggg cgacgtgaca gctcccagcg gcatcctcga tgtcaccgtg    1920
gtctacctga acccagaaca gcattgctgc caggaatcca gtgatgagga ggcttgtcca    1980
gaggacaagg gaccccagga cccacaggca ctggcgctgg acacccagat ccctgcaacc    2040
cctggaccca aaccctggt ccgcaccagc cgggagccag ggaaggacgt cacgacctca    2100
gggtactcct ccgtcagcac cgcaagtccc acaagctccg tggacggtgg cttgggggcc    2160
ctgccccaac ctacctcagt gctgtccctg acagtgact cgcacacaca gccctgccac    2220
catcaggcca ggaagtcatg tttacagtgt cgtcccccaa gtccccgga gagcagtgtt    2280 ccccagcaac aggtgaagcg ataaaccta tgcatacaca gtgaggagga ggacatgaac    2340
ctgggccttg tgaggctgta a                                              2361

<210> SEQ ID NO 3
<211> LENGTH: 786
<212> TYPE: PRT
<213> ORGANISM: Homo sapiens

<400> SEQUENCE: 3

Met Gly Ser Gly Gly Val Val His Cys Arg Cys Ala Lys Cys Phe Cys
1               5                   10                  15

Tyr Pro Thr Lys Arg Arg Ile Arg Arg Pro Arg Asn Leu Thr Ile
            20                  25                  30

Leu Ser Leu Pro Glu Asp Val Leu Phe His Ile Leu Lys Trp Leu Ser
        35                  40                  45

Val Glu Asp Ile Leu Ala Val Arg Ala Val His Ser Gln Leu Lys Asp
    50                  55                  60

Leu Val Asp Asn His Ala Ser Val Trp Ala Cys Ala Ser Phe Gln Glu
65                  70                  75                  80

Leu Trp Pro Ser Pro Gly Asn Leu Lys Leu Phe Glu Arg Ala Ala Glu
                85                  90                  95

Lys Gly Asn Phe Glu Ala Ala Val Lys Leu Gly Ile Ala Tyr Leu Tyr
            100                 105                 110

Asn Glu Gly Leu Ser Val Ser Asp Glu Ala Arg Ala Glu Val Asn Gly
        115                 120                 125

Leu Lys Ala Ser Arg Phe Phe Ser Leu Ala Glu Arg Leu Asn Val Gly
    130                 135                 140

Ala Ala Pro Phe Ile Trp Leu Phe Ile Arg Pro Pro Trp Ser Val Ser
145                 150                 155                 160
```

-continued

Gly Ser Cys Cys Lys Ala Val Val His Glu Ser Leu Arg Ala Glu Cys
            165                 170                 175

Gln Leu Gln Arg Thr His Lys Ala Ser Ile Leu His Cys Leu Gly Arg
            180                 185                 190

Val Leu Ser Leu Phe Glu Asp Glu Lys Gln Gln Ala His Asp
            195                 200                 205

Leu Phe Glu Ala Ala His Gln Gly Cys Leu Thr Ser Ser Tyr Leu
210                 215                 220

Leu Trp Glu Ser Asp Arg Arg Thr Asp Val Ser Asp Pro Gly Arg Cys
225                 230                 235                 240

Leu His Ser Phe Arg Lys Leu Arg Asp Tyr Ala Ala Lys Gly Cys Trp
            245                 250                 255

Glu Ala Gln Leu Ser Leu Ala Lys Ala Cys Ala Asn Ala Asn Gln Leu
            260                 265                 270

Gly Leu Glu Val Arg Ala Ser Ser Glu Ile Val Cys Gln Leu Phe Gln
            275                 280                 285

Ala Ser Gln Ala Val Ser Lys Gln Gln Val Phe Ser Val Gln Lys Gly
            290                 295                 300

Leu Asn Asp Thr Met Arg Tyr Ile Leu Ile Asp Trp Leu Val Glu Val
305                 310                 315                 320

Ala Thr Met Lys Asp Phe Thr Ser Leu Cys Leu His Leu Thr Val Glu
                    325                 330                 335

Cys Val Asp Arg Tyr Leu Arg Arg Leu Val Pro Tyr Arg Leu
                    340                 345                 350

Gln Leu Leu Gly Ile Ala Cys Met Val Ile Cys Thr Arg Phe Ile Ser
            355                 360                 365

Lys Glu Ile Leu Thr Ile Arg Glu Ala Val Trp Leu Thr Asp Asn Thr
            370                 375                 380

Tyr Lys Tyr Glu Asp Leu Val Arg Met Met Gly Glu Ile Val Ser Ala
385                 390                 395                 400

Leu Glu Gly Lys Ile Arg Val Pro Thr Val Asp Tyr Lys Glu Val
                    405                 410                 415

Leu Leu Thr Leu Val Pro Val Glu Leu Arg Thr Gln His Leu Cys Ser
                    420                 425                 430

Phe Leu Cys Glu Leu Ser Leu Leu His Thr Ser Leu Ser Ala Tyr Ala
            435                 440                 445

Pro Ala Arg Leu Ala Ala Ala Leu Leu Leu Ala Arg Leu Thr His
            450                 455                 460

Gly Gln Thr Gln Pro Trp Thr Thr Gln Leu Trp Asp Leu Thr Gly Phe
465                 470                 475                 480

Ser Tyr Glu Asp Leu Ile Pro Cys Val Leu Ser Leu His Lys Lys Cys
                    485                 490                 495

Phe His Asp Asp Ala Pro Lys Asp Tyr Arg Gln Val Ser Leu Thr Ala
            500                 505                 510

Val Lys Gln Arg Phe Glu Asp Lys Arg Tyr Gly Glu Ile Ser Gln Glu
            515                 520                 525

Glu Val Leu Ser Tyr Ser Gln Leu Cys Ala Ala Leu Gly Val Thr Gln
            530                 535                 540

Asp Ser Pro Asp Pro Thr Phe Leu Ser Thr Gly Glu Ile His Ala
545                 550                 555                 560

Phe Leu Ser Ser Pro Ser Gly Arg Arg Thr Lys Arg Lys Arg Glu Asn
            565                 570                 575

```
Ser Leu Gln Glu Asp Arg Gly Ser Phe Val Thr Thr Pro Thr Ala Glu
            580                 585                 590

Leu Ser Ser Gln Glu Glu Thr Leu Leu Gly Ser Phe Leu Asp Trp Ser
        595                 600                 605

Leu Asp Cys Cys Ser Gly Tyr Glu Gly Asp Gln Glu Ser Glu Gly Glu
    610                 615                 620

Lys Glu Gly Asp Val Thr Ala Pro Ser Gly Ile Leu Asp Val Thr Val
625                 630                 635                 640

Val Tyr Leu Asn Pro Glu Gln His Cys Cys Gln Ser Ser Asp Glu
            645                 650                 655

Glu Ala Cys Pro Glu Asp Lys Gly Pro Gln Asp Pro Gln Ala Leu Ala
            660                 665                 670

Leu Asp Thr Gln Ile Pro Ala Thr Pro Gly Pro Lys Pro Leu Val Arg
        675                 680                 685

Thr Ser Arg Glu Pro Gly Lys Asp Val Thr Thr Ser Gly Tyr Ser Ser
        690                 695                 700

Val Ser Thr Ala Ser Pro Thr Ser Ser Val Asp Gly Gly Leu Gly Ala
705                 710                 715                 720

Leu Pro Gln Pro Thr Ser Val Leu Ser Leu Asp Ser Asp Ser His Thr
            725                 730                 735

Gln Pro Cys His His Gln Ala Arg Lys Ser Cys Leu Gln Cys Arg Pro
            740                 745                 750

Pro Ser Pro Pro Glu Ser Ser Val Pro Gln Gln Gln Val Lys Arg Ile
        755                 760                 765

Asn Leu Cys Ile His Ser Glu Glu Asp Met Asn Leu Gly Leu Val
770                 775                 780

Arg Leu
785

<210> SEQ ID NO 4
<211> LENGTH: 4196
<212> TYPE: DNA
<213> ORGANISM: Homo sapiens

<400> SEQUENCE: 4
ggtctgcgcc tgcgcgaggg ctacgcgcgc tccggccggg gcgcgggcgc gctctcaggc      60
gggctccggc ggcagcgacg cgagcgcggc gatgggagc ggcggcgtgg tccactgtag     120
gtgtgccaag tgtttctgtt atcctacaaa gcgaagaata aggaggaggc cccgaaacct    180
gaccatcttg agtctccccg aagatgtgct ctttcacatc ctgaaatggc tttctgtaga    240
ggacatcctg gccgtccgag ctggctgctg aaaaggggaa tttcgaagct gctgtgaagc    300
tgggcatagc ctacctctac aatgaaggcc tgtctgtgtc tgatgaggcc cgcgcagaag    360
tgaatggcct gaaggcctct cgcttcttca gtctcgctga gcggctgaat gtgggtgccg    420
cacctttcat ctggctcttc atccgcccctc cgtggtcggt gagcggaagc tgctgcaagg    480
ccgtggttca cgagagcctc agggcagagt gccagctgca gaggactcac aaagcatcca    540
tattgcactg cttgggcaga gtgctgagtc tgttcgagga tgaggagaag cagcagcagg    600
cccatgacct gtttgaggag gctgctcatc agggatgtct gaccagctcc tacctcctct    660
gggaaagcga caggaggaca gatgtgtcag atcctgggcg atgcctccac agcttccgaa    720
aactcaggga ctacgctgcc aaaggctgct gggaagcgca gctgtcttta gccaaagcct    780
gtgcaaatgc aaaccagctt ggactggagg tgagagcttc cagtgagatc gtctgccagc    840
```

```
tatttcaggc ttcccaggct gtcagtaaac aacaagtctt ctccgtgcag aagggactca    900
atgacacaat gaggtacatt ctgatcgact ggctggtgga agttgccacc atgaaggact    960
tcacaagcct gtgcctgcac ctgaccgtgg agtgtgtgga ccggtacctg cggaggaggc   1020
tggtgccgcg gtacaggctc cagctgctgg catcgcctg catggtcatc tgcacccggt    1080
ttatcagtaa agagatcctg accatccggg aggccgtatg gctcacggac aacacttaca   1140
agtacgagga cctggtgaga atgatgggcg agatcgtctc cgccttggaa gggaagattc   1200
gagtccccac tgtggtggat tacaaggagg tcctgctgac gctagtccct gtggagctga   1260
gaacccagca cctgtgcagc ttcctctgcg agctctccct gctgcacacc agcctgtccg   1320
cctacgcccc agcccgcctg ctgccgcag ccctgctcct ggccagactg acgcacgggc    1380
agacacagcc ctggaccact cagctgtggg acctcaccgg attctcctat gaagacctca   1440
ttccctgcgt cttgagcctc cataagaagt gcttccatga tgacgccccc aaggactaca   1500
ggcaagtctc tctgaccgcc gtgaagcagc ggtttgagga caagcgctat ggagaaatca   1560
gccaggaaga ggtgctgagc tacagccagt tgtgtgctgc attaggagtg acacaagaca   1620
gccccgaccc cccgactttc ctcagcacag gggagatcca cgccttcctc agctctccct   1680
cggggcggag aaccaaacgg aagcgggaga acagcctcca ggaagacaga ggcagcttcg   1740
ttaccacccc cactgcggag ctgtccagcc aggaggagac gctgctgggc agcttcctcg   1800
actggagcct ggactgctgc tctggctatg aaggcgacca ggagagtgag ggcgagaagg   1860
agggcgacgt gacagctccc agcggcatcc tcgatgtcac cgtggtctac ctgaacccag   1920
aacagcattg ctgccaggaa tccagtgatg aggaggcttg tccagaggac aagggacccc   1980
aggacccaca ggcactggcg ctggacaccc agatccctgc aacccctgga cccaaacccc   2040
tggtccgcac cagccgggag ccagggaagg acgtcacgac ctcagggtac tcctccgtca   2100
gcaccgcaag tcccacaagc tccgtggacg gtggcttggg ggccctgccc aacctacct   2160
cagtgctgtc cctggacagt gactcgcaca cacagccctg ccaccatcag gccaggaagt   2220
catgtttaca gtgtcgtccc ccaagtcccc cggagagcag tgttccccag caacaggtga   2280
agcggataaa cctatgcata cacagtgagg aggaggacat gaacctgggc cttgtgaggc   2340
tgtaagtgtg tcagcacatt tgccgcagtg gatgtgtact gaggggctg gaggcgaagg    2400
gtgggagcat agcataggaa cgctgcatag accatggagg cctttgcgca gagagcagag   2460
aggatgactt gcggccacca gtttctgtc ccgcgggag tcccgtgcaa gccatcagaa     2520
tgttgaaatg agggtgaaga gctcagatcc ctctcttgg aaagtttagc ctggaagcag    2580
ttggccacac tgtgtggagg gcacctctct gtcccttccg tgtctcactg tctctggaag   2640
cttcagccca tgtgtgtcct ggtgttccca gccccaccag agcccgtgc cgggagctga    2700
cagcttttcac gcttaaggca cgtgtgacct gggtagtcag acaccacttg agcccctgcc  2760
cacatctgct ggtttgggc ttcagtgggg agctgacagc tgtgagcaca ccactgtccc    2820
ctcatccacc tcggcctgca tggggcaccc acttccttct gggtgggct tccatggtaa    2880
gggggcctgc gtccctgcac actgcgagga ctgccttggc cacaggccca ctccctacga   2940
cacgtgactc gttttagagc tctgtcccag aggcgttcgt atgtgaccca cagatggcgt   3000
caatgtgaac acctctcttt gtgctgaatt tctgggccat tctttcctg tcttatttct    3060
aaatttcctt cttccaagat gaaaacaaaa gaaaaactta aaacagaagg tattaaaaaa   3120
acaagagatt cccaccatta tttaggttca cctgcaaaac aaaatctta ctccagcccc    3180
tcaatgccat cctgacacac tttatgcaaa aagaatttc ccagataggc tagccagaaa    3240
```

```
aaacttcaag tcctctgtaa catctgaggt gaccaagagg cagaagagca gagcagtcgg    3300
gggccgtgtc ctggctgatc ccaactgcag ctctgctgtg ggggcccgtg ggagggaggc    3360
agacccctgg gctttcctgc tggccacgga gactctgctc ctgcatggaa agggagcctg    3420
ggagccagca gcccacgcct ggggagcctg cctggggcca tgtgaccatg gcctctccct    3480
gggaacgggc tgaccacaac acaccctgct gccatccact tctgtttact ctgcaaatgt    3540
aagaaagaac cacttggcca gaagtgtccc ccagatgctt ttttttttt tttttggag    3600 acagttttgc tcttgtctcc ccggctggag tgcagtggca tgatctcaac tctcaactca    3660
ctgtaacctc cgcctcccgg atactcctgc ctcagcctcc tgggtagctg ggattacaag    3720
cacccaacca cgcccagcta ttttttgtat tttcggtaga cgggatttt caccatgttg    3780 gccaggctag tctcgaactc atgacctcaa gtgatccgcc cacttcggtc tcccaaagtg    3840
ctgggattac aggcatgagc cacggcgcct ggcccccaaa tgctcttgaa ccggaaaccc    3900
agggatggga gatgctcact gagctgctgc ttttatgtgt gctggtgcta tgtgtgttca    3960
tgtccgcggc agctgtcttt ttgctactat aagggaattc tggccaccct gggtggggtg    4020
tggtcggggt gagaacccaa gcgttggaac tgtagacccg tcctgtcgac tgtgtgcccc    4080
tgggcatgtg tgagcctcag tttcctcatc tgtaagggg gcaatgatac ctacctcaca    4140
ggggtgttgt gaggattaaa tgtgaggagg atagtggcaa aaaaaaaaaa aaaaaa       4196

<210> SEQ ID NO 5
<211> LENGTH: 1437
<212> TYPE: DNA
<213> ORGANISM: Homo sapiens

<400> SEQUENCE: 5
atgaggtaca ttctgatcga ctggctggtg gaagttgcca ccatgaagga cttcacaagc     60
ctgtgcctgc acctgaccgt ggagtgtgtg gaccggtacc tgcggaggag ctggtgccg    120 cggtacaggc tccagctgct gggcatcgcc tgcatggtca tctgcacccg gtttatcagt    180
aaagagatcc tgaccatccg ggaggccgta tggctcacgg acaacactta caagtacgag    240
gacctggtga aatgatggg cgagatcgtc tccgccttgg aagggaagat tcgagtcccc    300
actgtggtgg attacaagga ggtcctgctg acgctagtcc ctgtggagct gagaacccag    360
cacctgtgca gcttcctctg cgagctctcc ctgctgcaca ccagcctgtc cgcctacgcc    420
ccagcccgcc tggctgccgc agccctgctc ctggccagac tgacgcacgg gcagacacag    480
ccctggacca ctcagctgtg ggacctcacc ggattctcct atgaagacct cattccctgc    540
gtcttgagcc tccataagaa gtgcttccat gatgacgccc caaggacta caggcaagtc    600 tctctgaccg ccgtgaagca gcggtttgag acaagcgct atgagaaat cagccaggaa    660 gaggtgctga gctacagcca gttgtgtgct gcattaggag tgacacaaga cagccccgac    720 ccccgactt tcctcagcac aggggagatc cacgccttcc tcagctctcc ctcggggcgg    780
agaaccaaac ggaagcggga gaacagcctc caggaagaca gaggcagctt cgttaccacc    840
cccactgcgg agctgtccag ccaggaggag acgctgctgg gcagcttcct cgactggagc    900
ctggactgct gctctggcta tgaaggcgac caggagagtg agggcgagaa ggagggcgac    960
gtgacagctc ccagcggcat cctcgatgtc accgtggtct acctgaaccc agaacagcat    1020
tgctgccagg aatccagtga tgaggagct tgtccagagg acaagggacc ccaggaccca    1080
caggcactgg cgctggacac ccagatccct gcaacccctg acccaaaacc cctggtccgc    1140
```

```
accagccggg agccagggaa ggacgtcacg acctcagggt actcctccgt cagcaccgca   1200
agtcccacaa gctccgtgga cggtggcttg ggggccctgc cccaacctac ctcagtgctg   1260
tccctggaca gtgactcgca cacacagccc tgccaccatc aggccaggaa gtcatgttta   1320
cagtgtcgtc ccccaagtcc cccggagagc agtgttcccc agcaacaggt gaagcggata   1380
aacctatgca tacacagtga ggaggaggac atgaacctgg gccttgtgag gctgtaa      1437
```

<210> SEQ ID NO 6
<211> LENGTH: 478
<212> TYPE: PRT
<213> ORGANISM: Homo sapiens

<400> SEQUENCE: 6

```
Met Arg Tyr Ile Leu Ile Asp Trp Leu Val Glu Val Ala Thr Met Lys
1               5                   10                  15

Asp Phe Thr Ser Leu Cys Leu His Leu Thr Val Glu Cys Val Asp Arg
            20                  25                  30

Tyr Leu Arg Arg Arg Leu Val Pro Arg Tyr Arg Leu Gln Leu Leu Gly
        35                  40                  45

Ile Ala Cys Met Val Ile Cys Thr Arg Phe Ile Ser Lys Glu Ile Leu
    50                  55                  60

Thr Ile Arg Glu Ala Val Trp Leu Thr Asp Asn Thr Tyr Lys Tyr Glu
65                  70                  75                  80

Asp Leu Val Arg Met Met Gly Glu Ile Val Ser Ala Leu Glu Gly Lys
                85                  90                  95

Ile Arg Val Pro Thr Val Val Asp Tyr Lys Glu Val Leu Leu Thr Leu
            100                 105                 110

Val Pro Val Glu Leu Arg Thr Gln His Leu Cys Ser Phe Leu Cys Glu
        115                 120                 125

Leu Ser Leu Leu His Thr Ser Leu Ser Ala Tyr Ala Pro Ala Arg Leu
    130                 135                 140

Ala Ala Ala Leu Leu Leu Ala Arg Leu Thr His Gly Gln Thr Gln
145                 150                 155                 160

Pro Trp Thr Thr Gln Leu Trp Asp Leu Thr Gly Phe Ser Tyr Glu Asp
                165                 170                 175

Leu Ile Pro Cys Val Leu Ser Leu His Lys Lys Cys Phe His Asp Asp
            180                 185                 190

Ala Pro Lys Asp Tyr Arg Gln Val Ser Leu Thr Ala Val Lys Gln Arg
        195                 200                 205

Phe Glu Asp Lys Arg Tyr Gly Glu Ile Ser Gln Glu Glu Val Leu Ser
    210                 215                 220

Tyr Ser Gln Leu Cys Ala Ala Leu Gly Val Thr Gln Asp Ser Pro Asp
225                 230                 235                 240

Pro Pro Thr Phe Leu Ser Thr Gly Glu Ile His Ala Phe Leu Ser Ser
                245                 250                 255

Pro Ser Gly Arg Arg Thr Lys Arg Lys Arg Glu Asn Ser Leu Gln Glu
            260                 265                 270

Asp Arg Gly Ser Phe Val Thr Thr Pro Thr Ala Glu Leu Ser Ser Gln
        275                 280                 285

Glu Glu Thr Leu Leu Gly Ser Phe Leu Asp Trp Ser Leu Asp Cys Cys
    290                 295                 300

Ser Gly Tyr Glu Gly Asp Gln Glu Ser Glu Gly Glu Lys Glu Gly Asp
305                 310                 315                 320
```

```
Val Thr Ala Pro Ser Gly Ile Leu Asp Val Thr Val Val Tyr Leu Asn
                325                 330                 335

Pro Glu Gln His Cys Cys Gln Glu Ser Ser Asp Glu Glu Ala Cys Pro
            340                 345                 350

Glu Asp Lys Gly Pro Gln Asp Pro Gln Ala Leu Ala Leu Asp Thr Gln
        355                 360                 365

Ile Pro Ala Thr Pro Gly Pro Lys Pro Leu Val Arg Thr Ser Arg Glu
    370                 375                 380

Pro Gly Lys Asp Val Thr Thr Ser Gly Tyr Ser Ser Val Ser Thr Ala
385                 390                 395                 400

Ser Pro Thr Ser Ser Val Asp Gly Gly Leu Gly Ala Leu Pro Gln Pro
            405                 410                 415

Thr Ser Val Leu Ser Leu Asp Ser Asp Ser His Thr Gln Pro Cys His
            420                 425                 430

His Gln Ala Arg Lys Ser Cys Leu Gln Cys Arg Pro Pro Ser Pro Pro
        435                 440                 445

Glu Ser Ser Val Pro Gln Gln Gln Val Lys Arg Ile Asn Leu Cys Ile
    450                 455                 460

His Ser Glu Glu Glu Asp Met Asn Leu Gly Leu Val Arg Leu
465                 470                 475
```